US011453908B2

(12) United States Patent
Hsu et al.

(10) Patent No.: US 11,453,908 B2
(45) Date of Patent: Sep. 27, 2022

(54) METHODS AND KITS FOR TYPING KIR2DL ALLELES

(71) Applicant: MEMORIAL SLOAN KETTERING CANCER CENTER, New York, NY (US)

(72) Inventors: Katharine Hsu, New York, NY (US); Jean-Benoit Le Luduec, New York, NY (US)

(73) Assignee: MEMORIAL SLOAN KETTERING CANCER CENTER, New York, NY (US)

( * ) Notice: Subject to any disclaimer, the term of this patent is extended or adjusted under 35 U.S.C. 154(b) by 94 days.

(21) Appl. No.: 16/338,667

(22) PCT Filed: Sep. 28, 2017

(86) PCT No.: PCT/US2017/054172

§ 371 (c)(1),
(2) Date: Apr. 1, 2019

(87) PCT Pub. No.: WO2018/064413

PCT Pub. Date: Apr. 5, 2018

(65) Prior Publication Data

US 2019/0226017 A1 Jul. 25, 2019

Related U.S. Application Data

(60) Provisional application No. 62/403,099, filed on Oct. 1, 2016, provisional application No. 62/403,131, filed on Oct. 1, 2016.

(51) Int. Cl.

| | |
|---|---|
| ***C12Q 1/6858*** | (2018.01) |
| ***C12Q 1/6883*** | (2018.01) |
| ***C12Q 1/6806*** | (2018.01) |
| ***C12Q 1/6827*** | (2018.01) |
| ***C12Q 1/6853*** | (2018.01) |
| ***C12Q 1/686*** | (2018.01) |

(52) U.S. Cl.

CPC ........... *C12Q 1/6858* (2013.01); *C12Q 1/686* (2013.01); *C12Q 1/6806* (2013.01); *C12Q 1/6827* (2013.01); *C12Q 1/6853* (2013.01); *C12Q 1/6883* (2013.01); *C12Q 2600/156* (2013.01); *C12Q 2600/16* (2013.01); *C12Q 2600/172* (2013.01)

(58) Field of Classification Search

None

See application file for complete search history.

(56) References Cited

U.S. PATENT DOCUMENTS

| | | | | |
|---|---|---|---|---|
| 9,963,742 B2 * | 5/2018 | Hsu | C12Q 1/6883 | |
| 2011/0129830 A1 | 6/2011 | Ladner et al. | | |
| 2016/0040237 A1 * | 2/2016 | Hsu | C12Q 1/6883 | 506/9 |

FOREIGN PATENT DOCUMENTS

WO WO-2009/051672 A2 4/2009

OTHER PUBLICATIONS

Gagne et al Human Immunology. 2002. 63: 271-280 (Year: 2002).*

Thesis. "Killer-cell Immunoglobulin-like Receptor (KIR) Polymorphism: Functional Implications and Clinical Relevance" UMI No. U591999, published by ProQuest LLC. 2013, available via URL: <core.ac.uk/download/pdf/78075555.pdf> (Year: 2013).*

Sigma Aldrich. "PCR/qPCR/dPCR Assay Design", p. 1-10, Aug. 2012, available via URL: <sigmaaldrich.com/technical-documents/articles/biology/pcr-qpcr-dpcr-assay-design.html> (Year: 2012).*

S. Murdoch et al: "Detailed gene and allele content analysis of three homozygous KIR haplotypes", Tissue Antigens, vol. 68, No. 1, Jul. 1, 2006 (Jul. 1, 2006), pp. 72-77.

Vilches C et al: "Facilitation of KIR genotyping by a PCR-SSP method that amplifies short DNA fragments", Tissue Antigens, Munksgaard, Copenhagen, DK,vol. 70, No. 5, Nov. 1, 2007 (Nov. 1, 2007), pp. 415-422.

International Search Report and Written Opinion, PCT/US2017/054172 (dated Feb. 13, 2018).

GenBank Accession NC_000019.10. *Homo sapiens* chromosome 19, GRCh38.p7 Primary Assembly [Region 54769208-54784326, retrieved from: https://www.ncbi.nlm.nih/gov/nuccore/NC_000019.10?report=genbank&from54769208&to=54784326> (Jun. 6, 2016).

* cited by examiner

*Primary Examiner* — Carla J Myers

(74) *Attorney, Agent, or Firm* — Foley & Lardner LLP

(57) ABSTRACT

Disclosed herein are methods and compositions such as primers, primer pairs, and kits for typing KIR2DL1, KIR2DL2, Sand KIR2DL3 alleles. The compositions and methods disclosed herein are useful in the selection of most appropriate donors for HCT.

11 Claims, 14 Drawing Sheets

Specification includes a Sequence Listing.

Figure 2. KIR2DL1 polymorphism

A

| KIR2DL1 alleles | PCR reactions | | | | | | Optional reactions | | | | Individuals in the learning cohort (426) | Individuals in the testing cohort (230) | D1 | | | | | | | | | D2 | | | | | | | ST | | | TM | | CYT | | | | Group |
|---|---|---|---|---|---|---|---|---|---|---|---|---|---|---|---|---|---|---|---|---|---|---|---|---|---|---|---|---|---|---|---|---|---|---|---|---|---|---|
| | 1 | 2 | 3 | 4 | 5 | 6 | 1* | 2* | 3* | 4* | | | 15 | 16 | 35 | 44 | 56 | 67 | 84 | 90 | 99 | 106 | 114 | 131 | 154 | 163 | 179 | 182 | 216 | 221 | 226 | 245 | 246 | 275 | 282 | 296 | 312 | |
| *003 | ■ | ■ | | | | ■ | ■ | | | | 260 | 157 | G | R | E | M | H | S | T | V | I | E | L | R | P | D | G | H | K | R | L | R | W | D | T | R | T | G*003 |
| *023 | ■ | ■ | | | | ■ | ■ | | | | 0 | 0 | - | - | - | - | - | - | P | L | - | - | - | - | - | - | - | - | - | - | - | - | - | - | - | - | - | G*003 |
| *025 | ■ | ■ | | | | ■ | ■ | | | | 0 | 0 | - | - | - | - | - | - | - | - | - | - | - | W | - | - | - | - | - | - | - | - | - | - | - | - | - | G*003 |
| *017 | ■ | ■ | | | | ■ | ■ | | | | 0 | 0 | - | - | - | - | - | - | - | - | - | - | - | - | - | - | - | - | - | Q | - | - | - | - | - | - | - | G*003 |
| *016 | ■ | ■ | | | | ■ | ■ | | | | 0 | 0 | - | - | - | - | - | - | - | - | - | - | - | - | - | - | - | - | - | - | - | - | - | - | - | C | - | G*003 |
| *015 | ■ | ■ | | | | ■ | ■ | | | | 0 | 0 | - | - | - | - | - | - | - | - | - | - | - | - | - | - | - | - | - | - | - | - | - | E | - | - | - | G*003 |
| *014 | ■ | ■ | | | | ■ | ■ | | | | 0 | 0 | - | - | - | - | - | - | - | - | - | - | - | - | - | - | S | - | - | - | - | - | - | - | - | - | - | G*003 |
| *018 | ■ | ■ | | | | ■ | ■ | | | | 0 | 0 | - | - | - | - | - | - | - | - | - | - | - | - | - | - | - | - | - | - | - | - | - | - | P | - | - | G*003 |
| *009 | ■ | ■ | | | | ■ | ■ | | | | 2 | 0 | - | - | - | - | - | - | - | - | - | - | - | - | - | - | - | - | - | - | - | - | - | - | V | - | - | G*003 |
| *020 | ■ | ■ | | | | ■ | ■ | | | ■ | 3 | 0 | - | - | - | - | - | G | - | - | - | - | - | - | - | - | - | - | - | - | - | - | - | - | - | - | - | G*003 |
| *005 | ■ | ■ | | | | ■ | ■ | | | | 0 | 0 | - | - | - | - | - | - | - | - | - | - | - | - | - | - | - | - | - | - | - | - | - | - | - | - | A | G*003 |
| *006 | | ■ | ■ | | | | ■ | | | | 0 | 3 | - | - | - | - | - | - | - | - | - | - | - | - | - | - | - | - | - | - | - | C | - | - | - | - | - | *006 |
| *012 | ■ | ■ | | | | | ■ | | | | 0 | 1 | - | - | - | - | - | - | - | - | - | - | P | - | - | - | - | - | - | - | - | - | - | - | - | - | - | G*012 |
| *019 | ■ | ■ | | | | | ■ | | | | 0 | 0 | - | - | - | - | - | - | - | - | - | - | P | - | - | - | - | - | - | - | V | - | - | - | - | - | - | G*012 |
| *026 | ■ | ■ | | | | | ■ | | | | 0 | 0 | - | - | - | - | - | - | - | - | - | - | P | - | - | - | - | - | - | - | - | - | * | | | | | G*012 |
| *004 | | | ■ | ■ | | | ■ | | | | 84 | 57 | - | - | - | - | - | - | - | - | - | - | P | - | T | N | - | R | E | - | - | C | - | - | - | - | - | G*004 |
| *011 | | | ■ | ■ | | | | ■ | | | 0 | 1 | - | - | - | - | - | - | - | - | - | - | P | - | T | N | - | R | E | - | - | C | - | - | - | - | - | G*004 |
| *024 | | | ■ | ■ | | | ■ | | | | 0 | 0 | - | - | - | - | R | - | - | - | - | - | P | - | T | N | - | R | E | - | - | C | - | - | - | - | - | G*004 |
| *007 | | | ■ | ■ | | | ■ | | | | 3 | 0 | - | - | - | - | - | - | - | - | V | - | P | - | T | N | - | R | E | - | - | C | - | - | - | - | - | G*004 |
| *025 | | | ■ | ■ | | | ■ | | | | 0 | 0 | - | - | * | | | | | | | | | | | | | | | | | | | | | | | G*004 |
| *010 | ■ | | | ■ | | | ■ | | | | 0 | 2 | - | - | - | - | - | - | - | - | - | - | P | - | T | N | - | R | E | - | - | - | - | - | - | - | - | *010 |
| *002 | ■ | ■ | | | ■ | | | ■ | | | 178 | 87 | - | P | - | - | - | - | - | - | - | - | P | - | - | - | - | - | - | - | - | - | - | - | - | - | - | G*002 |
| *021 | ■ | ■ | | | ■ | | | ■ | | | 1 | 0 | - | P | - | - | - | - | - | - | - | Q | P | - | - | - | - | - | - | - | - | - | - | - | - | - | - | G*002 |
| *008 | ■ | ■ | | | | | | ■ | ■ | | 4 | 1 | D | P | - | - | - | - | - | - | - | - | P | - | - | - | - | - | - | - | - | - | - | - | - | - | - | *008 |
| *022 | ■ | ■ | | | ■ | | ■ | | | | 0 | 1 | - | P | - | K | - | - | - | - | - | - | P | - | - | - | - | - | - | - | - | - | - | - | - | - | - | G*001 |
| *001 | ■ | ■ | | | ■ | | ■ | | | | 76 | 17 | - | P | - | - | - | - | - | - | - | - | P | - | - | - | - | - | - | - | - | - | - | - | - | - | - | G*001 |

Figure 2. B

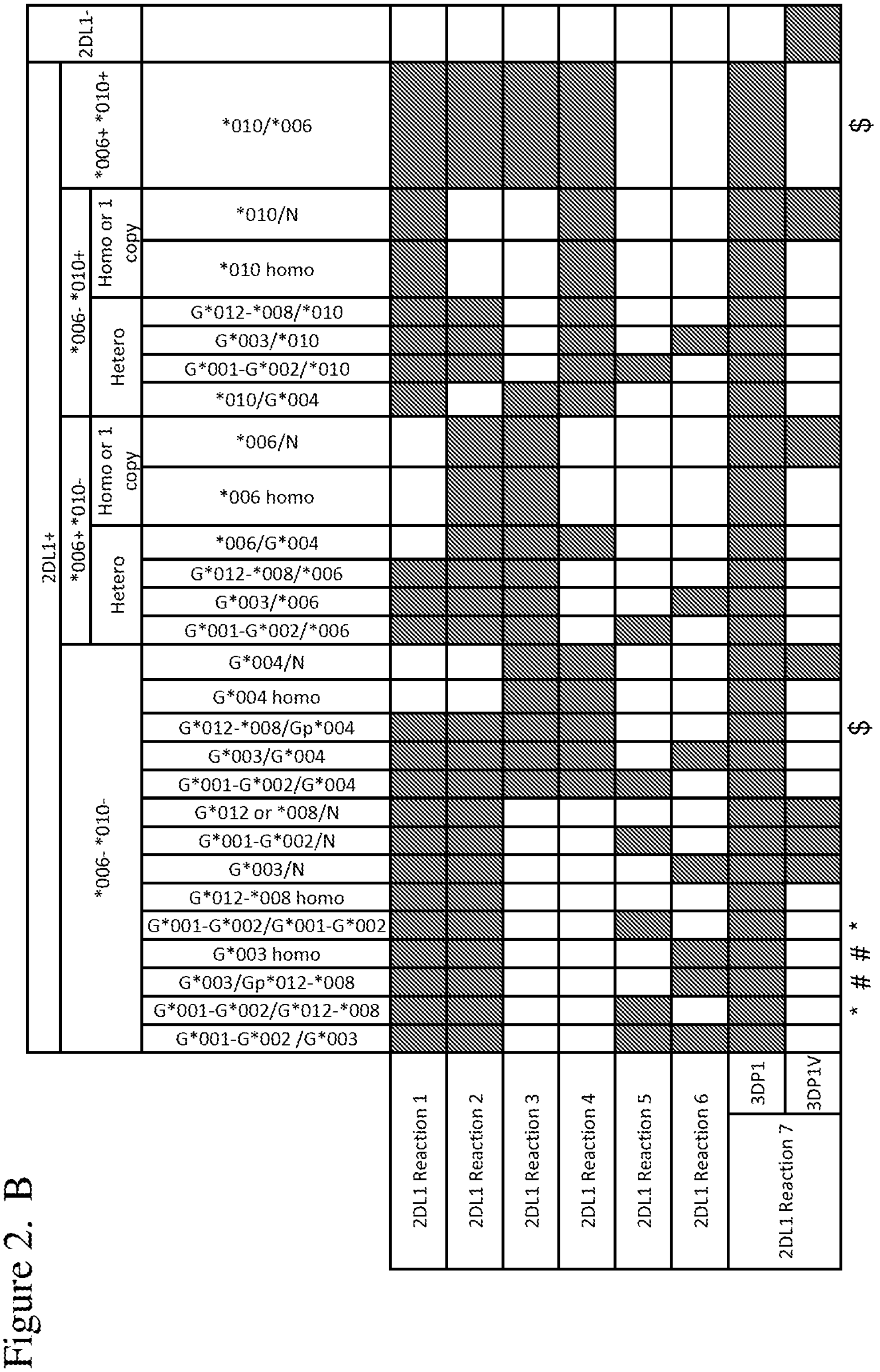

If Presence of G*001-G*002 or G*012-*008, need to do the optional reactions

Figure 2. B

| | | | | | 2DL1 Reaction 1 | 2DL1 Reaction 2 | 2DL1 Reaction 3 | 2DL1 Reaction 4 | 2DL1 Reaction 5 | 2DL1 Reaction 6 | 2DL1 Reaction 7 | 3DP1 | 3DP1V | |
|---|---|---|---|---|---|---|---|---|---|---|---|---|---|---|
| 2DL1+ | *006+ *010+ | | | *010/*006 | ▨ | ▨ | ▨ | ▨ | | | ▨ | | | $ |
| | *006- *010+ | Homo or 1 copy | | *010/N | ▨ | | | ▨ | | | ▨ | | | |
| | | | | *010 homo | ▨ | | | ▨ | | | ▨ | | | |
| | | Hetero | | G*012-*008/*010 | ▨ | ▨ | | ▨ | | | ▨ | | | |
| | | | | G*003/*010 | ▨ | | | ▨ | | ▨ | ▨ | | | |
| | | | | G*001-G*002/*010 | ▨ | | ▨ | ▨ | | | ▨ | | | |
| | | | | *010/G*004 | ▨ | | | ▨ | ▨ | | ▨ | | | |
| | *006+ *010- | Homo or 1 copy | | *006/N | | ▨ | | ▨ | | | ▨ | | | |
| | | | | *006 homo | | ▨ | | ▨ | | | ▨ | | | |
| | | Hetero | | *006/G*004 | | ▨ | | ▨ | ▨ | | ▨ | | | |
| | | | | G*012-*008/*006 | ▨ | ▨ | | ▨ | | | ▨ | | | |
| | | | | G*003/*006 | | ▨ | | ▨ | | ▨ | ▨ | | | |
| | | | | G*001-G*002/*006 | | ▨ | ▨ | ▨ | | | ▨ | | | |
| | *006- *010- | | | G*004/N | | | | ▨ | ▨ | | ▨ | | | |
| | | | | G*004 homo | | | | ▨ | ▨ | | ▨ | | | |
| | | | | G*012-*008/Gp*004 | ▨ | | | ▨ | ▨ | | ▨ | | | $ |
| | | | | G*003/G*004 | | | | ▨ | ▨ | ▨ | ▨ | | | |
| | | | | G*001-G*002/G*004 | | | ▨ | ▨ | ▨ | | ▨ | | | |
| | | | | G*012 or *008/N | ▨ | | | | | | ▨ | | | |
| | | | | G*001-G*002/N | | | ▨ | | | | ▨ | | | |
| | | | | G*003/N | | | | | | ▨ | ▨ | | | |
| | | | | G*012-*008 homo | ▨ | | | | | | ▨ | | | |
| | | | | G*001-G*002/G*001-G*002 | | | ▨ | | | | ▨ | | | * |
| | | | | G*003 homo | | | | | | ▨ | ▨ | | | # # |
| | | | | G*003/Gp*012-*008 | ▨ | | | | | ▨ | ▨ | | | # $ |
| | | | | G*001-G*002/G*012-*008 | ▨ | | ▨ | | | | ▨ | | | * |
| | | | | G*001-G*002 /G*003 | | | ▨ | | | ▨ | ▨ | | | |
| 2DL1- | | | | | | | | | | | | | ▨ | |

Method: Neighbor Joining; Best Tree; tie breaking = Systematic
Distance: Uncorrected ("p")
Gaps distributed proportionally Figure 4. KIR2DL2 polymorphism

A

| KIR2DL2 alleles | PCR reactions | | | | Optional reactions | | Individuals in the learning cohort (426) | Individuals in the testing cohort (230) | D1 | | | | D2 | | ST | | TM | | CYT | | | | | | | Group |
|---|---|---|---|---|---|---|---|---|---|---|---|---|---|---|---|---|---|---|---|---|---|---|---|---|---|---|
| | 1 | 2 | 3 | 4 | 1* | 2* | | | 3 | 16 | 35 | 41 | 148 | 167 | 200 | 216 | 245 | 248 | 268 | 269 | 272 | 297 | 312 | 316 | 319 | |
| ***003** | | | | | | | 110 | 61 | G | R | E | R | C | G | T | K | R | S | S | E | A | R | T | N | S | G*003 |
| *009 | | | | | | | 0 | 0 | - | - | - | - | R | - | - | - | - | - | - | - | - | - | - | - | - | *009 |
| *012 | | | | | | | 0 | 0 | E | - | - | - | - | - | - | - | - | - | - | - | - | - | - | - | - | G*003 |
| *013 | | | | | | | 0 | 0 | - | - | - | - | - | - | - | - | - | C | - | - | - | - | - | - | P | G*003 |
| ***006** | | | | | | | 0 | 5 | - | P | - | - | - | - | - | - | - | - | - | - | - | - | - | - | - | *006 |
| *011 | | | | | | | 0 | 0 | - | P | - | - | - | D | - | E | - | - | I | - | - | H | - | S | - | G*003 |
| *004 | | | | | | | 0 | 0 | - | P | Q | T | - | D | - | E | - | - | I | - | - | H | - | S | - | *004 |
| ***001** | | | | | | | 140 | 63 | - | - | - | - | - | - | I | - | - | - | - | - | - | - | A | - | - | G*001 |
| *007 | | | | | | | 0 | 0 | - | - | - | - | - | - | I | - | - | - | - | - | - | - | A | - | - | G*001 |
| *002 | | | | | | | 0 | 0 | - | - | - | - | - | - | I | - | - | - | R | Q | - | - | A | - | - | G*001 |
| *005 | | | | | | | 37 | 0 | - | - | - | - | - | - | I | - | - | - | - | - | - | - | - | - | - | G*005 |
| *008 | | | | | | | 0 | 0 | - | - | - | - | - | - | I | - | C | - | - | - | - | - | - | - | - | G*005 |
| *010 | | | | | | | 0 | 0 | - | - | - | - | - | - | I | - | C | - | - | - | Y | - | - | - | - | G*005 |

Figure 6. KIR2DL3 polymorphism
A
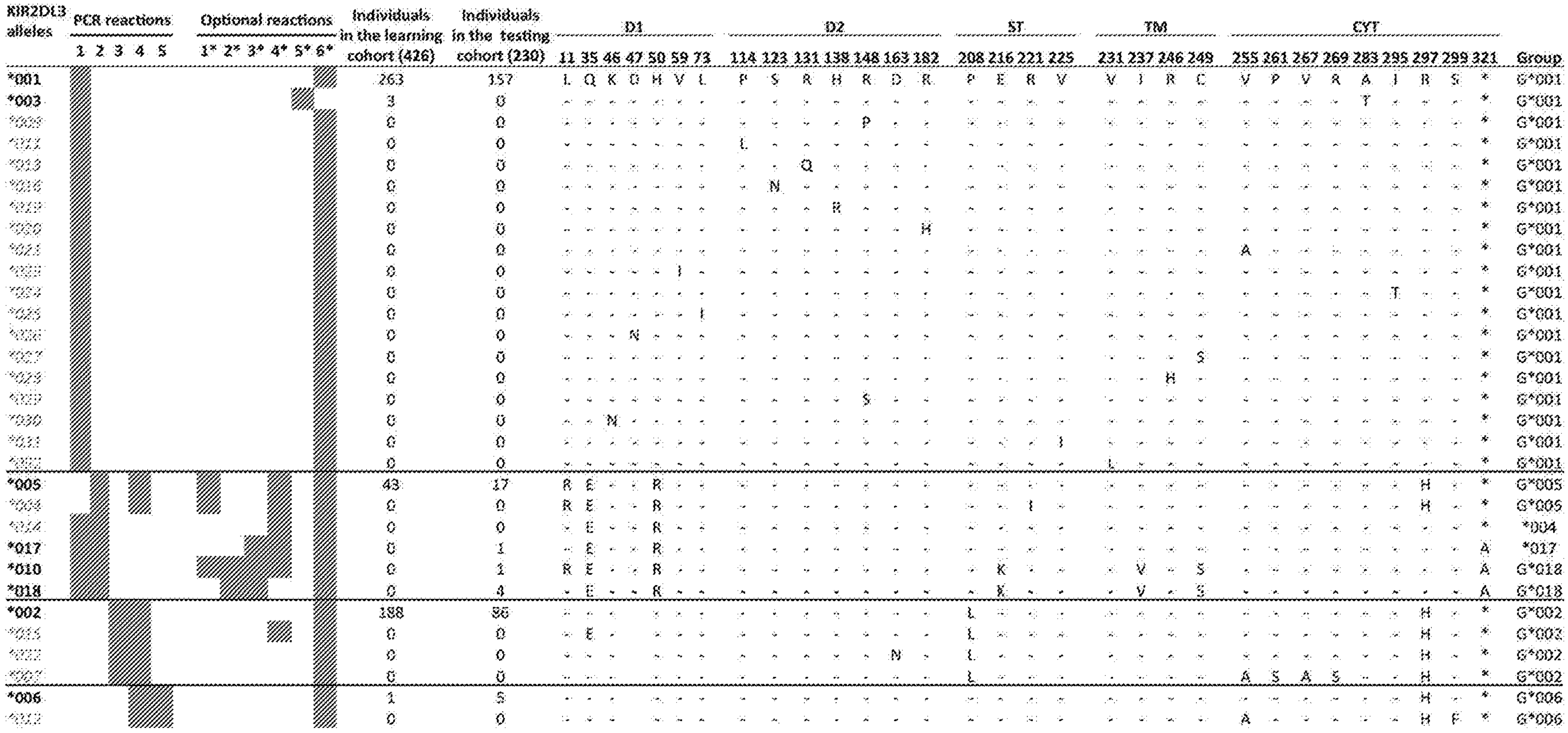

A
CenA
2DL3*005 2DL1*001 3DP1
2DL3*002 2DL1*002 3DP1
2DL3*001 2DL1*003 3DP1
CenB
2DS2 2DL2*001 2DL1*004 3DP1
2DS2 2DL2*003 2DL1 Neg 3DP1V
2DS2 2DL2*001 2DL1 Neg 3DP1V
2DS2 Neg 2DL2*006 2DL1*004 3DP1
B
C

Figure 9.
A
Surface expression of KIR2DL1*003 with different HLA-C
MFI of 2DL1 positive cells
C1/C1
C1/C2
C2/C2
G*003/N
G*003/*003
NS
B
G*002
G*003
G*004
C
Surface expression of KIR2DL3*001 with different HLA-C
MFI of 2DL3 positive cells
G*001/N
G*001/*001
D
MFI of 2DL3 cells
G*001/G*001
G*002/G*002
G*005 hetero
G*018 hetero
*006 hetero
2DL3 (180701)
2DL1/S1 (EB6B)

METHODS AND KITS FOR TYPING KIR2DL ALLELES

CROSS-REFERENCE TO RELATED APPLICATIONS

This application is a 371 U.S. national phase application of PCT/US2017/054172, filed Sep. 28, 2017, which claims the benefit of and priority to U.S. Application No. 62/403,099, filed Oct. 1, 2016, and U.S. Application No. 62/403,131, filed Oct. 1, 2016, the contents of which are incorporated herein by reference in their entireties.

SEQUENCE LISTING

The instant application contains a Sequence Listing which has been submitted electronically in ASCII format and is hereby incorporated by reference in its entirety. Said ASCII copy, created on May 24, 2021, is named 115872-0432_SL and is 84,891 bytes in size.

GOVERNMENT SUPPORT

This invention was made with government support under grant U01 AI069197 awarded by the National Institutes of Health. The government has certain rights in the invention.

BACKGROUND OF THE DISCLOSURE

Field of the Disclosure

The present disclosure generally relates to methods for typing KIR2DL1, KIR2DL2, and KIR2DL3 alleles and to primers, primer pairs and kits for elucidating these alleles and/or groups thereof.

Description of the Related Art

KIRs are a large family of receptors present on certain subsets of lymphocytes, including NK cells. The nomenclature for KTRs is based upon the number of extracellular domains (KIR2D or KIR3D) and whether the cytoplasmic tail is either long (KIR2DL or KIR3DL) or short (KIR2DS or KIR3DS). Within humans, the presence or absence of a given KIR is variable from one NK cell to another within the NK population present in a single individual. Within the human population there is a relatively high level of polymorphism of the KIR molecules, with certain KIR molecules being present in some, but not all individuals. Certain KIR gene products cause stimulation of lymphocyte activity when bound to an appropriate ligand. Certain KR gene products are inhibitory in nature. The known inhibitory KIR receptors include members of the KIR2DL and KIR3DL subfamilies.

Each of the KIR genes exhibits allelic variation as well as haplotypic variability in terms of the number and types of genes on the haplotypes. Haplotypic variability in gene content of KIR genes is the result of gene duplication and deletion throughout evolution (Pyo et al. *PLoS One.* 5, e15115 (2010). The polymorphisms between the alleles of a given KIR gene can occur in its extracellular, transmembrane, or cytoplasmic domains. Polymorphism at each of these 3 domains has been associated with significant biologic consequences. However, simple and cost-effective protocols for KIR2DL1, KIR2DL2, and KIR2DL3 allele assessment are yet to be developed.

SUMMARY OF THE DISCLOSURE

In one aspect the disclosure is directed to a kit for classifying KIR2DL1 alleles based on a polymerase chain reaction (PCR), comprising:

a first primer, which is a reverse primer and binds specifically to a region of KIR2DL1 alleles comprising nucleotide 4011;

a second primer, which is forward primer and binds specifically to a region of KIR2DL1 alleles comprising nucleotide 3680;

a third primer, which is a reverse primer and binds specifically to a region of KIR2DL1 alleles comprising nucleotide 5820;

a fourth primer which is a forward primer and binds specifically to a region of KIR2DL1 alleles comprising nucleotide 5499;

a fifth primer which is a reverse primer and binds specifically to a region of KIR2DL1 alleles comprising nucleotide 13609;

a sixth primer which is a forward primer and binds specifically to a region of KIR2DL1 alleles comprising nucleotide 13420;

a seventh primer which is a reverse primer which binds specifically to a region of KIR2DL1 alleles comprising nucleotide 5735;

an eighth primer which is a forward primer which binds specifically to a region of KIR2DL1 alleles comprising nucleotide 3790;

a ninth primer which is a reverse primer which binds specifically to a region of KIR2DL1 alleles comprising nucleotide 5761;

a tenth primer which is a forward primer which binds specifically to a region of KIR2DL1 alleles comprising nucleotide 5616; and instructions for performing PCR reactions.

In some embodiments, the kit may also comprise an eleventh primer which is a forward primer which binds specifically to a portion of an exon of KIR3DP1 which exon is absent from KIRDP1V; a twelfth primer which is a forward primer which binds specifically to a region of KIR3DP1V; and a thirteenth primer which is a reverse primer which binds specifically to a region of both KIR3DP1 and KIRDP1V.

In other embodiments the kit further comprises a fourteenth primer, which is a forward primer and binds specifically to a region of KIR2DL1 alleles comprising nucleotide 71; and a fifteenth primer which is a reverse primer and binds specifically to a region of KIR2DL1 alleles comprising nucleotide 281.

The kit may further comprise a sixteenth primer, which is a forward primer and binds specifically to a region of KIR2DL1 alleles comprising nucleotide 281; and a seventeenth primer which is a reverse primer and binds specifically to a region of KIR2DL1 alleles comprising nucleotide 620.

The kit may further comprise an eighteenth primer, which is a forward primer and binds specifically to a region of KIR2DL1 alleles comprising nucleotide 3787; and a nineteenth primer which is a reverse primer and binds specifically to a region of KIR2DL1 alleles comprising nucleotide 4110.

The kit may further comprise a twentieth primer, which is a forward primer and binds specifically to a region of KIR2DL1 alleles comprising nucleotide 3942 and a nineteenth primer which is a reverse primer and binds specifically to a region of KIR2DL1 alleles including nucleotide 4110.

The kit of any of the foregoing embodiments comprises instructions that provide pairing of the primers for conducting at least 6 and up to 11 ARMS PCR reactions, wherein said first primer and said second primer provide a primer pair for a first PCR reaction; said third primer and said fourth primer provide a primer pair for a second PCR reaction;
said fifth primer and said sixth primer provide a primer pair for a third PCR reaction; said third primer and said seventh primer provide a primer pair for a fourth PCR reaction;
said eighth primer and said second primer provide a primer pair for a fifth PCR reaction; and
said ninth primer and said tenth primer provide a pair for a sixth PCR reaction;
said 11th or 12$^{th}$ primer provides a pair with said 13$^{th}$ primer for a seventh PCR reaction;
said 14$^{th}$ and 15$^{th}$ primer provide a pair for a first optional reaction;
said 16$^{th}$ and 17$^{th}$ primer provide a pair for a second optional reaction;
said 18$^{th}$ and 19$^{th}$ primer provide a pair for a third optional reaction; and
said 20$^{th}$ and said 19$^{th}$ primer provide a pair for a fourth optional reaction.

The kit may further comprise instructions for conducting a 1$^{st}$ through a 7$^{th}$ PCR reaction and/or instructions for conducting a first optional PCR reaction; and/or instructions for conducting a 2$^{nd}$ optional PCR reaction and/or instructions for conducting a 3$^{rd}$ optional PCR reaction; and/or instructions for conducting a 4$^{th}$ optional PCR reaction; and/or instructions for identifying the presence of groups of KIR2DL1 alleles and/or individual alleles and/or allele combinations based on products from PCR reactions; and/or instructions that provide that the presence or absence of an amplification product from the corresponding PCR reaction indicates the presence or absence of a KIR2DL1 allele or group of alleles according to FIGS. 2A and/or 2B.

In some kit embodiments, one or more of the primers have the sequence corresponding to each reaction for KIR2DL1 alleles set forth in Table 1.

In another aspect the disclosure is directed to a method of typing the KIR2DL1 alleles in a subject, comprising
obtaining a sample containing genomic DNA from said subject,
performing at least six and up to 11 PCR reactions using the genomic DNA in said sample as template and the primer pairs provided by the kit of any one of embodiments above; and determining the KIR2DL1 alleles present in the subject based on detection of amplification products from the reactions.

Embodiments are directed to a first primer for determining KIR2DL1 alleles, which is a reverse primer and binds specifically to a region of KIR2DL1 alleles comprising nucleotide 4011; a second primer for determining KIR2DL1 alleles, which is forward primer and binds specifically to a region of KIR2DL1 alleles comprising nucleotide 3680; a third primer for determining KIR2DL1 alleles, which is a reverse primer and binds specifically to a region of KIR2DL1 alleles comprising nucleotide 5820; a fourth primer for determining KIR2DL1 alleles, which is a forward primer and binds specifically to a region of KIR2DL1 alleles comprising nucleotide 5499; a fifth primer for determining KIR2DL1 alleles, which is a reverse primer and binds specifically to a region of KIR2DL1 alleles comprising nucleotide 13609; a sixth primer for determining KIR2DL1 alleles, which is a forward primer and binds specifically to a region of KIR2DL1 alleles comprising nucleotide 13420; a seventh primer for determining KIR2DL1 alleles, which is a reverse primer which binds specifically to a region of KIR2DL1 alleles comprising nucleotide 5735; an eighth primer for determining KIR2DL1 alleles, which is a forward primer which binds specifically to a region of KIR2DL1 alleles comprising nucleotide 3790; a ninth primer for determining KIR2DL1 alleles, which is a reverse primer which binds specifically to a region of KIR2DL1 alleles comprising nucleotide 5761; a tenth primer for determining KIR2DL1 alleles, which is a forward primer which binds specifically to a region of KIR2DL1 alleles comprising nucleotide 5616.

Embodiments are directed to a primer pair for a first PCR reaction to elucidate KIR2DL1 alleles, comprising the first primer above and the 2$^{nd}$ primer above; a primer pair for a second PCR reaction to elucidate KIR2DL1 alleles, comprising the third primer and the fourth primer; a primer pair for a third PCR reaction to elucidate KIR2DL1 alleles, comprising the fifth primer and the sixth primer above; a primer pair for a fourth PCR reaction to elucidate KIR2DL1 alleles, comprising the seventh primer and the fourth primer above; a primer pair for a fifth PCR reaction to elucidate KIR2DL1 alleles, comprising the eighth primer and the first primer above; a primer pair for a sixth PCR reaction to elucidate KIR2DL1 alleles, comprising the ninth primer and the 10$^{th}$ primer above.

Embodiments regarding optional reactions are directed to a primer or primer pair for a first optional PCR reaction to elucidate KIR2DL1 alleles, comprising a fourteenth, forward, primer binding specifically to a region of KIR2DL1 alleles including nucleotide 71, a fifteenth, reverse, primer binding specifically to a region of KIR2DL1 alleles including nucleotide 281 or both; or to a primer or primer pair for a second optional PCR reaction to elucidate KIR2DL1 alleles comprising a sixteenth, forward, primer binding specifically to a region of KIR2DL1 alleles including nucleotide 281 or a seventeenth, reverse, primer binding specifically to a region of KIR2DL1 alleles including nucleotide 620 or both; or to a primer or primer pair for a third optional PCR reaction to elucidate KIR2DL1 alleles comprising an eighteenth, forward, primer binding specifically to a region of KIR2DL1 alleles including nucleotide 3787, or a nineteenth, reverse, primer binding specifically to a region of KIR2DL1 alleles including nucleotide 4110 or both; or to a primer or primer pair for a fourth optional PCR reaction to elucidate KIR2DL1 alleles comprising a twentieth, forward, primer binding specifically to region of KIR2DL1 alleles including nucleotide 3942, or a nineteenth, reverse, primer binding specifically to a region of KIR2DL1 alleles including nucleotide 4110, or both.

In another aspect the disclosure is directed to a method for determining the allelic group of KIR2DL1 alleles in a subject, comprising:
obtaining a sample containing genomic DNA from said subject,
performing at least one PCR reaction using the genomic DNA in said sample as template and one primer pair according to any one of embodiments above; and
determining one or more of the KIR2DL1 alleles present in the subject based on detection of an amplification product or products from the at least one PCR reaction.

In yet another aspect the disclosure is directed to a kit for classifying KIR2DL2 alleles based on a polymerase chain reaction (PCR), comprising:

a first primer, which is a forward primer and binds specifically to a region of KIR2DL2 alleles comprising nucleotide 5663 and in addition has a last nucleotide which binds specifically to an allele to be resolved;

a second primer, which is a reverse primer and binds specifically to a region of KIR2DL2 alleles comprising nucleotide 5820 and in addition has a last nucleotide which binds specifically to the same allele to be resolved by use of the first primer;

a third primer, which is a forward primer and binds specifically to a region of KIR2DL2 alleles comprising nucleotide 5663 and in addition has a last nucleotide which binds specifically to a second allele to be resolved;

a fourth primer, which is a reverse primer and binds specifically to a region of KIR2DL2 alleles comprising nucleotide 5820 and in addition has a last nucleotide which binds specifically to the same second allele to be resolved by use of the third primer;

a fifth primer, which is a forward primer and binds specifically to a region of KIR2DL2 alleles comprising nucleotide 13995;

a sixth primer which is a reverse primer and binds specifically to a region of KIR2DL2 alleles comprising nucleotide 14249;

a seventh primer which is a forward primer and binds specifically to a region of KIR2DL2 alleles comprising nucleotide 11984;

an eighth primer which is a reverse primer and binds specifically to a region of KIR2DL2 alleles comprising nucleotide 14249; and instructions for performing ARMS PCR reactions.

In some embodiments, the kit further comprises (i) a ninth primer which is a forward primer which binds specifically to a region of KIR2DL2 alleles comprising nucleotide 3754 and in addition has a last nucleotide which binds specifically to the same allele to be resolved by use of the ninth primer and (ii) a tenth primer which is a reverse primer which binds specifically to a region of KIR2DL2 alleles comprising nucleotide 3890 and in addition has a last nucleotide which binds specifically to the same allele to be resolved by use of the ninth primer.

In other embodiments, the kit further comprises (i) an eleventh primer which is a forward primer which binds specifically to a region of KIR2DL2 alleles comprising nucleotide 3754 and in addition has a last nucleotide which binds specifically to a second allele to be resolved by use of the eleventh primer, and (ii) a twelfth primer which is a forward primer which binds specifically to a region of KIR2DL2 alleles comprising nucleotide 3890 and in addition has a last nucleotide which binds specifically to the same second allele to be resolved by use of the ninth primer.

Embodiments are directed to first primer for determining KIR2DL2 alleles, which is a forward primer and binds specifically to a region of KIR2DL2 alleles comprising nucleotide 5663 and in addition has a last nucleotide which binds specifically to an allele of KIR2DL2 to be resolved; a second primer for determining KIR2DL2 alleles, which is a reverse primer and binds specifically to a region of KIR2DL2 alleles comprising nucleotide 5820 and in addition has a last nucleotide which binds specifically to the same allele of KIR2DL2 to be resolved by use of a first primer for determining KIR2DL2 alleles; a third primer for determining KIR2DL2 alleles, which is a forward primer and binds specifically to a region of KIR2DL2 alleles comprising nucleotide 5663 and in addition has a last nucleotide which binds specifically to a second allele of KIR2DL2 to be resolved; a fourth primer for determining KIR2DL2 alleles, which is a reverse primer and binds specifically to a region of KIR2DL2 alleles comprising nucleotide 5820 and in addition has a last nucleotide which binds specifically to the same second allele of KIR2DL2 to be resolved by use of a third primer for determining KIR2DL2 alleles; a fifth primer for determining KIR2DL2 alleles, which is a forward primer and binds specifically to a region of KIR2DL2 alleles comprising nucleotide 13995; a sixth primer for determining KIR2DL2 alleles, which is a reverse primer and binds specifically to a region of KIR2DL2 alleles comprising nucleotide 14249; a seventh primer for determining KIR2DL2 alleles, which is a forward primer and binds specifically to a region of KIR2DL2 alleles comprising nucleotide 11984; an eighth primer for determining KIR2DL2 alleles, which is a reverse primer and binds specifically to a region of KIR2DL2 alleles comprising nucleotide 14249.

Embodiments pertaining to determination of KIR2DL2 alleles include a primer pair for a first PCR reaction for determining KIR2DL2 alleles, comprising the first primer and the $2^{nd}$ primer for KIR2DL2 above; a primer pair for a second PCR reaction for determining KIR2DL2 alleles, comprising the third primer and the fourth primer for KIR2DL2 above; a primer pair for a third PCR reaction for determining KIR2DL2 alleles, comprising the fifth primer and the sixth primer for KIR2DL2 above; a primer pair for a fourth PCR reaction for determining KIR2DL2 alleles, comprising the seventh primer and the eighth primer for KIR2DL2 above.

A primer or primer pair for a first optional PCR reaction to elucidate KIR2DL2 alleles comprising an eleventh, forward, primer binding specifically to region of KIR2DL2 alleles including nucleotide 3754 and in addition having a last nucleotide specifically binding to a first allele of KIR2DL2 the presence or absence of which is to be determined, or a twelfth, reverse, primer binding specifically to a region of KIR2DL2 alleles including nucleotide 3890 and in addition having a last nucleotide specifically binding to the same first allele, or both.

In another aspect, a primer or primer pair is provided for a second optional PCR reaction to elucidate KIR2DL2 alleles comprising a thirteenth, forward, primer binding specifically to region of KIR2DL2 alleles including nucleotide 3754 and in addition having a last nucleotide specifically binding to a second allele of KIR2DL2 the presence or absence of which is to be determined, or a fourteenth, reverse, primer binding specifically to a region of KIR2DL2 alleles including nucleotide 3890 and in addition having a last nucleotide specifically binding to the same second allele, or both.

In another aspect the disclosure is directed to a method of typing the KIR2DL2 alleles in a subject, comprising obtaining a sample containing genomic DNA from said subject, performing at least 4 and up to 6 PCR reactions using the genomic DNA in said sample as template and the primer pairs of the present disclosure; and determining the KIR2DL2 alleles present in the subject based on detection of amplification products from the reactions.

In yet another aspect the disclosure is directed to a method for determining the allelic group of KIR2DL2 alleles in a subject, comprising:

obtaining a sample containing genomic DNA from said subject, performing at least one PCR reaction using the genomic DNA in said sample as template and at least one primer pair according to the present disclosure; and determining one or more of the KIR2DL2 alleles present in the subject based on detection of an amplification product or products from the at least one PCR reaction For KIR2DL3 there is the same pattern of embodiments:

Embodiments to a kit comprising all the primers of the 5 main reactions (each having a particular nucleotide target as specified in Table 1) for determining the presence of KIR2DL3 alleles; dependent embodiments to a kit, each more specific embodiment adding a primer pair from one of the 6 Optional Reactions; embodiments to the 10 individual primers of the 5 main PCR reactions and embodiments to primer pairs for the primer pairs of the same 5 main PCR reactions; embodiments to primers or primer pairs for the primers of one or more (up to 6) optional PCR reactions (including ARMS PCR); embodiments to a method of typing the KIR2DL3 alleles in a subject, comprising obtaining a sample containing genomic DNA from said subject, performing at least 5 and up to 11 PCR reactions using the genomic DNA in said sample as template and the primer pairs provided in the kit embodiments; and determining the KIR2DL3 alleles present in the subject based on detection of amplification products from the PCR reactions. Lastly embodiments to a method for determining the allelic group of KIR2DL3 alleles in a subject, comprising obtaining a sample containing genomic DNA from said subject, performing at least one PCR reaction using the genomic DNA in said sample as template and at least one primer pair according to the primer pair embodiments for the 5 main and for the 6 optional PCR reactions; and determining one or more of the KIR2DL3 alleles present in the subject based on detection of an amplification product or products from the at least one PCR reaction. For the primers of Optional reaction 10 and 11 it will be specified that in addition to the target nucleotide specified in Table 1 they will have a last nucleotide specific for a particular one of two alleles to be resolved, respectively, such that the primer designed for the first allele will not cause amplification if the first allele is not present and the primer designed for the second allele will not cause amplification if the second allele is not present in the sample.

BRIEF DESCRIPTION OF THE DRAWINGS

FIG. 2A is an alignment of the amino acid sequences of the 26 known KIR2DL1 allelic variants. Dash indicates identity with the consensus KIR2DL1*003, (*) indicates a stop codon. Structural domains are indicated: Ig-like domains (D1 and D2), Stem domain (ST), Transmembrane domain (TM), and Cytoplasmic domain (CYT). Six PCR reactions separate the six subgroups identified by phylogenetic analysis. Four additional PCR reactions separate alleles within subgroups. The frequency of the alleles present in the learning cohort of 426 individuals and in the testing cohort of 230 individuals are indicated. The group identification of the different alleles is indicated. In black bold the alleles tested by PCR, in grey Italic the alleles non tested. FIG. 2B is a table including the KIR2DL1 PCR interpretation guide. Positive PCR results are indicated in grey and negative PCR results are indicated in white. PCR profiles marked by *, #, or $ do not result in complete resolution of individual alleles. FIG. 2C is an image of an electrophoresis gel of the six KIR2DL1 PCR reactions. An additional reaction (R7) can be used to genotype the pseudo-genes KIR3DP1 (higher band) and KIR3DP1V (lower band) identifying the copy number of KIR2DL1. The alleles carrying KIR3P1V are always negative for KIR2DL1. Each PCR is multiplex and control primers amplify a fragment of the APC gene (813 bp) for DNA quality control. The combinations of the seven reactions create a unique signature for each of the different allelic groups. FIG. 2D is an image of electrophoresis gel of the eleven KIR2DL1 PCR reactions. Four optional PCR reactions are proposed to increase the resolution power of the method.

FIG. 4A shows an alignment of the amino acid sequences of the 13 known KIR2DL2 allelic variants. Dashes indicate identity with the consensus KIR2DL2*003 sequence. Structural domains are also indicated: Ig-like domains (D1 and D2), Stem domain (ST), Transmembrane domain (TM), and Cytoplasmic domain (CYT). Four PCR reactions separate the three subgroups identified by phylogenetic analysis. Two additional PCR reactions separate alleles within a subgroup. The frequencies of the alleles present in the learning cohort of 426 individuals and in the testing cohort of 230 individuals are also indicated. The group identification of the different alleles is indicated. In black bold the alleles tested by PCR, in grey Italic the alleles non tested. FIG. 4B is a table showing the KIR2DL2 PCR interpretation guide. PCR profiles marked by *, #, or $ do not result in complete resolution of individual alleles and need additional resolution steps using one or both optional reactions. Resolution can thus be obtained as between * G*003/G*003 versus G*003/G*009, and *003/*006 versus *006/*009; #G*005/G*005 vs. G*005/G*009 and $ G*001/G*005 vs. G*001/*009. The optional reactions permit resolution between *003/003 vs *003/006 and *003/N (null) vs. *003/006. The optional reactions do not distinguish between any of the combinations with *005 or 009 but these are quite rare. FIG. 4C is an image of an electrophoresis gel of the four KIR2DL2 PCR reactions. Each PCR is multiplex and control primers amplify a fragment of the APC gene (813 bp) for DNA quality control. FIG. 4D is an image of an electrophoresis gel of all six KIR2DL2 PCR reactions.

FIG. 6A shows an alignment of the amino acid sequences of the 32 known KIR2DL3 allelic variants based on the consensus sequence for KIR2DL3.001. Dashes indicate identity with the consensus KIR2DL3*001, (*) indicates a stop codon. Structural domains are also indicated: Ig-like domains (D1 and D2), Stem domain (ST), Transmembrane domain (TM), and Cytoplasmic domain (CYT). Five PCR reactions separate the four subgroups identified by phylogenetic analysis. Six additional (optional) PCR reactions separate individual alleles within subgroups. The frequency of the alleles present in the learning cohort of 426 individuals and in the testing cohort of 230 individuals is indicated. The group identification of the different alleles is indicated. The alleles tested by PCR are indicated in black boldface, and those not tested in grey italics. FIG. 6B is a table showing the KIR2DL3 PCR interpretation guide. PCR profiles marked by * or # are not completely resolved and need a higher resolution of genotyping using one or more of the six optional reactions as needed. FIG. 6C is an image of an electrophoresis gel of the five KIR2DL3 PCR reactions. Each PCR is multiplex and control primers amplify a fragment of the APC gene (813 bp) for DNA quality control. FIG. 6D is an image of an electrophoresis gel of the eleven KIR2DL3 PCR reactions. * G*018/G*018 vs. G*001/G*018 (cannot be solved by the supplemental reactions) and #G*001/G*005 vs. G*005/G*018 (optional 1 and 2).

FIG. 7A is a schematic showing the linkage disequilibrium between the KIR2DL1, KIR2DL2, KIR2DL3, KIR3DP1 alleles and the KIR2DS2 gene, which were calculated on a cohort of 230 donors. Seven most common combinations of alleles, three for the Centromeric A haplotype and four for the Centromeric B haplotype represent more than 95% of the donors in the cohort. FIG. 7B is a table depicting allelic segregation of the KIR2DL and KIR3DP1 alleles in CEPH families. KIR2DL subtyping was completed for three parent child quartets and matched previous KIR2DL allele typing. Paternal alleles are indicated by (*); maternal are indicated by (^). FIG. 7C is a table indicating KIR2DL subtype analysis of three generations of CEPH family individuals, which demonstrates Mendelian inheritance of alleles combinations established by the linkage disequilibrium study.

FIGS. 8A and 8B are graphs showing that KIR2DL1/L3 frequency correlates with the copy number of the alleles. The HLA-C groups and the copy number of the KIR2DL3 receptor are indicated. The presence of the cognate ligand did not influence the frequency of KIR2DL1 and KIR2DL3. FIG. 8C is a graph demonstrating that frequency expression of the different KIR2DL1 alleles. KIR2DL1*004 has a lower expression frequency in comparison to *006 (P<0.05) and *001&*002 (P<0.001) and has an impact on the KIR2DL1 frequency when co-expressed with another KIR2DL1 allele. The KIR2DL1*003 allele has a lower frequency in comparison to *001 and *002 (P<0.05). FIG. 8D is a graph showing the frequency of expression of the different KIR2DL2 alleles. KIR2DL2*006 has a lower frequency compared to *001/S2 or *003/S2 (P<0.01). The lower expression frequency observed for this allele is influenced by the absence of expression of KIR2DS2 on the same cell. FIG. 8E is a graph demonstrating the frequency of expression of different KIR2DL3 alleles. KIR2DL3*005 has a lower frequency of expression compared to *001 (P<0.0001) or *002 (P<0.001). KIR2DL3*018/*010 has a lower frequency of expression compared to *001 (P<0.05).

FIG. 9A is a graph of KIR2DL1*003 cell surface expression. The HLA-C groups and the copy number of the KIR2DL3 receptor are indicated. No effect of the copy number of the alleles was observed. KIR2DL1*003 cell surface expression was impacted by the expression of its cognate ligand in both hetero and homozygote donors, decreasing the cell surface expression of the receptor. FIG. 9B depicts KIR2DL1 cells surface expression of the alleles *002, *003 and *004 with or without the presence of their cognate ligands. KIR2DL1*002 exhibited a higher level of surface expression compared to *003 and *004. KIR2DL1*003 exhibited a higher level of surface expression compared to *004. The higher the cell surface expression of the KIR2DL1 allele, the more significant the impact of the cognate ligand. FIG. 9C shows KIR2DL3*001 cell surface expression. The HLA-C groups and the copy number of the KIR2DL3 receptor are indicated. No influence on KIR2DL3*001 cell surface expression was seen to be exerted by the copy number of the allele and no significant impact could be attributed to expression of the cognate ligand. The mean fluorescence intensity (MFI) was measured on the mAb anti-KIR2DL3 (Clone 180701). FIG. 9 shows KIR2DL1 cell surface expression of the alleles *001, *002 and *005, *018/*10 and *006. KIR2DL3*005 showed higher cell surface expression compared to *001 and *002 (P<0.0001). The level of expression of KIR2DL3*018/*010 was lower than that of *005 (P<0.05). The MFI were measured on the mAb anti KIR2DL2/L2/S2-(Clone CH-L).

FIG. 10A is a curve showing a decreased probability of relapse of AML patients within 1800 days of post hematopoietic stem cell transplantation from KIR2DL1*004 donors. FIG. 10B is a relapse curve indicating that patients receiving a transplant from KIR2DL3*005 positive donor have a higher rate of relapse in comparison to patients receiving a transplant from a KIR2DL3*005 negative donors.

DETAILED DESCRIPTION

Definitions

Figure 1:
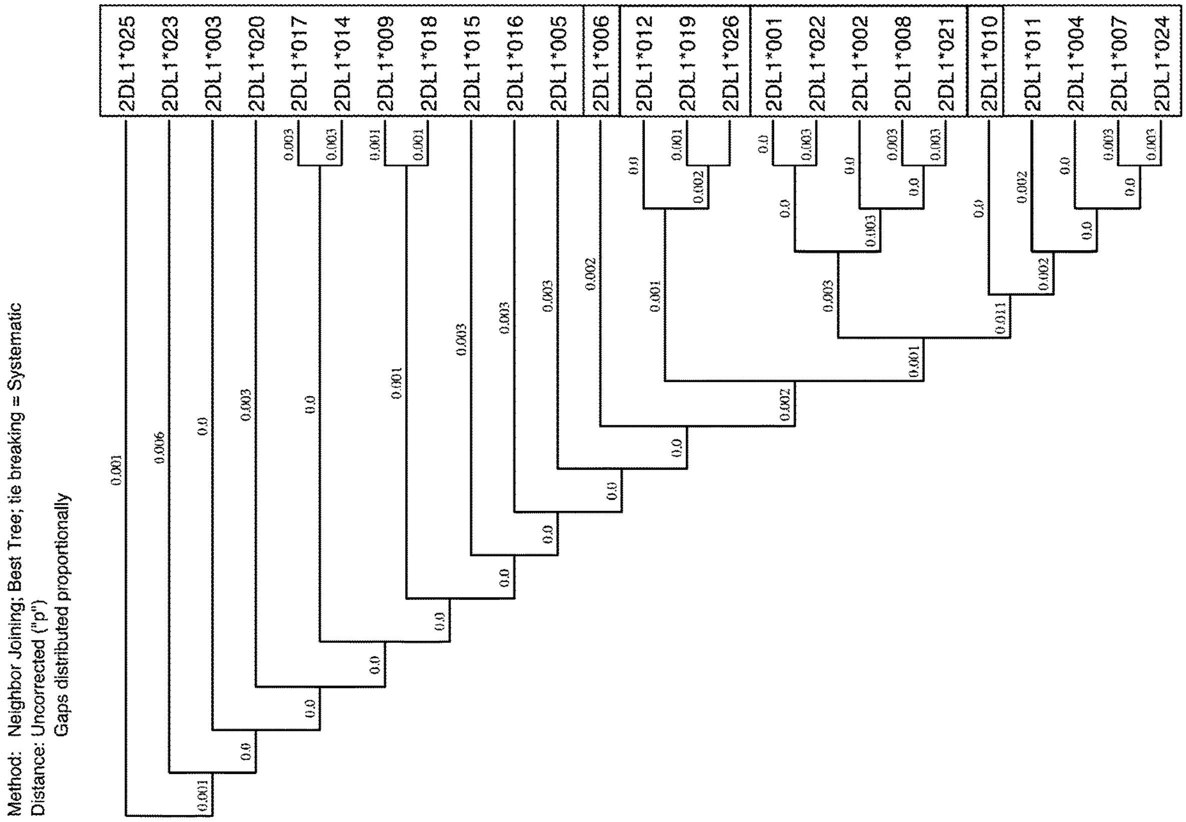
FIG. 1 is a schematic showing phylogenetic study of KIR2DL1 alleles. All alleles-coding sequence of KIR2DL1 from the EMBL-EBI IPD KIR database sequences were included in the alignment analyses. Mature amino acid protein sequences of KIR2DL1 alleles were aligned and analyzed by tree building methods: neighbor joining (Uncorrected method, Best Tree) with MacVector. Six distinct groups were determined.

The present disclosure provides methods for typing KIR2DL1, KIR2DL2, and KIR2DL3 alleles based on polymerase chain reactions (PCR), for example ARMS PCR.

By "typing KIR2DL1, or KIR2DL2, or KIR2DL3 alleles", it is meant that by using the PCR-based methods described in the present disclosure, the allelic types of the KIR2DL1, or KIR2DL2, or KIR2DL3 in a subject can be determined.

The present disclosure also provides oligonucleotide primers for amplifying regions of KIR2DL1, KIR2DL2, and KIR2DL3 alleles both in terms of disclosing the primers used and also by disclosing the sequences that can be recognized and target nucleotide to be amplified, which in turn readily permits a person of ordinary skill to design any number of primers that can accomplish the same goal. The primers can in turn be incorporated in kits for typing KIR2DL1, DL2 and DL3 from individuals and such kits represent an aspect of the present invention.

The term "primer", as used herein, means a synthetic oligonucleotide, typically designed for a nucleic acid hybridization assay or a polymerase chain reaction.

The term "primer pair" means a combination of a forward primer and a reverse primer for PCR.

Primers suitable for PCR should have a length that permits specific hybridization of the primers to their target DNA. Generally speaking, primers suitable for the method herein should have a length of at least 7, 8, 9 or 10 nucleotides, or preferably at least 11, 12, 13 or 14 nucleotides, or more preferably at least 15, 16, 17, or 18 nucleotides. Longer primers having 19, 20, 21, 22, 23, 24 or 25 nucleotides or more are also suitable for use herein. Typically, primers are not longer than 50 nucleotides, and preferably not longer than 40, 35, or 30 nucleotides. A variety of primers can be readily designed given the sequence information provided herein.

In the present disclosure, the inventors used amplification-refractory mutation system (ARMS) PCR (Little, S. Curr Protoc Hum Genet. 2001 May; Chapter 9:Unit 9.8. doi: 10.1002/0471142905.hg0908s07) in order to develop methods for classification of different subgroups of KIR2DL receptors.

Specifically disclosed is a medium resolution ARMS PCR method for distinguishing potential functional subgroups of the KIR2DL receptors. Six reactions define six subgroups of KIR2DL1; four reactions define three subgroups of KIR2DL2 and five reactions define four subgroups of KIR2DL3. Additional reactions were created to separate specific common alleles within the subgroups, as elucidated by phylogenetic study of the protein sequences. The most common allele subtypes were identified by genomic sequencing of a cohort of 426 European-American healthy donors; the typing protocols used herein were validated internally on 178 DNA samples from the same cohort and externally on an additional 220 samples from a validation cohort of 220 healthy donors. The linkage disequilibrium between the different alleles of KIR2DL was studied; the inventors showed that seven different allelic combinations represent more than 95% of the genotypes for KIR2DL1/L2/L3 alleles. Using primary, unmodified PBMC (n=220), the inventors performed a comprehensive phenotyping analysis by multiparametric flow cytometry. The results confirm the known patterns of differential KIR2DL allele expression among common subtypes and extends this knowledge to alleles that have not been previously characterized.

Differential expression patterns were consistently observed both with respect to the percentage of cells expressing the receptors and with respect to the expression density on individual cells. In sum, the findings disclosed herein enable straightforward allele-level study among the KIR2DL receptor family by providing methods for the rapid identification of allele subtypes and therefore allow better prediction of co-inheritance and relative expression. In addition, the present findings are useful in fine tuning the compatibility between donor and recipient of allogeneic hematopoietic cell transplantation.

In some instances, a sample that has one copy of one allele variant, and another copy of a different allele variant may be difficult to detect or distinguish or can on occasion provide a positive reaction, without showing whether there is one copy or two copies of a given allele variant. Additionally, when copies of two different allele variants are present, a PCR result can be a combination of both. To determine if a sample has one or two copies of a specific allele, the inventors of the present disclosure have devised optional reactions that can be used to distinguish between alleles that carry one copy or two copies of a specific allele variant.

As described in the present disclosure, the inventors have designed four optional reactions for detection of KIR2DL1 alleles, two optional reactions for detection of KIR2DL2 alleles, and six optional reactions for identification of KIR2DL3 alleles.

Additionally, optional reactions described herein can also be used to further separate alleles within each group or subgroup.

Primer Pairing and PCR Reactions

The primer pairs specifically exemplified in the present disclosure are paired as indicated in Table 1 to provide primer pairs (forward (F) and reverse (R)) for each PCR reaction described, which permits KIR2DL1, KIR2DL2, or KIR2DL3 allele identification. (Table 1 discloses SEQ ID NOS 1-59, respectively, in order of appearance)

| Reaction | Primers name | Nucleotide targeted | Sequence Primers | Size amplicon (bp) |
|---|---|---|---|---|
| Control | ControlF | NA | CCAAGCCCAACCTTAAGAAGAAAATTGGAG | 813 |
| | ControlR | NA | CCAAACCCACGGTACGCATGGGAACACTGC | |
| 2DL1 Reaction 1 | 2DL1R1F | 3680 | AGAGATAAGACACCAGGAAGGGGAAGCCCG | 388 |
| | 2DL1R1R | 4011 | TGTCCAGAGGGTCACTGGGAGCTGACTC | |
| 2DL1 Reaction 2 | 2DL1R2F | 5499 | GAGAGAGAGAGAGAGAGAGCATTAGGTCATAGTA | 383 |
| | 2DL1R2R | 5820 | TGACTTTGACCACTCGTATGGAGAGTCTT | |
| 2DL1 Reaction 3 | 2DL1R3F | 13420 | ATCCTCTTCATCCTCCTCTTCTTTCTCCTTCACT | 252 |
| | 2DL1R3R | 13609 | CAGTTCAGAATCAGGCAACGGTCTGTGAAT | |
| 2DL1 Reaction 4 | 2DL1R4F | 5499 | GAGAGAGAGAGAGAGAGAGCATTAGGTCATAGGA | 297 |
| | 2DL1R4R | 5735 | TGGCCTGGAATGTTCCGTTGACCTTGCT | |
| 2DL1 Reaction 5 | 2DL1R5F | 3790 | AACCTTCCCTCCTGGCCCACCCAGGTAC | 278 |
| | 2DL1R5R | 4011 | GATGTCCAGAGGGTCACTGGGAGCTGACGC | |
| 2DL1 Reaction 6 | 2DL1R6F | 5616 | ATATGAGAAACCTTCTCTCTCAGCCCAGTT | 202 |
| | 2DL1R6R | 5761 | GTGGGTGGCAGGGCCCAGAGGAAAGTAA | |
| 2DL1 Reaction 7 | 3DP1F | NA | ACGTGTTGTGAGTTGGTCATAGTGA | 649 |
| | 3DP1VF | NA | AAGTGGAAATGGGAGAATCTTCTGAC | 382 |
| | 3DP1R | NA | GCCCTCTGACCTGTGACCATGATC | |

-continued

| Reaction | Primers name | Nucleotide targeted | Sequence Primers | Size amplicon (bp) |
|---|---|---|---|---|
| 2DL1 Optional 1 | 2DL1O1F | 71 | GTTGGTCATAGTGAAGGACACTAGGTGTCAAATTCTATC | 274 |
| | 2DL1O1R | 281 | TCACCAACACACGCCATGCTGACGTC | |
| 2DL1 Optional 2 | 2DL1O2F | 281 | CTCCGGCAGCACCATGTCGCTCTTAT | 390 |
| | 2DL1O2R | 620 | CCGTAACTCCACCTCCAGGCCCATTA | |
| 2DL1 Optional 3 | 2DL1O3F | 3787 | AAACCTTCCCTCCTGGCCCCCCAAA | 376 |
| | 2DL1O3R | 4110 | CTTCCTTACAGCCACCTGGGTCTCCAGT | 376 |
| 2DL1 Optional 4 | 2DL1O4F | 3942 | GGGTCTCCAAGGCCAACTTCTCCATGG | 222 |
| | 2DL1O4R | 4110 | CTTCCTTACAGCCACCTGGGTCTCCACT | |
| 2DL2 Reaction 1 | 2DL2R1F | 5663 | TATCCAGGGAGGGGGAGGCCCATGATT | 211 |
| | 2DL2R1R | 5820 | TGAGACAGATATGGGGTTTCCTCACCAG | |
| 2DL2 Reaction 2 | 2DL2R2F | 5663 | TATCCAGGGAGGGGGAGGCCCATGATT | 210 |
| | 2DL2R2R | 5820 | GAGACAGATATGGGGTTTCCTCACCCA | |
| 2DL2 Reaction 3 | 2DL2R3F | 13995 | ACAGATGCTGCGGTAATGGACCAAGATT | 309 |
| | 2DL2R3R | 14249 | ATCTGGACTCAGCATTTGGAAGTTCCCC | |
| 2DL2 Reaction 4 | 2DL2R4F | 11984 | CTACTTCCAATCACCTGTGGAGATTCATG | 2322 |
| | 2DL2R4R | 14249 | ATCTGGACTCAGCATTTGGAAGTTCCTT | |
| 2DL2 Optional 1 | 2DL2O1F | 3754 | AACCTTCCCTCCTGGCCCACCCAGGTTC | 191 |
| | 2DL2O1R | 3890 | CATCATGGGACCGATGGAGAAGTTGGTT | |
| 2DL2 Optional 2 | 2DL2O2F | 3754 | AACCTTCCCTCCTGGCCCACCCAGGTAG | 191 |
| | 2DL2O2R | 3890 | CATCATGGGACCGATGGAGAAGTTGGGT | |
| 2DL3 Reaction 1 | 2DL3R1F | 13892 | ATGAAATGAGGGCCCAGAAGTGCCCTGT | 314 |
| | 2DL3R1R | 14154 | GGTGTCTTGGGCCTCTGAGAAGGAC | |
| 2DL3 Reaction 2 | 2DL3R2F | 3825 | CACAGAGAAGGGAAGTTTAAGGACACTTTGTG | 399 |
| | 2DL3R2R | 4168 | TATATGGCCCCTGTGTCTGTCCTTT | |
| 2DL3 Reaction 3 | 2DL3R3F | 9063 | CTGTCTCATGTTCTAGGAAACCCTTCAAATAGTTGGGT | 319 |
| | 2DL3R3R | 9303 | GAAGGATGTCAGATTGGCAATCATTCTTCTAGCTTGTAGGAAA | |
| 2DL3 Reaction 4 | 2DL3R4F | 13973 | GCCTGCAGGGAACAGAACAGTGAACAAG | 233 |
| | 2DL3R4R | 14154 | GGTGTCTTGGGCCTCTGAGAAGGCT | |
| 2DL3 Reaction 5 | 2DL3R5F | 3853 | CCTCATTGGAGAGCACCATGATGGGGCT | 430 |
| | 2DL3R5R | 4222 | CCTCTCTCTGGGACATGTCTGTCTGTCTGTCTGT | |
| 2DL3 Optional 1 | 2DL3O1F | 3708 | TAGGAGTCCACAGAAAACCTTCCCTCGG | 323 |
| | 2DL3O1R | 3976 | GAATGTCCGGACACTCTCACCTGTGACG | |
| 2DL3 Optional 2 | 2DL3O2F | 16795 | CCCTCCATCTGGGTGCTTGTCCTAAAGGCG | 213 |
| | 2DL3O2R | 16949 | GCGATGAAGGAGAAAGAAGAGGAGGAGGTC | |
| 2DL3 Optional 3 | 2DL3O3F | 17645 | TGAACAAGACCCTCAGGAGGTGACATTT | 169 |
| | 2DL3O3R | 17761 | TCATGGGCAGGAGACAACTTTGGATAT | |
| 2DL3 Optional 4 | 2DL3O4F | 7315 | TCCTGCAATGTTGGTCAGATGTCAGGTTCG | 643 |
| | 2DL3O4R | 7903 | AGGCCACAGGGCCCAACTCAGGTCGT | |
| 2DL3 Optional 5 | 2DL3O5F | 13892 | ATGAAATGAGGGCCCAGAAGTGCCCTGT | 278 |
| | 2DL3O5R | 14111 | CTCTGTGTGAAAACGCAGTGATTCAACTGTTT | |
| 2DL3 Optional 6 | 2DL3O6F | 13892 | ATGAAATGAGGGCCCGAAGTGCCCTGT | 278 |
| | 2DL3O6R | 14111 | CTCTGTGTGAAAACGCAGTGATTCAACTGTTC | |

The position of the targeted SNP is based on the following consensus nucleotide sequences:

for 2DL1 primers 2DL1 *00303 (IPD Acc No: KIR00005) (SEQ ID NO: 66), for 2DL2 primers 2DL2*0030101 (IPD Acc No: KIR00012) (SEQ ID NO: 67), for 2DL3 primers 2DL3 *0010101 (IPD Acc No: KIR00014) (SEQ ID NO: 68). Sequences of these are provided below. In some embodiments, the present disclosure provides kits comprising one or more primers that are at least 90-95% identical to any reverse primer sequence or forward primer sequences described in Table 1, wherein the one or more primers retain their SNP targeting specificity.

Acceptable variations in annealing temperature are −0.25 to +0.75° C. in annealing temperatures. Temperatures may vary according the specific PCR equipment used, depending on its current calibration, which can vary between machines, the quality of DNA preparation, or the reagents employed such as Taq, dNTP and specific PCR buffers. The extension time for all reactions is 1 minute, with the exception of KIR2DL2 reaction 4, which requires an extension time of 2.5 minutes. Reaction times may vary by −0:30 min and increased indefinitely. They vary based on the "ramp speed" of a PCR machine (the speed with which it changes between temperatures), the volume of a PCR reaction and the quality of DNA. 40 cycles are used for all reactions. These examples represent optimized number of cycles to provide good resolution of DNA. However, the number of cycles can vary −10 to unlimited. The number of cycles may vary depending on the quality and quantity of input DNA, detection reagents and imaging threshold can impact the number of cycles used.

To perform the PCR reactions, a sample containing genomic DNA is taken from the subject being tested. The sample can be a tissue or blood sample, including, but not limited to, blood, fractions of blood, peripheral blood cells, skin or tissue biopsies, buccal swab samples, and umbilical cord blood. In some embodiments, the sample is processed to enrich or isolate genomic DNA, which serves as the template for the PCR reactions.

Genomic DNA derived from subjects whose KIR2DL1, KIR2DL2, and KIR2DL3 genotypes are known can be used as controls.

In the present disclosure, the inventors created a comprehensive new genotyping method to distinguish the alleles of KIRL2DL1, KIR2DL2 and KIR2DL3. This was validated using 178 donors, who had been previously genotyped by sequencing. This method, designed to be used as a typing kit, provides a reliable alternative to sequencing methods for laboratories looking for medium resolution genotyping as it is time efficient, cost efficient, and requires only basic equipment.

Accordingly, in one aspect the present disclosure is directed to kits. A kit containing the above-described primers (Table 1) or equivalent primers having the same target. The kit can include primer pairing instructions, or be organized in a manner such that primer pairs are provided in separate compartments and properly labeled. The kit can also include instructions for PCR reactions and for interpretation of the results to permit KIR2DL1, KIR2DL2, and KIR2DL3 typing of a subject.

The linkage disequilibrium study demonstrated the predominant expression of seven different combinations of KIR2DL receptors, representing more than 95% of the 220 donors studied. The genotyping of the CEPH family further validated the robustness of the present method.

In the phenotyping study disclosed herein, the inventors confirmed the lower frequency of KIR2DL1*004 NK cells compared to other KIR2DL1 alleles as well as the relatively lower expression frequency of KIR2DL2*006, KIR2DL3*005 and KIR2DL3*018/*010 in comparison to other KIR2DL2/2DL3 alleles. The inventors further confirmed the impact of the expression of the cognate ligand of KIR2DL1 on cell surface expression and a differential expression of the alleles *002, *003 and *004. Additionally, differential cell surface expression of KIR2DL3*005 and KIR2DL3*018/*010, in comparison to the other KIR2DL3 alleles, was shown for the first time.

In accordance with the present disclosure, six primer sets are designed to target SNPs identified for the KIR2DL1 alleles. By "a primer targeting a SNP" it means that a primer binds to a nucleic acid region containing the SNP in a specific manner such that nucleic acids containing a particular nucleotide at the SNP position are amplified using this primer, and nucleic acids having a different nucleotide at the SNP position are not amplified using this primer. In addition to 6 reactions containing 6 primer sets for classification of KIR2DL1 alleles, the inventors of the present disclosure have developed an additional reaction (R7) to genotype the pseudo-genes KIR3DP1 and KIR3DP1V, which allows for identification of the copy number of KIR2DL1. The primers the inventors used are only one example. Different primers can be easily designed given the information provided herein on the sequences of the various alleles and polymorphisms thereof.

In one embodiment, the primers and PCR reactions disclosed herein permit allelic identification for the maternal and paternal KIR2DL1, KIR2DL2, and KIR2DL3 alleles in a subject, without requiring conventional sequencing analysis. Once the KIR2DL1, KIR2DL2, and KIR2DL3 allelic types are determined for the maternal and paternal alleles in a subject, the subject can be assigned to one of the KIR2DL1, KIR2DL2, or KIR2DL3 subgroups based on the combination of the subject's maternal and paternal alleles.

Based on the results described herein, it is anticipated that the present typing kits and methods will be helpful in donor selection, as the inventors and their co-workers have found for other KIR-HLA ligands. The inventors have already shown that the allelic combinations are in linkage disequilibrium with many of the theoretical combinations not being encountered at all. In fact, preliminary data set forth herein have shown that certain allelic KIR2DL combinations in a donor appear to reduce the chance of relapse in a recipient patient treated with heterologous bone marrow transplant for leukemia, specifically AML. These findings are relevant not only for AML but more broadly for any heterologous hematopoietic cell transplant and also for immunity against infection.

EXAMPLES

Materials and Methods

Genomic Analyses and Primer Design

All alleles-coding sequences of KIR2DL1, KIR2DL2 and KIR2DL3 from the EMBL-EBI IPD KIR database sequences (www.ebi.ac.uk/ipd/kir/alleles.html) were included in the alignment analyses. Gene alignments and phylogenetic analyses were performed using MacVector software version 13.5.5. Protein sequences of KIR2DL1 (FIG. 1), KIR2DL2 (FIG. 3) and KIR2DL3 (FIG. 5) alleles were aligned and analyzed by tree building methods: neighbor joining (Uncorrected method, Best Tree) with MacVector. KIR2DL1, KIR2DL2 and KIR2DL3 frequencies determined by genomic sequencing in a cohort of 426 European-American healthy donors were used in combination with the phylogenic analyses to determine the design of the PCR combination (FIG. 2A, 2C, 2D) (*PLoS One*. 2012; 7(11): e47491. doi: 10.1371/journal.pone.0047491. Epub 2012 Nov. 5.). For KIR2DL1 alleles, 6 PCR were designed to separate 6 different groups and 5 optional reactions to identify certain subgroups or individual alleles (FIG. 2A). One additional reaction for 3DP1-3DP1V (see reaction 7, FIGS. 2B and 2C) was designed in order to determine copy number of KIR2DL1 (*J Immunol*. 2002 Nov. 1; 169(9): 5118-29.). For KIR2DL2 alleles, four PCR reactions were devised to separate 3 distinct groups and 2 optional reactions were designed to identify specific subgroups (FIG. 2C). For KIR2DL3 alleles, five PCR reactions were designed to separate four distinct groups, and 6 optional reactions were developed in order to identify specific subgroups or individual alleles (FIG. 2D). The design of the primers was optimized using the software AmplifX (V1.7.0, crn2 m.univ-mrs.fr/pub/recherche/equipe-t-brue/jullien-nicolas/programmation/amplifx/), following the rules of ARMS design primers (Curr Protoc Hum Genet. 2001 May; Chapter 9:Unit 9.8. doi: 10.1002/0471142905.hg0908s07). All the primers are ARMS primers (except control primers and 2DL1 Reaction 7) and were designed for an annealing temperature of 63° C. (Table 1). A testing cohort of 220 healthy individuals was used to verify the specificity of the primers as well as 178 DNA from the learning cohort.

PCR Reactions

Figure 2:
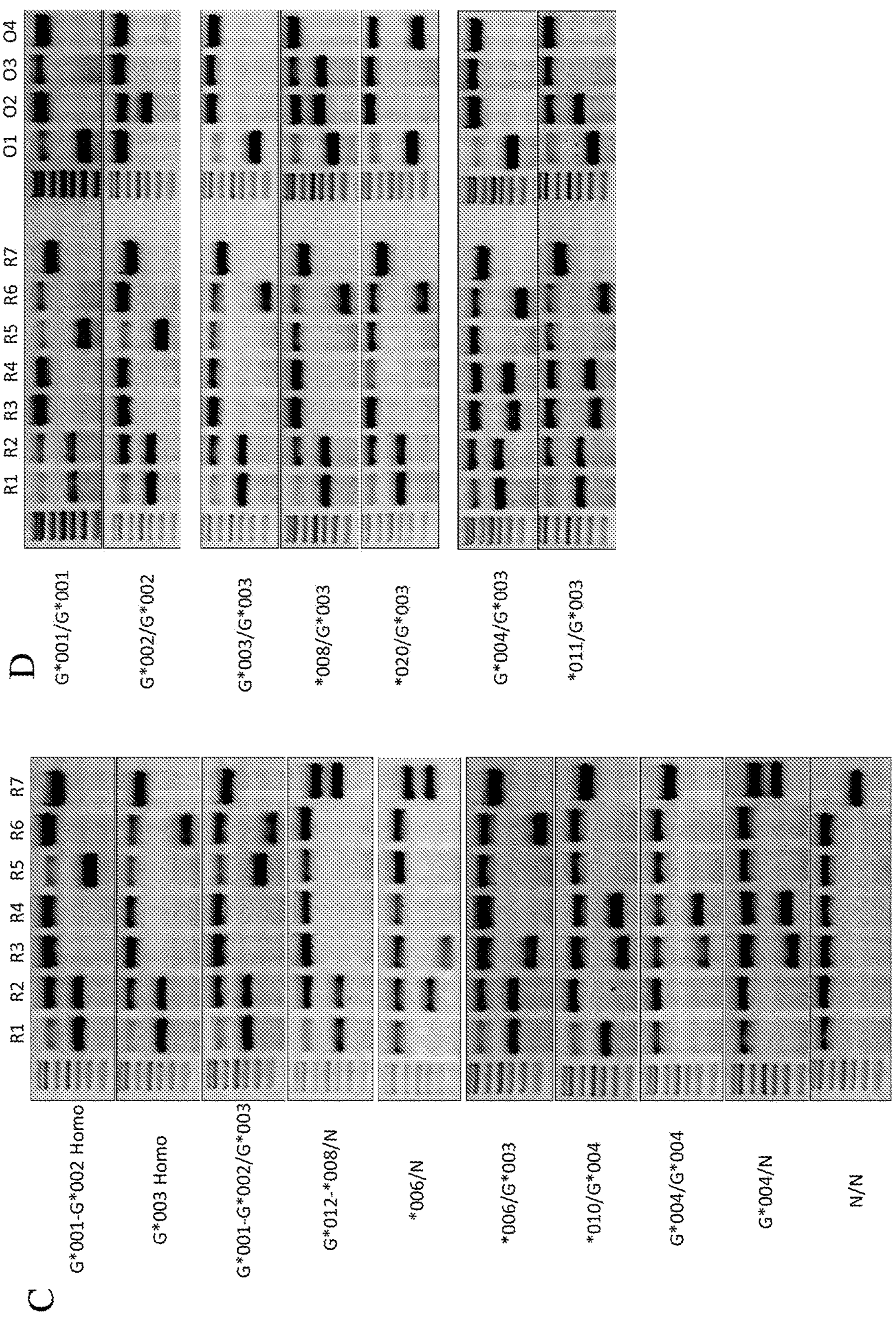
FIG. 2 shows KIR2DL1 allelic typing method.

PCR reaction conditions were optimized and validated using the ProFlex PCR system (Life Technologies). 50-100 ng of DNA was included in each 20 μL reaction, prepared with Taq polymerase (0.25 μL), dNTP (0.5 μL) and PCR buffer (2 μL) (Roche). Each primer is use at a final concentration of 5 μM. All the reactions contained the following PCR template: 95° C. 5 min, (95° C. 15s, 63° C. 20s, 72° C. 1 min) X40, 72° C. 7 min, except 2DL2 Reaction 4: 95° C. 5 min, (95° C. 15s, 63° C. 20s, 72° C. 2.5 min) X40, 72° C. 7 min. Control primers amplified a fragment of the APC gene. All the reactions had the specific primers and the control primers, except 2DL1 Reaction 7 and 2DL2 Reaction 4. PCR products were analyzed by gel electrophoresis on 1.5% agarose gels for 40 min at 125V. Control bands (813 bp) confirmed DNA quality. Specific product sizes ranged from 0.2-2.3 kb (FIG. 2).

Phenotypic Analysis by Flow Cytometry

Peripheral blood mononuclear cells (PBMCs) ($2\times10^5$ cells per well) were stained with the following antibodies: anti-CD56 (N901, ECD, Beckman Coulter), anti-CD3 (UCHT1, Brilliant Violet 650, BD Biosciences), anti-CD158a (143211, Fluorescein, R&D systems), anti-CD158b1/b2/j (CH-L, APC, BD Biosciences) and anti-CD158b2 (180701, PE, R&D systems). Dead cells were excluded by staining with DAPI. Natural killer (NK) cells were gated on the CD3-CD56dim. All FACS analyses were performed on an LSR Fortessa (BD Biosciences) and analyzed using FlowJo software (9.8.5, Treestar).

Example 1

Phylogenetic Studies

Molecular phylogenetic studies were performed by the alignment of amino acid sequences of human KIR2DL1, KIR2DL2, and KIR2DL3 followed by the construction of phylograms according to tree building method. KIR2DL1, KIR2DL2, and KIR2DL3 allele coding sequences were downloaded from the EMBL-EBI IPD KIR database. All alleles for which coding sequences are available were included in the alignment analyses. Finally, gene alignments were performed using Mac Vector Software. Relevant exon regions aligned for each KIR2DL1, KIR2DL2, and KIR2DL3 are shown in FIG. 1 (KIR2DL1), FIG. 3 (KIR2DL2) and FIG. 5 (KIR2DL3).

In the case of KIR2DL1 phylogenetic study, the inventors were able to identify six distinct groups (FIG. 1) based on amino acid and nucleotide alignment analysis. Yang et al. *Nat Rev Genet.* 2012 Mar. 28; 13(5):303-14. doi: 10.1038/nrg3186.

Figure 3:
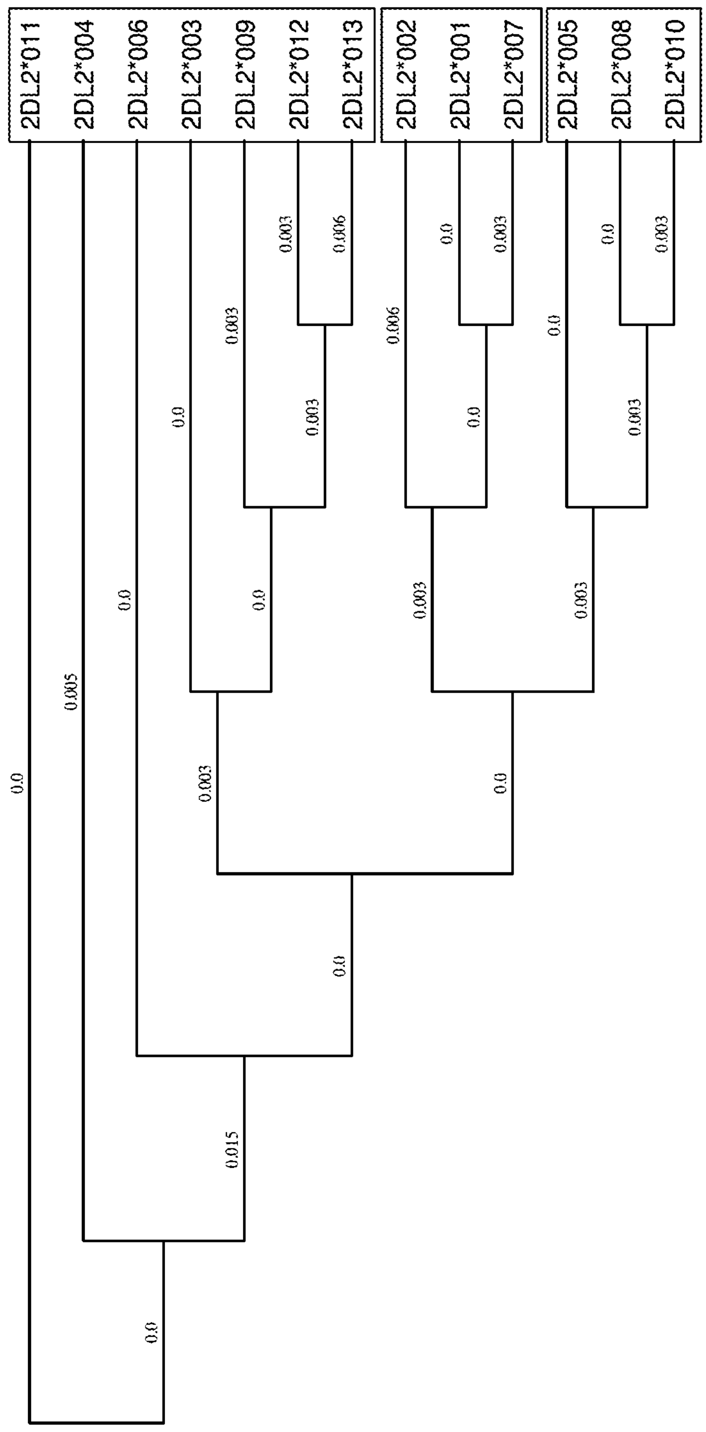
FIG. 3 is a schematic showing a phylogenetic study of KIR2DL2 alleles. All alleles-coding sequence of KIR2DL2 from the EMBL-EBI IPD KIR database sequences were included in the alignment analyses. Mature amino acid protein sequences of KIR2DL2 alleles were aligned and analyzed by tree building methods: neighbor joining (Uncorrected method, Best Tree) with MacVector. Three different allele groups were determined.
Figure 5:
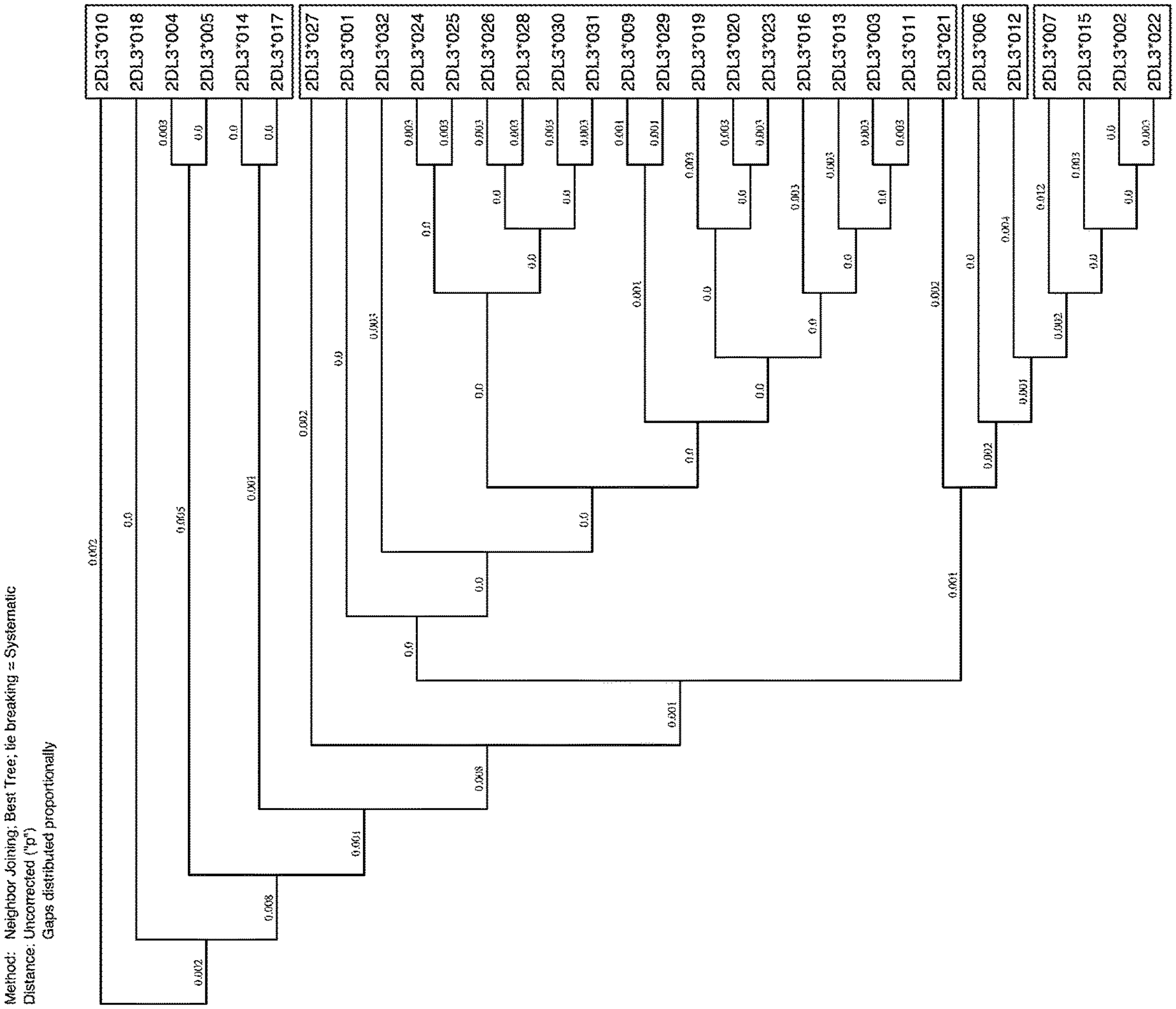
FIG. 5 is a schematic showing a phylogenetic study of KIR2DL3 alleles. All alleles-coding sequence of KIR2DL3 from the EMBL-EBI IPD KIR database sequences were included in the alignment analyses. Mature amino acid protein sequences of KIR2DL3 alleles were aligned and analyzed by tree building methods: neighbor joining (Uncorrected method, Best Tree) with MacVector. Four different groups were determined.

For KIR2DL2, phylogenetic study revealed three different groups of KIR2DL2 alleles (FIG. 3). Finally, for KIR2DL3, phylogenetic study led to identification of four different allele groups (FIG. 5).

Example 2

KIR2DL1 Allelic Typing Method

Next, the inventors performed an alignment of the amino acid sequences of the 26 known KIR2DL1 allelic variants (FIG. 2A). Here, the inventors looked at the frequency of allele representation within the cohort. Six PCR reactions separate the six subgroups identified by phylogenetic analysis. Four additional PCR reactions separate alleles within subgroups. The frequency of the alleles present in the learning cohort of 426 individuals and in the testing cohort of 220 individuals are shown in FIG. 2A. The group identification of the different alleles is indicated. In black bold font are the alleles tested by PCR, in grey Italic font are the non-tested alleles. To assist with the interpretation of the PCR results, the inventors have provided a table (FIG. 2B) that can be used as a KIR2DL1 PCR interpretation guide.

Next, the inventors designed the PCR primers specific to KIR2DL1 alleles, and carried out each of the six PCR reactions devised to define subgroups of KIR2DL1 (FIG. 2C). Additional reactions were designed and carried out in order to separate specific common alleles within the subgroups, as identified by phylogenetic study of the protein sequence (see 01, 02, 03, and 04 reactions in FIG. 2D). An additional reaction (FIGS. 2A, 2C and 2D, reaction 7 (R7) was developed to genotype the pseudo-genes KIR3DP1 (higher band) and KIR3DP1V (lower band) identifying the copy number of KIR2DL1. The alleles carrying KIR3DP1V are always negative for KIR2DL1. But if KIR3DP1V is negative, one copy may be may be KIR2DL1 negative so the KIR3DP1 test has to be performed too. So the PCR is multiplex. If only 3DP1+3DP1V− is present, you have 2 copies of 2DL1; if 3DP1+3DP1V+ is present, there is only one copy of 2DL. And if the 2DP1−3DP1V+ is present, then there is no copy of 2DL1. Each PCR reaction was multiplex and included control primers used to amplify a fragment of the APC gene (813 bp) for DNA quality control. The combination of the six (or seven if R7 is included in the analysis) PCR reactions allows for identification of a unique allelic KIR2DL1 groups. Note that primer sets, including both the forward and reverse primer for the main and optional reactions, which were used in the KIR2DL1 studies shown in FIG. 2, are listed in Table 1. While primers used for each reaction are identified in Table 1 (for KIR2DL1, DL2 and DL3), different primers can be designed for the same purpose, i.e., targeted to the same nucleotide and hybridizing to neighboring sequence segments. This is within the skill of the art given the information provided herein, not only for KIR2DL1 but also for DL2 and DL3 discussed below.

In FIGS. 2A (and 2B) solid grey blocks indicate a positive reaction, and white (empty) blocks indicate a negative reaction for a specific allele. It is evident that for example if reaction 1 for KIR2DL1 is positive, it reveals that the allele in question can belong to group 1 (*003), group 3 (*012), group 5 (*010) and group 6 (*002). If reaction 1 is negative for KIR2DL1, it means that allele in question may belong to group 2 (*006) or group 4 (*004). Note that groups 1,2,3, 4,5,6 are designations according to the order at which different groups appear in FIG. 2A. Following the same reasoning, it should be apparent that if reaction 2 for KIR2DL1 is positive, it indicates that the allele in question can belong to group 1 (*003), group 2 (*006), group 3 (*012), and group 6 (*002). If the reaction 2 is negative, it implies that the allele in question can belong to group 4 (*004) or group 5 (*010). Regarding reaction 3, if reaction 3 for KIR2DL1 is positive, a specific allele may belong to group 2 (*006) or group 4 (*004), while if the reaction 3 is negative, it indicates that a specific allele may belong to group 1 (*003), group 3 (*012), group 5 (*010), or group 6 (*002).

Furthermore, if reaction 4 is positive for KIR2DL1, it indicates that an allele may belong to group 4 (*004) or group 5 (*010). If the reaction 4 for KIR2DL1 is negative, it implies that an allele can belong to group 1 (*003), group 2 (*006), group 3 (*012), or group 6 (*002). A positive reaction 5 for KIR2DL1 would imply that an allele is a possibly a part of group 6 (*002). On the other hand, if reaction 5 is negative, it would indicate that an allele may belong to group 1 (*003), group 2 (*006), group 3 (*012), group 4 (*004), or group 5 (*010).

Finally, if reaction 6 is positive for KIR2DL1, it would imply that a specific allele possibly belongs to group 1 (*003), or if the reaction 6 is negative, it would indicate that a specific allele may belong to group 2 (*006), group 3 (*012), group 4 (*004), group 5 (*010), or group 6 (*002).

Example 3

KIR2DL2 Allelic Typing Method

Figure 4:
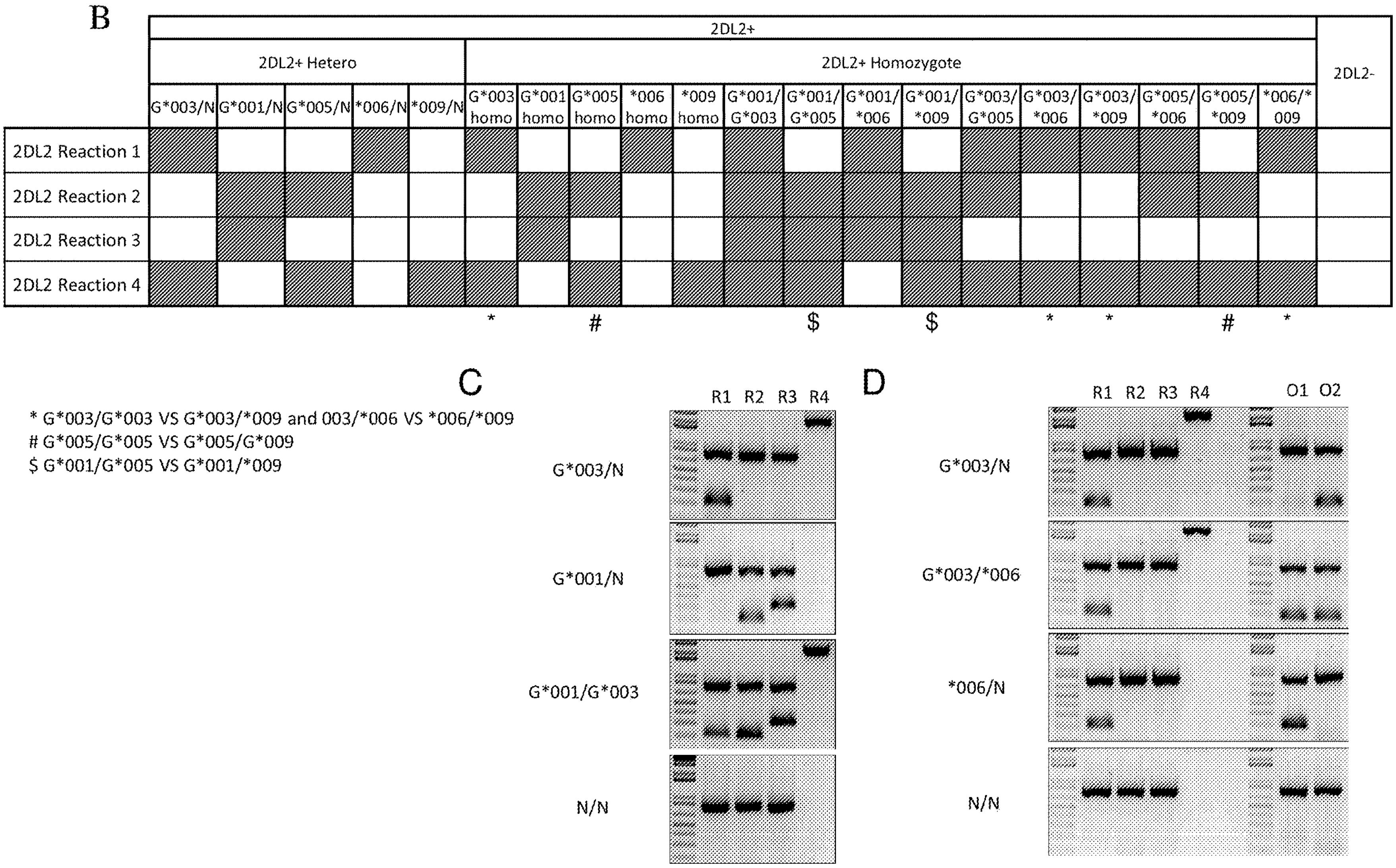
FIG. 4 shows KIR2DL2 allelic typing method.

The inventors aligned the amino acid sequences of the 13 known KIR2DL2 allelic variants (FIG. 4A), and determined the frequency of each allele within the cohort. Three different groups of KIR2DL2 alleles were identified, consistent with the findings of the KIR2DL2 phylogenetic study (FIG. 3). Based on the analysis, the inventors were able to design four PCR reactions capable of separating three KIR2DL2 allele subgroups. FIG. 4A shows the frequency of the alleles present in the learning cohort of 426 individuals and in the testing cohort of 220 individuals. Alleles tested by PCR appear in black bold font while non-tested alleles are shown in grey Italic font. Grey solid blocks shown in FIG. 4A correspond to a positive PCR reaction, while empty (white solid blocks) indicate a negative PCR reaction. To assist with the interpretation of the PCR results, the inventors have provided a table (FIG. 4B) that can be used as a KIR2DL1 PCR interpretation guide. In addition to four PCR reactions developed for classification of KIR2DL2 alleles, the inventors designed two optional reactions capable of differentiating between separate alleles within a subgroup. The inventors carried out four PCR reactions, as well as two optional reactions in order to differentiate KIR2DL2 alleles (FIGS. 4C and 4D).

In FIGS. 4A (and 4B), the solid grey blocks indicate a positive reaction, and white (empty) blocks indicate a negative reaction for a specific allele. It is evident that for example if reaction 1 for KIR2DL2 is positive, it indicates that an allele may belong to group 1 (*003), while if reaction 1 is negative, it implies that an allele may belong to group 2 (*001) or group 3 (*005). A positive reaction 2 for KIR2DL2 would indicate that an allele may belong to group 2 (*001) or group 3 (*005), while a negative reaction 2 for KIR2DL2 would indicate that an allele may be a part of group 1 (*003). Furthermore, a positive reaction 3 for KIR2DL2 would suggest that a specific allele may belong to group 2 (*001), while a negative reaction 3 for KIR2DL2 would imply that a specific allele may belong to group 1 (*003) or group 3 (*005). Finally, a positive reaction 4 for KIR2DL2 indicates that an allele may be a part of group 1 (*003) or group 3 (*005), while a negative reaction 4 for KIR2DL2 would suggest that an allele may belong to group 2 (*001).

Example 4

KIR2DL3 Allelic Typing Method

Figure 6:
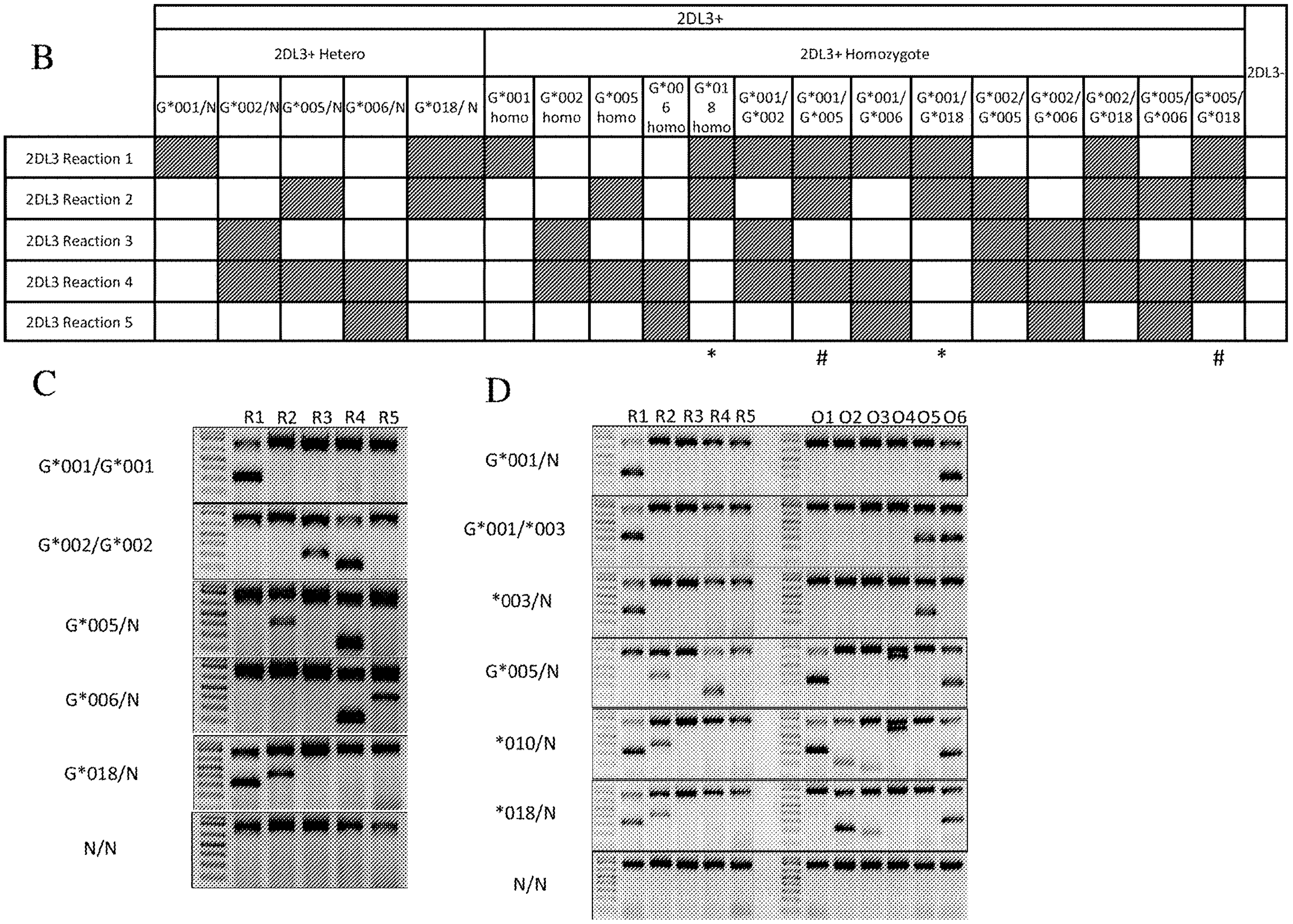
FIG. 6 shows the present KIR2DL3 allelic typing method.

In addition to developing PCR methods for distinguishing different allelic groups of KIR2DL1 and KIR2DL2, the inventors also studied KIR2DL3. As shown in FIG. 5, the inventors initially used phylogenetic studies to distinguish four different groups of KIR2DL3 alleles. FIG. 6A shows an alignment of the amino acid sequences of 32 known KIR2DL3 allelic variants, where frequency of each allele within the cohort was analyzed. Based on the analysis shown in FIG. 6A, the inventors were able to design five PCR reactions capable of separating three KIR2DL3 allele groups. Grey solid blocks correspond to a positive PCR reaction, while empty (white solid blocks) indicate a negative PCR reaction. FIG. 6B is a table providing KIR2DL1 PCR interpretation guide. PCR profiles marked by * or # are not resolvable with the 4 main reactions and require a higher resolution of genotyping, which can be accomplished using six optional reactions developed by the inventors (FIG. 6D). FIG. 6C shows gel electrophoresis of the five KIR2DL3 PCR reactions. Each PCR is multiplex and control primers amplify a fragment of the APC gene (813 bp) for DNA quality control. FIG. 6D is an electrophoresis gel of the eleven KIR2DL3 PCR reactions. Six optional PCR reactions are proposed to increase the resolution of the method. Using the optional reactions, the inventors were able to discriminate certain combinations of alleles that were not resolved initially.

With specific reference to FIG. 6A, the inventors have designed five PCR reactions that separate KIR2DL3 alleles into 4 groups (or 4 subgroups). From this Figure (as well as FIG. 4B) it is evident that for example if reaction 1 for KIR2DL3 is positive, it indicates that an allele may belong to group 1 (*001) or group 2 (*010, 017, 018). If reaction 1 is negative for KIR2DL3, it would suggest that an allele may belong to group 2 (*005), group 3 (*002), or group 4 (*006). A positive reaction 2 for KIR2DL3 would indicate that an allele may belong to group 2 (*005, *010, *017, *018), while a negative reaction 2 for KIR2DL3 would indicate that an allele may be apart of group 1 (*001), group 3 (*002), or group 4 (*006). A positive reaction 3 for KIR2DL3 would suggest that a specific allele may belong to group 3 (*002), while a negative reaction 3 for KIR2DL3 would imply that a specific allele may belong to group 1 (*001), group 2 (*005, *010, 017, 018), or group 4 (*006). Furthermore, a positive reaction 4 for KIR2DL3 would indicate that an allele may belong to group 2 (*005), group 3 (*002), or group 4 (*006). A negative reaction 4 for KIR2DL3 would imply that an allele may be a part of group 1 (*001) or group 2 (*010, 017, 018). Finally, a positive reaction 5 for KIR2DL3 indicates that a specific allele may be a part of group 4 (*006), while a negative reaction 5 for KIR2DL3 implies that a specific allele may be a part of group 1 (*001), group 2 (*005, 010, 017, 018), or group 3 (*002). No sample containing *004 was available to validate the prediction. As in the case of FIGS. 2A, 2B and 4A/4B, a grey band or square indicates a positive PCR result (amplification) whereas a white (empty) band or square indicates a negative result.

In addition to the above mentioned 5 reactions for KIR2DL3 alleles, the inventors have designed six optional PCR reactions for separating alleles within different KIR2DL3 allele groups. Note that groups 1,2,3, and 4 are designations according to order at which different groups appear in FIG. 6A. Resolution can thus be obtained as between specific combinations of G*001, N and *003 (e.g. G*001/N, G*001/*003, and *003/N). In addition, resolution can be obtained between *005/N versus *010/N versus *018/N.

Example 5

KIR2DL Allele Distribution Follows a Specific Pattern

Figure 7:
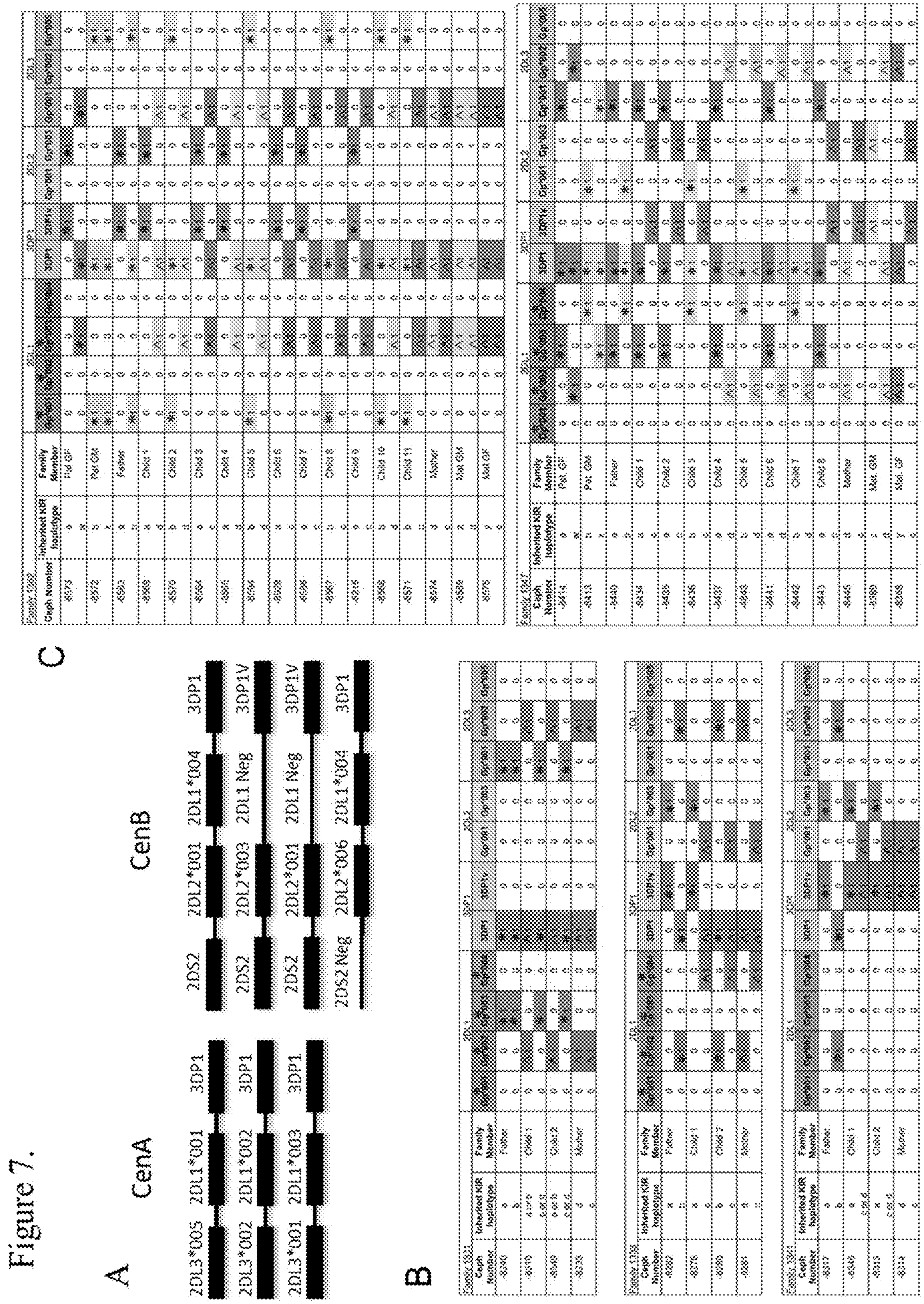
FIG. 7 shows that the KIR2DL alleles distribution follows a specific pattern.

Linkage disequilibrium (LD) analysis, which incorporates the effects of many past generations of recombination, can be instrumental in the final phases of gene localization (Feder J N et al. *Nat. Genet.* 13:399-408, 1996). In this Example, the inventors used LD analysis to measure the degree to which alleles at two loci are associated. Essentially, LD analysis provides non-random associations between alleles at two loci. Here, LD among KIR2DL1, KIR2DL2, KIR2DL3, KIR3DP1 alleles and KIR2DLS2 gene was calculated on a cohort of 220 donors. The seven most common combinations of alleles, three for the Centromeric A haplotype and four for the Centromeric B haplotype, were found to represent more than 95% of the donors in the cohort studied (FIG. 7A).

Immortalized lymphoblastoid cell lines from large three-generation families with known genotypes for many marker loci are available. These pedigrees, the Centre d"Etude du Polymorphisme Humain (CEPH) families, consist of samples collected from Utah, France, and Venezuela. FIG. 7B shows segregation analysis of the KIR2DL and KIR3DP1 alleles in CEPH families, where KIR2DL subtyping was completed for three parent child quartets and matched previous KIR2DL allele typing. As shown in FIG. 7C, KIR2DL subtype analysis of three generations of CEPH family individuals demonstrated Mendelian inheritance of alleles combinations established by the linkage disequilibrium study. In FIGS. 7B and 7C, paternal alleles are indicated by (*); maternal are indicated by (^).

Example 6

KIR2DL Allele Distribution Follows a Specific Pattern

Figure 8:
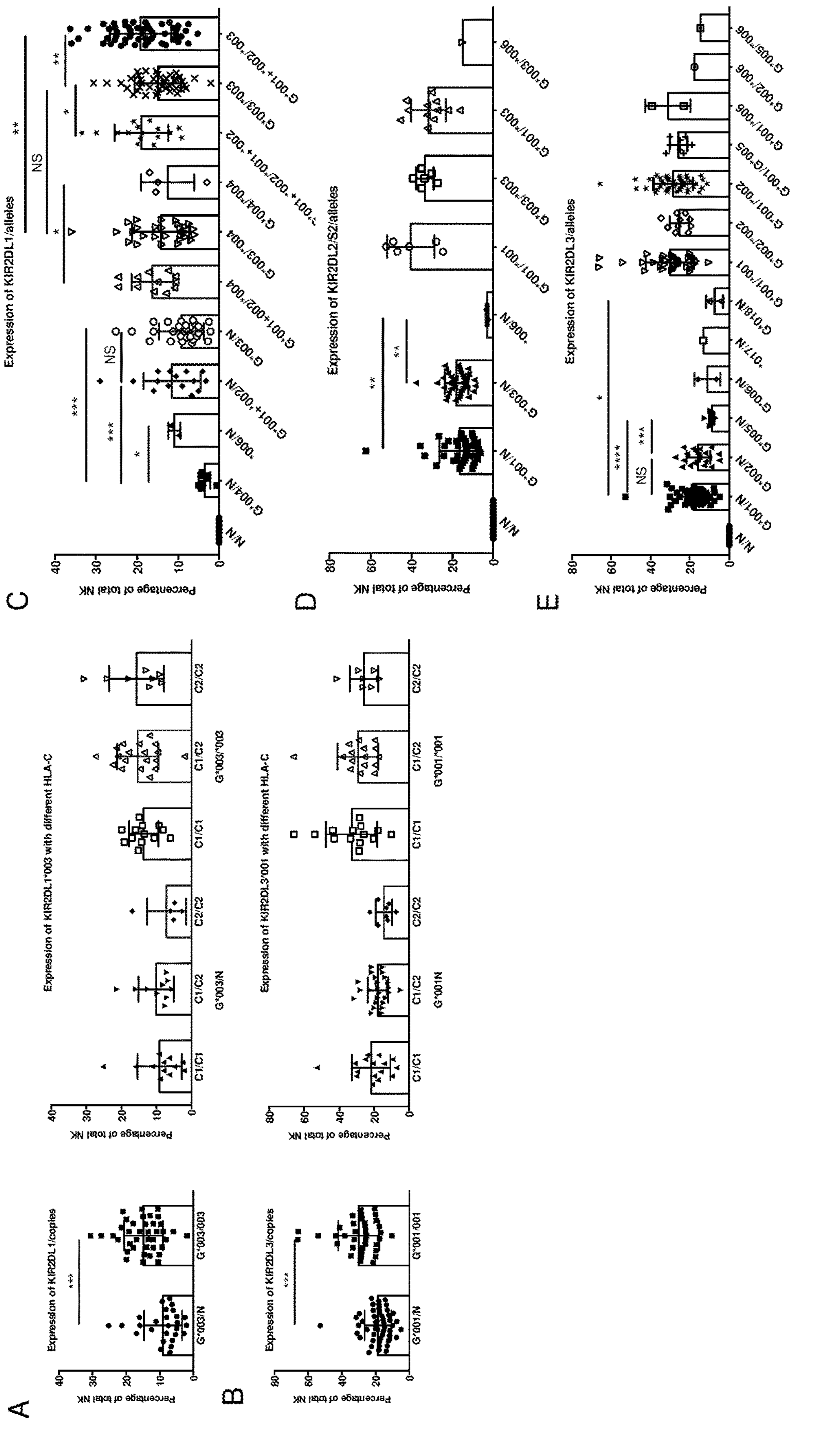
FIG. 8 shows differential expression frequency of KIR2DL alleles. KIR2DL expression frequency was measured by flow cytometry on total NK cells from healthy blood donors. All the donors having NKG2C+NK cells expansion were excluded from the study.

Expression frequency of different KIR2DL1, KIR2DL2, and KIR2DL3 alleles was evaluated. The expression frequency was measured by flow cytometry on total NK cells from healthy blood donors. All the donors having NKG2C+ NK cells expansion were excluded from the study. As shown in FIGS. 8A and 8B, expression frequencies of KIR2DL1 and KIR2DL3 correlate with the copy number of the alleles. Additionally, the inventors observed that KIR2DL1*004 has a lower frequency in comparison to *001 and *002 ($P<0.001$) and has an impact on the KIR2DL1 frequency when co-expressed with another KIR2DL1 allele. Furthermore, the KIR2DL1*003 allele has a lower frequency in comparison to *001 and *002 ($P<0.05$) (FIG. 8C). KIR2DL2*006 was found to have a lower frequency compared to *001/S2 or *003/S2 ($P<0.01$). This lower frequency is influenced by the absence of expression of KIR2DS2 on cells expressing KIR2DL2*006. As shown in FIG. 8D, KIR2DL2*006 has a lower expression frequency compared to *001/S2 or *003/S2 ($P<0.01$). This lower frequency is influenced by the non expression on KIR2DS2 on the alleles expressing KIR2DL2*006. In FIG. 8E, the inventors showed that KIR2DL3*005 has a lower expression frequency in comparison to *001 ($P<0.0001$) or *002 ($P<0.001$). Furthermore, KIR2DL3*018/*010 has a lower expression frequency in comparison to *001 ($P<0.05$).

Example 7

Differential KIR2DL Alleles Cell Surface Expression

Figure 9:
FIG. 9 shows differential cell surface expression for different KIR2DL alleles. KIR2DL cell surface expression was measured using flow cytometry on total NK cells from healthy blood donors.

Next, the inventors measured KIR2DL allele cell surface expression using flow cytometry on total NK cells from healthy blood donors. FIG. 9A shows that KIR2DL1*003 cell surface expression is impacted by the expression of its cognate ligand in both heterozygote and homozygote donors, decreasing the cell surface expression of the receptor. No effect of the copy number of the alleles was observed. As shown in FIG. 9B, KIR2DL1*002 achieved higher expression than *003 and *004. Moreover, KIR2DL1*003 achieved higher expression than *004 (FIG. 9B). The inventors observed that the higher the cell surface expression of the KIR2DL1 allele, the more important was the impact of the cognate ligand. Furthermore, KIR2DL3*001 cell surface expression did not change with the copy number of this allele and was not impacted significantly by expression of the cognate ligand (FIG. 9C). Mean fluorescence intensities (MFI) were measured using the mAb anti-KIR2DL3 (Clone 180701). KIR2DL3*005 exhibited higher expression on the cell surface in comparison to *001 and *002 ($P<0.0001$) (FIG. 9D), while KIR2DL3*018/*010 exhibited lower expression compared to *005 ($P<0.05$) (FIG. 9D). MFI were measured using the mAb anti KIR2DL2/L2/S2-(Clone CH-L). FIG. 9E is an example of flow cytometry illustrating the differential cell surface expression of the alleles KIR2DL3*005, KIR2DL3*010 and KIR2DL3*018. The difference in MFI between the different alleles was observed with two different Ab: anti-KIR2DL1/S1 (Clone EB6B) and anti-KIR2DL2/L2/S2 (Clone CH-L). It is anticipated that both the level of cell surface expression of an allele and the frequency of its expression may influence the determination of suitability of a hematopoietic cell donor.

Example 8

Impact of KIR2DL Alleles on Relapse of Acute Myeloid Leukemia (AML)Patients

Figure 10:
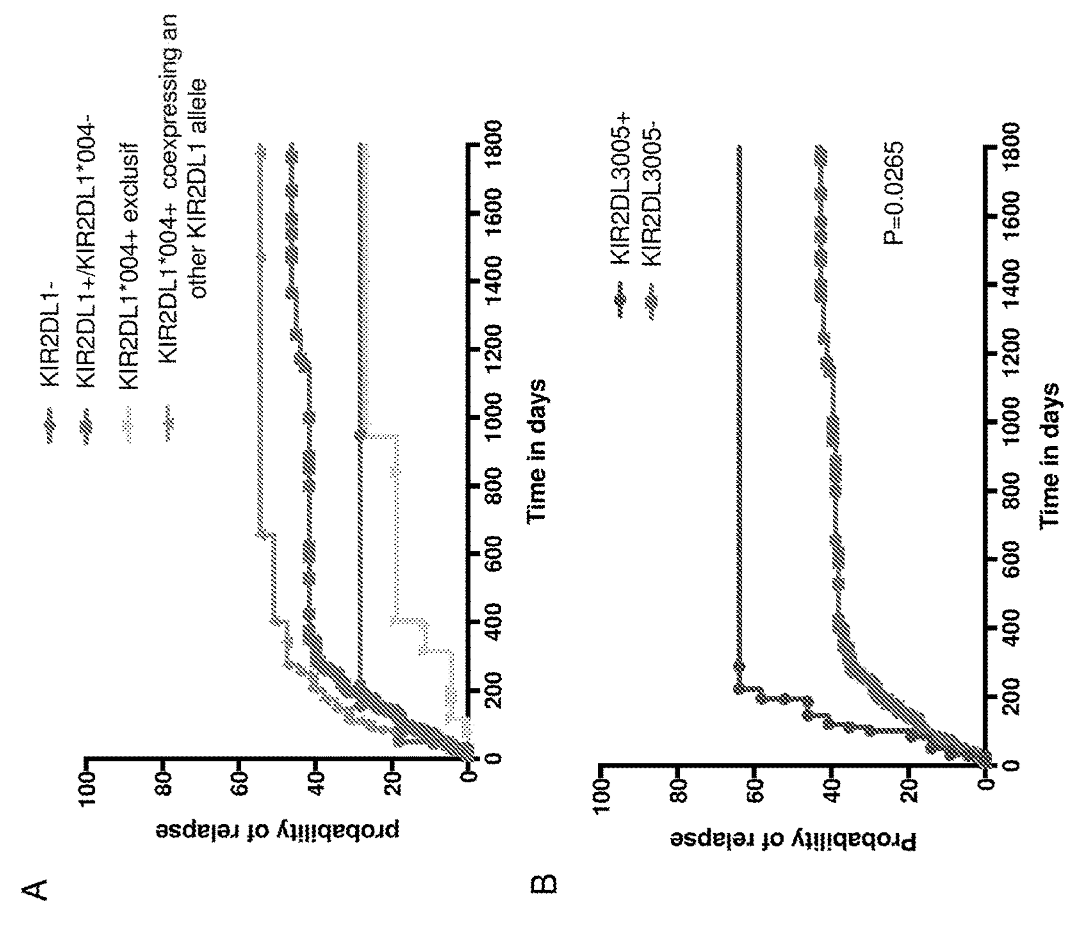
FIG. 10 shows the impact of KIR2DL alleles on relapse of AML patients.

In order to elucidate the impact of various KIR2DL alleles on relapse potential of patients diagnosed with AML, the inventors studied the impact of donor KIR2DL alleles in a cohort of 299 AML patients receiving a hematopoietic stem cell transplantation (HSCT) graft. The probability of relapse within the 1800 days post-transplant is shown in FIGS. 10A and 10B. As shown in FIG. 10A, patients receiving a transplant from KIR2DL1*004 exclusive positive donors (one or two copies of KIR2DL1*004 and no other alleles of KIR2DL1) have a lower probability of relapse in comparison to other groups. Additionally, it was observed that patients receiving a transplant from KIR2DL3*005 positive donor have a higher rate of relapse in comparison to patients receiving a transplant from a KIR2DL3*005 negative donors (FIG. 10B). The preliminary results described in FIG. 10 indicate that PCR reactions described in the present disclosure can be potentially used as one of the tools for screening donors for hematopoietic stem cell transplantation for KIR2DL alleles in order to decrease a patient's probability of relapse. The disclosure may also be useful for the design and production of cellular therapies for the treatment of leukemia and viral infection.

REFERENCES AND MISCELLANEOUS

All cited references are incorporated by reference in their entirety for all purposes. The examples disclosed herein are illustrative and not limiting in nature. Details disclosed with respect to the methods described herein included in one example or embodiment may be applied to other examples and embodiments. Any aspect of the present disclosure that has been described herein may be disclaimed.

SEQUENCES OF FULL KIR2DL1, KIR2DL2, AND KIR2DL3 ALLELES obtained from www.ebi.ac.uk/ipd/kir/alleles.html KIR2DL1*00301 Sequences:

Protein Sequence:
MSLLVVSMACVGFFLLQGAWPHEGVHRKPSLLAHPGRLVKSEETVILQCWS
DVMFEHFLLHREGMFNDTLRLIGEHHDGVSKANFSISRMTQDLAGTYRCYG
SVTHSPYQVSAPSDPLDIVIIGLYEKPSLSAQLGPTVLAGENVTLSCSSRS
SYDMYHLSREGEAHERRLPAGPKVNGTFQADFPLGPATHGGTYRCFGSFHD
SPYEWSKSSDPLLVSVTGNPSNSWPSPTEPSSKTGNPRHLHILIGTSVVII
LFILLFFLLHRWCSNKKNAAVMDQESAGNRTANSEDSDEQDPQEVTYTQLN
HCVETQRKITRPSQRPKTPPTDIIVYTELPNAESRSKVVSCP
(SEQ ID NO: 60)

Nucleotide Sequence:
ATGTCGCTCTTGGTCGTCAGCATGGCGTGTGTTGGGTTCTTCTTGCTGCAG
GGGGCCTGGCCACATGAGGGAGTCCACAGAAAACCTTCCCTCCTGGCCCAC
CCAGGTCGCCTGGTGAAATCAGAAGAGACAGTCATCCTGCAGTGTTGGTCA
GATGTCATGTTTGAACACTTCCTTCTGCACAGAGAGGGGATGTTTAACGAC
ACTTTGCGCCTCATTGGAGAACACCATGATGGGGTCTCCAAGGCCAACTTC
TCCATCAGTCGCATGACGCAAGACCTGGCAGGGACCTACAGATGCTACGGT
TCTGTTACTCACTCCCCCTATCAGGTGTCAGCTCCCAGTGACCCTCTGGAC
ATCGTGATCATAGGTCTATATGAGAAACCTTCTCTCTCAGCCCAGCTGGGC
CCCACGGTTCTGGCAGGAGAGAATGTGACCTTGTCCTGCAGCTCCCGGAGC
TCCTATGACATGTACCATCTATCCAGGGAAGGGGAGGCCCATGAACGTAGG
CTCCCTGCAGGGCCCAAGGTCAACGGAACATTCCAGGCTGACTTTCCTCTG
GGCCCTGCCACCCACGGAGGGACCTACAGATGCTTCGGCTCTTTCCATGAC
TCTCCATACGAGTGGTCAAAGTCAAGTGACCCACTGCTTGTTTCTGTCACA
GGAAACCCTTCAAATAGTTGGCCTTCACCCACTGAACCAAGCTCCAAAACG
GGTAACCCCCGACACCTGCACATTCTGATTGGGACCTCAGTGGTCATCATC
CTCTTCATCCTCCTCTTCTTTCTCCTTCATCGCTGGTGCTCCAACAAAAAA
AATGCTGCGGTAATGGACCAAGAGTCTGCAGGAAACAGAACAGCGAATAGC
GAGGACTCTGATGAACAAGACCCTCAGGAGGTGACATACACACAGTTGAAT
CACTGCGTTTTCACACAGAGAAAAATCACTCGCCCTTCTCAGAGGCCCAAG
ACACCCCCAACAGATATCATCGTGTACACGGAACTTCCAAATGCTGAGTCC
AGATCCAAAGTTGTCTCCTGCCCATGA
(SEQ ID NO: 61)

KIR2DL2*0030101 Sequences

Protein Sequence:
MSLMVVSMACVGFFLLQGAWPHEGVHRKPSLLAHPGRLVKSEETVILQCWS
DVRFEHFLLHREGKFKDTLHLIGEHHDGVSKANFSIGPMNIQDLAGTYRCY
GSVTHSPYQLSAPSDPLDIVITGLYEKPSLSAQPGPTVLAGESVTLSCSSR
SSYDMYHLSREGEAHECRFSAGPKVNGTFQADFPLGPATHGGTYRCFGSFR
DSPYEWSNSSDPLLVSVTGNPSNSWPSPTEPSSKTGNPRHLHILIGTSVVI
ILFILLFFLLHRWCSNKKNAAVMDQESAGNRTANSEDSDEQDPQEVTYTQL
NHCVFTQRKITRPSQRPKTPPTDIIVYTELPNAESRSKVVSCP
(SEQ ID NO: 62)

Nucleotide Sequence:
ATGTCGCTCATGGTCGTCAGCATGGCGTGTGTTGGGTTCTTCTTGCTGCAG
GGGGCCTGGCCACATGAGGGAGTCCACAGAAAACCTTCCCTCCTGGCCCAC -continued SEQUENCES OF FULL KIR2DL1, KIR2DL2, AND KIR2DL3 ALLELES obtained from www.ebi.ac.uk/ipd/kir/alleles.html CCAGGTCGCCTGGTGAAATCAGAAGAGACAGTCATCCTGCAATGTTGGTCA
GATGTCAGGTTTGAGCACTTCCTTCTGCACAGAGAAGGGAAGTTTAAGGAC
ACTTTGCACCTCATTGGAGAGCACCATGATGGGGTCTCCAAAGCCAACTTC
TCCATCGGTCCCATGATGCAAGACCTTGCAGGGACCTACAGATGCTACGGT
TCTGTTACTCACTCCCCCTATCAGTTGTCAGCTCCCAGTGACCCTCTGGAC
ATCGTCATCACAGGTCTATATGAGAAACCTTCTCTCTCAGCCCAGCCGGGC
CCCACGGTTCTGGCAGGAGAGAGCGTGACCTTGTCCTGCAGCTCCCGGAGC
TCCTATGACATGTACCATCTATCCAGGGAGGGGGAGGCCCATGAATGTAGG
TTCTCTGCAGGGCCCAAGGTCAACGGAACATTCCAGGCCGACTTTCCTCTG
GGCCCTGCCACCCACGGAGGAACCTACAGATGCTTCGGCTCTTTCCGTGAC
TCTCCATACGAGTGGTCAAACTCGAGTGACCCACTGCTTGTTTCTGTCACA
GGAAACCCTTCAAATAGTTGGCCTTCACCCACTGAACCAAGCTCTAAAACC
GGTAACCCCCGACACCTGCACATTCTGATTGGGACCTCAGTGGTCATCATC
CTCTTCATCCTCCTCTTCTTTCTCCTTCATCGCTGGTGCTCCAACAAAAAA
AATGCTGCGGTAATGGACCAAGAGTCTGCAGGGAACAGAACAGCGAATAGC
GAGGACTCTGATGAACAAGACCCTCAGGAGGTGACATACACACAGTTGAAT
CACTGCGTTTTCACACAGAGAAAAATCACTCGCCCTTCTCAGAGGCCCAAG
ACACCCCCAACAGATATCATCGTGTACACGGAACTTCCAAATGCTGAGTCC
AGATCCAAAGTTGTCTCCTGCCCATGA
(SEQ ID NO: 63)

KIR2DL3*0010101 Sequences

Protein Sequence:
MSLMVVSMVCVGFELLQGAWPHEGVHRKPSLLAHPGPLVKSEETVILQCWS
DVRFQHFLLHREGKFKDTLHLIGEHHDGVSKANFSIGPMMQDLAGTYRCYG
SVTHSPYQLSAPSDPLDIVITGLYEKPSLSAQPGPTVLAGESVTLSCSSRS
SYDMYHLSREGEAHERRFSAGPKVNGTFQADFPLGPATHGGTYRCFGSFRD
SPYEWSNSSDPLLVSVTGNPSNSWPSPTEPSSETGNPRHLHVLIGTSVVII
LFILLLFFLLHRWCCNKKNAVVMDQEPAGNRTVNREDSDEQDPQEVTYAQL
NHCVETQRKITRPSQRPKTPPTDIIVYTELPNAEP
(SEQ ID NO: 64)

Nucleotide Sequence:
ATGTCGCTCATGGTCGTCAGCATGGTGTGTGTTGGGTTCTTCTTGCTGCAG
GGGGCCTGGCCACATGAGGGAGTCCACAGAAAACCTTCCCTCCTGGCCCAC
CCAGGTCCCCTGGTGAAATCAGAAGAGACAGTCATCCTGCAATGTTGGTCA
GATGTCAGGTTTCAGCACTTCCTTCTGCACAGAGAAGGGAAGTTTAAGGAC
ACTTTGCACCTCATTGGAGAGCACCATGATGGGGTCTCCAAGGCCAACTTC
TCCATCGGTCCCATGATGCAAGACCTTGCAGGGACCTACAGATGCTACGGT
TCTGTTACTCACTCCCCCTATCAGTTGTCAGCTCCCAGTGACCCTCTGGAC
ATCGTCATCACAGGTCTATATGAGAAACCTTCTCTCTCAGCCCAGCCGGGC
CCCACGGTTCTGGCAGGAGAGAGCGTGACCTTGTCCTGCAGCTCCCGGAGC
TCCTATGACATGTACCATCTATCCAGGGAGGGGGAGGCCCATGAACGTAGG
TTCTCTGCAGGGCCCAAGGTCAACGGAACATTCCAGGCCGACTTTCCTCTG
GGCCCTGCCACCCACGGAGGAACCTACAGATGCTTCGGCTCTTTCCGTGAC
TCTCCATACGAGTGGTCAAACTCGAGTGACCCACTGCTTGTTTCTGTCACA
GGAAACCCTTCAAATAGTTGGCCTTCACCCACTGAACCAAGCTCCGAAACC
GGTAACCCCAGACACCTGCATGTTCTGATTGGGACCTCAGTGGTCATCATC
CTCTTCATCCTCCTCCTCTTCTTTCTCCTTCATCGCTGGTGCTGCAACAAA
AAAAATGCTGTTGTAATGGACCAAGAGCCTGCAGGGAACAGAACAGTGAAC
AGGGAGGACTCTGATGAACAAGACCCTCAGGAGGTGACATATGCACAGTTG
AATCACTGCGTTTTCACACAGAGAAAAATCACTCGCCCTTCTCAGAGGCCC
AAGACACCCCCAACAGATATCATCGTGTACACGGAACTTCCAAATGCTGAG
CCCTGA
(SEQ ID NO: 65)

What is claimed is:

1. A method for determining the allelic group of KIR2DL1 alleles in a subject, comprising:

(a) performing PCR reactions in a genomic DNA sample obtained from the subject with (i) a first reverse primer that comprises at least 10 nucleotides that are identical to SEQ ID NO: 4 and binds specifically to a region of KIR2DL1 alleles comprising nucleotide 4011 of SEQ ID NO: 66 and a first forward primer that comprises at least 10 nucleotides that are identical to SEQ ID NO: 3 and binds specifically to a region of KIR2DL1 alleles comprising nucleotide 3680 of SEQ ID NO: 66 that are configured to generate a first amplification product, if present;

(ii) a second reverse primer that comprises at least 10 nucleotides that are identical to SEQ ID NO: 6 and binds specifically to a region of KIR2DL1 alleles comprising nucleotide 5820 of SEQ ID NO: 66 and a second forward primer that comprises at least 10 nucleotides that are identical to SEQ ID NO: 5 and binds specifically to a region of KIR2DL1 alleles comprising nucleotide 5499 of SEQ ID NO: 66 that are configured to generate a second amplification product, if present;

(iii) a third reverse primer that comprises at least 10 nucleotides that are identical to SEQ ID NO: 8 and binds specifically to a region of KIR2DL1 alleles comprising nucleotide 13609 of SEQ ID NO: 66 and a third forward primer that comprises at least 10 nucleotides that are identical to SEQ ID NO: 7 and binds specifically to a region of KIR2DL1 alleles comprising nucleotide 13420 of SEQ ID NO: 66 that are configured to generate a third amplification product, if present;

(iv) a fourth reverse primer that comprises at least 10 nucleotides that are identical to SEQ ID NO: 10 and binds specifically to a region of KIR2DL1 alleles comprising nucleotide 5735 of SEQ ID NO: 66 and a fourth forward primer that comprises at least 10 nucleotides that are identical to SEQ ID NO: 9 and binds specifically to a region of KIR2DL1 alleles comprising nucleotide 5499 of SEQ ID NO: 66 that are configured to generate a fourth amplification product, if present; and (v) a fifth reverse primer that comprises at least 10 nucleotides that are identical to SEQ ID NO: 12 and binds specifically to a region of KIR2DL1 alleles comprising nucleotide 4011 of SEQ ID NO: 66 and a fifth forward primer that comprises at least 10 nucleotides that are identical to SEQ ID NO: 11 and binds specifically to a region of KIR2DL1 alleles comprising nucleotide 3790 of SEQ ID NO: 66 that are configured to generate a fifth amplification product, if present; and (vi) a sixth reverse primer that comprises at least 10 nucleotides that are identical to SEQ ID NO: 14 and binds specifically to a region of KIR2DL1 alleles comprising nucleotide 5761 of SEQ ID NO: 66 and a sixth forward primer that comprises at least 10 nucleotides that are identical to SEQ ID NO: 13 and binds specifically to a region of KIR2DL1 alleles comprising nucleotide 5616 of SEQ ID NO: 66 that are configured to generate a sixth amplification product, if present; and (b) determining one or more allelic groups of KIR2DL1 alleles present in the subject based on detection of the first, second, third, fourth, fifth, and sixth amplification products from the PCR reactions, wherein the one or more allelic groups of KIR2DL1 alleles are selected from among group 1 (*003), group 2 (*006), group 3 (*012), group 4 (*004), group 5 (*010) and group 6 (*002).

2. The method of claim 1, comprising determining the presence of a group 4 (*004) allelic group of KIR2DL1 alleles in the subject when the third and fourth amplification products are detected in the PCR reactions.

3. The method of claim 1, comprising determining the presence of a *002, *021, *022 or *001 KIR2DL1 allele in the subject when the fifth amplification product, and optionally the first or second amplification products, are detected in the PCR reactions.

4. The method of claim 1, comprising determining the presence of a group 2 (*006) allelic group of KIR2DL1 alleles in the subject when the second and third amplification products are detected in the PCR reactions.

5. The method of claim 1, comprising determining the presence of a group 1 (*003) allelic group of KIR2DL1 alleles in the subject when the sixth amplification product, and optionally the first or second amplification products, are detected in the PCR reactions.

6. The method of claim 1, comprising determining the presence of a group 5 (*010) allelic group of KIR2DL1 alleles in the subject when the first and fourth amplification products are detected in the PCR reactions.

7. The method of claim 1, comprising determining the presence of a group 3 (*012) allelic group of KIR2DL1 alleles in the subject when the first or second amplification products are detected in the PCR reactions, and the fifth and sixth amplification products are not detected in the PCR reactions.

8. The method of claim 5, further comprising:

performing an additional PCR reaction using a forward primer that comprises at least 10 nucleotides that are identical to SEQ ID NO: 24 and specifically binds to a region of KIR2DL1 alleles including nucleotide 3942, and a reverse primer that comprises at least 10 nucleotides that are identical to SEQ ID NO: 25 and specifically binds to a region of KIR2DL1 alleles including nucleotide 4110 of SEQ ID NO: 66 that are configured to generate an additional amplification product, if present; and determining the presence of the *020 KIR2DL1 allele in the subject, when the additional amplification product is detected in the additional PCR reaction.

9. The method of claim 2, further comprising:

performing an additional PCR reaction using a forward primer that comprises at least 10 nucleotides that are identical to SEQ ID NO: 20 and specifically binds to a region of KIR2DL1 alleles including nucleotide 281 of SEQ ID NO: 66, and a reverse primer that comprises at least 10 nucleotides that are identical to SEQ ID NO: 21 and specifically binds to a region of KIR2DL1 alleles including nucleotide 620 of SEQ ID NO: 66 that are configured to generate an additional amplification product, if present; and determining the presence of the *011 KIR2DL1 allele in the subject, when the additional amplification product is detected in the additional PCR reaction.

10. The method of claim 3, further comprising:

performing an additional PCR reaction using a forward primer that comprises at least 10 nucleotides that are identical to SEQ ID NO: 18 and specifically binds to a region of KIR2DL1 alleles including nucleotide 71 of SEQ ID NO: 66 and a reverse primer that comprises at least 10 nucleotides that are identical to SEQ ID NO: 19 and specifically binds to a region of KIR2DL1 alleles including nucleotide 281 of SEQ ID NO: 66 that are configured to generate an additional amplification product, if present; and determining the presence of the *022 or *001 KIR2DL1 allele in the subject when the additional amplification product is detected in the additional PCR reaction or determining the presence of the *002, or *021 KIR2DL1 allele in the subject when the additional amplification product is not detected in the additional PCR reaction.

11. The method of claim 1, further comprising:

performing additional PCR reactions using (i) a first additional forward primer that comprises at least 10 nucleotides that are identical to SEQ ID NO: 20 and specifically binds to a region of KIR2DL1 alleles including nucleotide 281 of SEQ ID NO: 66, and a first additional reverse primer that comprises at least 10 nucleotides that are identical to SEQ ID NO: 21 and specifically binds to a region of KIR2DL1 alleles including nucleotide 620 of SEQ ID NO: 66 that are configured to generate a first additional amplification product, if present; and (ii) a second additional forward primer that comprises at least 10 nucleotides that are identical to SEQ ID NO: 22 and specifically binds to a region of KIR2DL1 alleles including nucleotide 3787 of SEQ ID NO: 66, and a second additional reverse primer that comprises at least 10 nucleotides that are identical to SEQ ID NO: 23 and specifically binds to a region of KIR2DL1 alleles including nucleotide 4110 of SEQ ID NO: 66 that are configured to generate a second additional amplification product, if present; and determining the presence of the *008 KIR2DL1 allele in the subject, when the first and second additional amplification products and the first or second amplification products are detected in the additional PCR reaction.

* * * * *

SEQUENCE LISTING

<160> NUMBER OF SEQ ID NOS: 68

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1
ccaagcccaa ccttaagaag aaaattggag                                    30

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ccaaacccac ggtacgcatg ggaacactgc                                    30

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
agagataaga caccaggaag gggaagcccg                                    30

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tgtccagagg gtcactggga gctgactc                                      28

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gagagagaga gagagagagc attaggtcat agta                               34

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tgactttgac cactcgtatg gagagtctt                                     29

<210> SEQ ID NO 7
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
atcctcttca tcctcctctt ctttctcctt cact                               34

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
cagttcagaa tcaggcaacg gtctgtgaat 30

<210> SEQ ID NO 9
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
gagagagaga gagagagagc attaggtcat agga 34

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
tggcctggaa tgttccgttg accttgct 28

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
aaccttccct cctggcccac ccaggtac 28

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
gatgtccaga gggtcactgg gagctgacgc 30

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
atatgagaaa ccttctctct cagcccagtt 30

-continued

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 14
gtgggtggca gggcccagag gaaagtaa 28

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 15
acgtgttgtg agttggtcat agtga 25

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence: Synthetic
primer

<400> SEQUENCE: 16
aagtggaaat gggagaatct tctgac 26

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 17
gccctctgac ctgtgaccat gatc 24

<210> SEQ ID NO 18
<211> LENGTH: 39
<212> TYPE: DNA
<213> ORGANISM: Artificial Sequence
<220> FEATURE:
<223> OTHER INFORMATION: Description of Artificial Sequence: Synthetic
primer

<400> SEQUENCE: 18
gttggtcata gtgaaggaca ctaggtgtca aattctatc 39

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: Synthetic
primer

<400> SEQUENCE: 19
tcaccaacac acgccatgct gacgtc 26

-continued

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
ctccggcagc accatgtcgc tcttat 26

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
ccgtaactcc acctccaggc ccatta 26

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
aaaccttccc tcctggccca cccaaa 26

<210> SEQ ID NO 23
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
cttccttaca gccacctggg tctccagt 28

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
gggtctccaa ggccaacttc tccatgg 27

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
cttccttaca gccacctggg tctccact 28

<210> SEQ ID NO 26

-continued

<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 26
tatccaggga gggggaggcc catgatt 27

<210> SEQ ID NO 27
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 27
tgagacagat atggggtttc ctcaccag 28

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 28
tatccaggga gggggaggcc catgatt 27

<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 29
gagacagata tggggtttcc tcaccca 27

<210> SEQ ID NO 30
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 30
acagatgctg cggtaatgga ccaagatt 28

<210> SEQ ID NO 31
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 31
atctggactc agcatttgga agttcccc 28

<210> SEQ ID NO 32
<211> LENGTH: 29

-continued

<212> TYPE: DNA
<213> ORGANISM: Artificial Sequence
<220> FEATURE:
<223> OTHER INFORMATION: Description of Artificial Sequence: Synthetic
primer

<400> SEQUENCE: 32
ctacttccaa tcacctgtgg agattcatg 29

<210> SEQ ID NO 33
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 33
atctggactc agcatttgga agttcctt 28

<210> SEQ ID NO 34
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 34
aaccttccct cctggcccac ccaggttc 28

<210> SEQ ID NO 35
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 35
catcatggga ccgatggaga agttggtt 28

<210> SEQ ID NO 36
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 36
aaccttccct cctggcccac ccaggtag 28

<210> SEQ ID NO 37
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 37
catcatggga ccgatggaga agttgggt 28

<210> SEQ ID NO 38
<211> LENGTH: 28
<212> TYPE: DNA

<213> ORGANISM: Artificial Sequence
<220> FEATURE:
<223> OTHER INFORMATION: Description of Artificial Sequence: Synthetic
primer

<400> SEQUENCE: 38
atgaaatgag ggcccagaag tgccctgt 28

<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 39
ggtgtcttgg gcctctgaga aggac 25

<210> SEQ ID NO 40
<211> LENGTH: 32
<212> TYPE: DNA
<213> ORGANISM: Artificial Sequence
<220> FEATURE:
<223> OTHER INFORMATION: Description of Artificial Sequence: Synthetic
primer

<400> SEQUENCE: 40
cacagagaag ggaagtttaa ggacactttg tg 32

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 41
tgtatggccc ctgtgtctgt ccttt 25

<210> SEQ ID NO 42
<211> LENGTH: 38
<212> TYPE: DNA
<213> ORGANISM: Artificial Sequence
<220> FEATURE:
<223> OTHER INFORMATION: Description of Artificial Sequence: Synthetic
primer

<400> SEQUENCE: 42
ctgtctcatg ttctaggaaa cccttcaaat agttgggt 38

<210> SEQ ID NO 43
<211> LENGTH: 43
<212> TYPE: DNA
<213> ORGANISM: Artificial Sequence
<220> FEATURE:
<223> OTHER INFORMATION: Description of Artificial Sequence: Synthetic
primer

<400> SEQUENCE: 43
gaaggatgtc agattggcaa tcattcttct agcttgtagg aaa 43

<210> SEQ ID NO 44
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 44
gcctgcaggg aacagaacag tgaacaag 28

<210> SEQ ID NO 45
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 45
ggtgtcttgg gcctctgaga aggct 25

<210> SEQ ID NO 46
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 46
cctcattgga gagcaccatg atggggct 28

<210> SEQ ID NO 47
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
cctctctctg ggacatgtct gtctgtctgt ctgt 34

<210> SEQ ID NO 48
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 48
taggagtcca cagaaaacct tccctcgg 28

<210> SEQ ID NO 49
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 49
gaatgtccgg acactctcac ctgtgacg 28

<210> SEQ ID NO 50
<211> LENGTH: 30
<212> TYPE: DNA
<213> ORGANISM: Artificial Sequence
<220> FEATURE:

<223> OTHER INFORMATION: Description of Artificial Sequence: Synthetic
primer

<400> SEQUENCE: 50
ccctccatct gggtgcttgt cctaaaggcg 30

<210> SEQ ID NO 51
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 51
gcgatgaagg agaaagaaga ggaggaggtc 30

<210> SEQ ID NO 52
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 52
tgaacaagac cctcaggagg tgacattt 28

<210> SEQ ID NO 53
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 53
tcatgggcag gagacaactt tggatat 27

<210> SEQ ID NO 54
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 54
tcctgcaatg ttggtcagat gtcaggttcg 30

<210> SEQ ID NO 55
<211> LENGTH: 26
<212> TYPE: DNA
<213> ORGANISM: Artificial Sequence
<220> FEATURE:
<223> OTHER INFORMATION: Description of Artificial Sequence: Synthetic
primer

<400> SEQUENCE: 55
aggccacagg gcccaactca ggtcgt 26

<210> SEQ ID NO 56
<211> LENGTH: 28
<212> TYPE: DNA
<213> ORGANISM: Artificial Sequence
<220> FEATURE:
<223> OTHER INFORMATION: Description of Artificial Sequence: Synthetic -continued primer

<400> SEQUENCE: 56
atgaaatgag ggcccagaag tgccctgt 28

<210> SEQ ID NO 57
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 57
ctctgtgtga aaacgcagtg attcaactgt tt 32

<210> SEQ ID NO 58
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 58
atgaaatgag ggcccagaag tgccctgt 28

<210> SEQ ID NO 59
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 59
ctctgtgtga aaacgcagtg attcaactgt tc 32

<210> SEQ ID NO 60
<211> LENGTH: 348
<212> TYPE: PRT
<213> ORGANISM: Homo sapiens

<400> SEQUENCE: 60

```
Met Ser Leu Leu Val Val Ser Met Ala Cys Val Gly Phe Phe Leu Leu
1               5                   10                  15

Gln Gly Ala Trp Pro His Glu Gly Val His Arg Lys Pro Ser Leu Leu
            20                  25                  30

Ala His Pro Gly Arg Leu Val Lys Ser Glu Glu Thr Val Ile Leu Gln
        35                  40                  45

Cys Trp Ser Asp Val Met Phe Glu His Phe Leu Leu His Arg Glu Gly
    50                  55                  60

Met Phe Asn Asp Thr Leu Arg Leu Ile Gly Glu His His Asp Gly Val
65                  70                  75                  80

Ser Lys Ala Asn Phe Ser Ile Ser Arg Met Thr Gln Asp Leu Ala Gly
                85                  90                  95

Thr Tyr Arg Cys Tyr Gly Ser Val Thr His Ser Pro Tyr Gln Val Ser
            100                 105                 110

Ala Pro Ser Asp Pro Leu Asp Ile Val Ile Ile Gly Leu Tyr Glu Lys
        115                 120                 125

Pro Ser Leu Ser Ala Gln Leu Gly Pro Thr Val Leu Ala Gly Glu Asn
    130                 135                 140
```

-continued

```
Val Thr Leu Ser Cys Ser Ser Arg Ser Ser Tyr Asp Met Tyr His Leu
145                 150                 155                 160

Ser Arg Glu Gly Glu Ala His Glu Arg Arg Leu Pro Ala Gly Pro Lys
                165                 170                 175

Val Asn Gly Thr Phe Gln Ala Asp Phe Pro Leu Gly Pro Ala Thr His
            180                 185                 190

Gly Gly Thr Tyr Arg Cys Phe Gly Ser Phe His Asp Ser Pro Tyr Glu
        195                 200                 205

Trp Ser Lys Ser Ser Asp Pro Leu Leu Val Ser Val Thr Gly Asn Pro
    210                 215                 220

Ser Asn Ser Trp Pro Ser Pro Thr Glu Pro Ser Ser Lys Thr Gly Asn
225                 230                 235                 240

Pro Arg His Leu His Ile Leu Ile Gly Thr Ser Val Val Ile Ile Leu
                245                 250                 255

Phe Ile Leu Leu Phe Phe Leu Leu His Arg Trp Cys Ser Asn Lys Lys
            260                 265                 270

Asn Ala Ala Val Met Asp Gln Glu Ser Ala Gly Asn Arg Thr Ala Asn
        275                 280                 285

Ser Glu Asp Ser Asp Glu Gln Asp Pro Gln Glu Val Thr Tyr Thr Gln
    290                 295                 300

Leu Asn His Cys Val Phe Thr Gln Arg Lys Ile Thr Arg Pro Ser Gln
305                 310                 315                 320

Arg Pro Lys Thr Pro Pro Thr Asp Ile Ile Val Tyr Thr Glu Leu Pro
                325                 330                 335

Asn Ala Glu Ser Arg Ser Lys Val Val Ser Cys Pro
            340                 345
```

<210> SEQ ID NO 61
<211> LENGTH: 1047
<212> TYPE: DNA
<213> ORGANISM: Homo sapiens

<400> SEQUENCE: 61

```
atgtcgctct tggtcgtcag catggcgtgt gttgggttct tcttgctgca gggggcctgg     60

ccacatgagg gagtccacag aaaaccttcc ctcctggccc acccaggtcg cctggtgaaa    120

tcagaagaga cagtcatcct gcagtgttgg tcagatgtca tgtttgaaca cttccttctg    180

cacagagagg ggatgtttaa cgacactttg cgcctcattg gagaacacca tgatggggtc    240

tccaaggcca acttctccat cagtcgcatg acgcaagacc tggcagggac ctacagatgc    300

tacggttctg ttactcactc cccctatcag gtgtcagctc ccagtgaccc tctggacatc    360

gtgatcatag gtctatatga gaaaccttct ctctcagccc agctgggccc cacggttctg    420

gcaggagaga atgtgacctt gtcctgcagc tcccggagct cctatgacat gtaccatcta    480

tccagggaag gggaggccca tgaacgtagg ctccctgcag ggcccaaggt caacggaaca    540

ttccaggctg actttcctct gggccctgcc acccacggag ggacctacag atgcttcggc    600

tctttccatg actctccata cgagtggtca aagtcaagtg acccactgct tgtttctgtc    660

acaggaaacc cttcaaatag ttggccttca cccactgaac caagctccaa aacgggtaac    720

ccccgacacc tgcacattct gattgggacc tcagtggtca tcatcctctt catcctcctc    780

ttctttctcc ttcatcgctg gtgctccaac aaaaaaaatg ctgcggtaat ggaccaagag    840

tctgcaggaa acagaacagc gaatagcgag gactctgatg aacaagaccc tcaggaggtg    900

acatacacac agttgaatca ctgcgttttc acacagagaa aaatcactcg cccttctcag    960
```

-continued

```
aggcccaaga cacccccaac agatatcatc gtgtacacgg aacttccaaa tgctgagtcc   1020

agatccaaag ttgtctcctg cccatga                                       1047


<210> SEQ ID NO 62
<211> LENGTH: 348
<212> TYPE: PRT
<213> ORGANISM: Homo sapiens

<400> SEQUENCE: 62

Met Ser Leu Met Val Val Ser Met Ala Cys Val Gly Phe Phe Leu Leu
1               5                   10                  15

Gln Gly Ala Trp Pro His Glu Gly Val His Arg Lys Pro Ser Leu Leu
            20                  25                  30

Ala His Pro Gly Arg Leu Val Lys Ser Glu Glu Thr Val Ile Leu Gln
        35                  40                  45

Cys Trp Ser Asp Val Arg Phe Glu His Phe Leu Leu His Arg Glu Gly
    50                  55                  60

Lys Phe Lys Asp Thr Leu His Leu Ile Gly Glu His His Asp Gly Val
65                  70                  75                  80

Ser Lys Ala Asn Phe Ser Ile Gly Pro Met Met Gln Asp Leu Ala Gly
                85                  90                  95

Thr Tyr Arg Cys Tyr Gly Ser Val Thr His Ser Pro Tyr Gln Leu Ser
            100                 105                 110

Ala Pro Ser Asp Pro Leu Asp Ile Val Ile Thr Gly Leu Tyr Glu Lys
        115                 120                 125

Pro Ser Leu Ser Ala Gln Pro Gly Pro Thr Val Leu Ala Gly Glu Ser
    130                 135                 140

Val Thr Leu Ser Cys Ser Ser Arg Ser Ser Tyr Asp Met Tyr His Leu
145                 150                 155                 160

Ser Arg Glu Gly Glu Ala His Glu Cys Arg Phe Ser Ala Gly Pro Lys
                165                 170                 175

Val Asn Gly Thr Phe Gln Ala Asp Phe Pro Leu Gly Pro Ala Thr His
            180                 185                 190

Gly Gly Thr Tyr Arg Cys Phe Gly Ser Phe Arg Asp Ser Pro Tyr Glu
        195                 200                 205

Trp Ser Asn Ser Ser Asp Pro Leu Leu Val Ser Val Thr Gly Asn Pro
    210                 215                 220

Ser Asn Ser Trp Pro Ser Pro Thr Glu Pro Ser Ser Lys Thr Gly Asn
225                 230                 235                 240

Pro Arg His Leu His Ile Leu Ile Gly Thr Ser Val Val Ile Ile Leu
                245                 250                 255

Phe Ile Leu Leu Phe Phe Leu Leu His Arg Trp Cys Ser Asn Lys Lys
            260                 265                 270

Asn Ala Ala Val Met Asp Gln Glu Ser Ala Gly Asn Arg Thr Ala Asn
        275                 280                 285

Ser Glu Asp Ser Asp Glu Gln Asp Pro Gln Glu Val Thr Tyr Thr Gln
    290                 295                 300

Leu Asn His Cys Val Phe Thr Gln Arg Lys Ile Thr Arg Pro Ser Gln
305                 310                 315                 320

Arg Pro Lys Thr Pro Pro Thr Asp Ile Ile Val Tyr Thr Glu Leu Pro
                325                 330                 335

Asn Ala Glu Ser Arg Ser Lys Val Val Ser Cys Pro
            340                 345
```

-continued

<210> SEQ ID NO 63
<211> LENGTH: 1047
<212> TYPE: DNA
<213> ORGANISM: Homo sapiens

<400> SEQUENCE: 63
atgtcgctca tggtcgtcag catggcgtgt gttgggttct tcttgctgca gggggcctgg 60
ccacatgagg gagtccacag aaaaccttcc ctcctggccc acccaggtcg cctggtgaaa 120
tcagaagaga cagtcatcct gcaatgttgg tcagatgtca ggtttgagca cttccttctg 180
cacagagaag ggaagtttaa ggacactttg cacctcattg gagagcacca tgatggggtc 240
tccaaagcca acttctccat cggtcccatg atgcaagacc ttgcagggac ctacagatgc 300
tacggttctg ttactcactc cccctatcag ttgtcagctc ccagtgaccc tctggacatc 360
gtcatcacag gtctatatga gaaaccttct ctctcagccc agccgggccc cacggttctg 420
gcaggagaga gcgtgacctt gtcctgcagc tcccggagct cctatgacat gtaccatcta 480
tccagggagg gggaggccca tgaatgtagg ttctctgcag ggcccaaggt caacggaaca 540
ttccaggccg actttcctct gggccctgcc acccacggag gaacctacag atgcttcggc 600
tctttccgtg actctccata cgagtggtca aactcgagtg acccactgct tgtttctgtc 660
acaggaaacc cttcaaatag ttggccttca cccactgaac caagctctaa aaccggtaac 720
ccccgacacc tgcacattct gattgggacc tcagtggtca tcatcctctt catcctcctc 780
ttctttctcc ttcatcgctg gtgctccaac aaaaaaaatg ctgcggtaat ggaccaagag 840
tctgcaggga acagaacagc gaatagcgag gactctgatg aacaagaccc tcaggaggtg 900
acatacacac agttgaatca ctgcgttttc acacagagaa aaatcactcg cccttctcag 960
aggcccaaga cacccccaac agatatcatc gtgtacacgg aacttccaaa tgctgagtcc 1020
agatccaaag ttgtctcctg cccatga 1047

<210> SEQ ID NO 64
<211> LENGTH: 341
<212> TYPE: PRT
<213> ORGANISM: Homo sapiens

<400> SEQUENCE: 64

Met Ser Leu Met Val Val Ser Met Val Cys Val Gly Phe Phe Leu Leu
1               5                   10                  15

Gln Gly Ala Trp Pro His Glu Gly Val His Arg Lys Pro Ser Leu Leu
            20                  25                  30

Ala His Pro Gly Pro Leu Val Lys Ser Glu Glu Thr Val Ile Leu Gln
        35                  40                  45

Cys Trp Ser Asp Val Arg Phe Gln His Phe Leu Leu His Arg Glu Gly
    50                  55                  60

Lys Phe Lys Asp Thr Leu His Leu Ile Gly Glu His His Asp Gly Val
65                  70                  75                  80

Ser Lys Ala Asn Phe Ser Ile Gly Pro Met Met Gln Asp Leu Ala Gly
                85                  90                  95

Thr Tyr Arg Cys Tyr Gly Ser Val Thr His Ser Pro Tyr Gln Leu Ser
            100                 105                 110

Ala Pro Ser Asp Pro Leu Asp Ile Val Ile Thr Gly Leu Tyr Glu Lys
        115                 120                 125

Pro Ser Leu Ser Ala Gln Pro Gly Pro Thr Val Leu Ala Gly Glu Ser
    130                 135                 140

-continued

```
Val Thr Leu Ser Cys Ser Ser Arg Ser Ser Tyr Asp Met Tyr His Leu
145                 150                 155                 160

Ser Arg Glu Gly Glu Ala His Glu Arg Arg Phe Ser Ala Gly Pro Lys
                165                 170                 175

Val Asn Gly Thr Phe Gln Ala Asp Phe Pro Leu Gly Pro Ala Thr His
            180                 185                 190

Gly Gly Thr Tyr Arg Cys Phe Gly Ser Phe Arg Asp Ser Pro Tyr Glu
        195                 200                 205

Trp Ser Asn Ser Ser Asp Pro Leu Leu Val Ser Val Thr Gly Asn Pro
    210                 215                 220

Ser Asn Ser Trp Pro Ser Pro Thr Glu Pro Ser Ser Glu Thr Gly Asn
225                 230                 235                 240

Pro Arg His Leu His Val Leu Ile Gly Thr Ser Val Val Ile Ile Leu
                245                 250                 255

Phe Ile Leu Leu Leu Phe Phe Leu Leu His Arg Trp Cys Cys Asn Lys
            260                 265                 270

Lys Asn Ala Val Val Met Asp Gln Glu Pro Ala Gly Asn Arg Thr Val
        275                 280                 285

Asn Arg Glu Asp Ser Asp Glu Gln Asp Pro Gln Glu Val Thr Tyr Ala
    290                 295                 300

Gln Leu Asn His Cys Val Phe Thr Gln Arg Lys Ile Thr Arg Pro Ser
305                 310                 315                 320

Gln Arg Pro Lys Thr Pro Pro Thr Asp Ile Ile Val Tyr Thr Glu Leu
                325                 330                 335

Pro Asn Ala Glu Pro
            340
```

<210> SEQ ID NO 65
<211> LENGTH: 1026
<212> TYPE: DNA
<213> ORGANISM: Homo sapiens

<400> SEQUENCE: 65

```
atgtcgctca tggtcgtcag catggtgtgt gttgggttct tcttgctgca gggggcctgg     60

ccacatgagg gagtccacag aaaaccttcc ctcctggccc acccaggtcc cctggtgaaa    120

tcagaagaga cagtcatcct gcaatgttgg tcagatgtca ggtttcagca cttccttctg    180

cacagagaag ggaagtttaa ggacactttg cacctcattg gagagcacca tgatggggtc    240

tccaaggcca acttctccat cggtcccatg atgcaagacc ttgcagggac ctacagatgc    300

tacggttctg ttactcactc cccctatcag ttgtcagctc ccagtgaccc tctggacatc    360

gtcatcacag gtctatatga gaaaccttct ctctcagccc agccgggccc cacggttctg    420

gcaggagaga gcgtgacctt gtcctgcagc tcccggagct cctatgacat gtaccatcta    480

tccagggagg gggaggccca tgaacgtagg ttctctgcag ggcccaaggt caacggaaca    540

ttccaggccg actttcctct gggccctgcc acccacggag gaacctacag atgcttcggc    600

tctttccgtg actctccata cgagtggtca aactcgagtg acccactgct tgtttctgtc    660

acaggaaacc cttcaaatag ttggccttca cccactgaac caagctccga aaccggtaac    720

cccagacacc tgcatgttct gattgggacc tcagtggtca tcatcctctt catcctcctc    780

ctcttctttc tccttcatcg ctggtgctgc aacaaaaaaa atgctgttgt aatggaccaa    840

gagcctgcag ggaacagaac agtgaacagg gaggactctg atgaacaaga ccctcaggag    900

gtgacatatg cacagttgaa tcactgcgtt ttcacacaga gaaaaatcac tcgcccttct    960
```

cagaggccca agacaccccc aacagatatc atcgtgtaca cggaacttcc aaatgctgag 1020
ccctga 1026

<210> SEQ ID NO 66
<211> LENGTH: 14740
<212> TYPE: DNA
<213> ORGANISM: Homo sapiens

<400> SEQUENCE: 66
gttcgggagg ttggatctca gacgtgtttt gagttggtca tagtgaagga cactaggtgt 60
caaattctag cgagaacaat ttccaggaag ccgtgttccg ctcttgagcg agcacccact 120
gggcctcatg caaggtagaa agagcctgcg tacgtcaccc tcccatgatg tggtcaacat 180
gtaaactgca tgggcagggc gccaaataac atcctgtgcg ctgctgagct gagctcggtc 240
gcggctgcct gtctgctccg gcagcaccat gtcgctcttg gtcgtcagca tggcgtgtgt 300
tggtgagtcc tggaaagcaa tagagggagg gagtgagggg atggagatct gggcccagag 360
gtggagatat aggcctggag gtggagttat gggcctggag tggagatctg ggcctggagt 420
ggatatatgg gcctagagat ggagtgatgg gcctagaagt ggagatctgg gcccagaggt 480
cgagatatag gcctggaggt ggagtgatgg gactgtagtg gagatctggg cctggagtgg 540
agataggaac ctggagggga gataggaacc tggaggggag atatgggcct ggaggtggag 600
atatgggcct ggagtggagt catgggcctg gaggtggagt tatgggcctg cagtagagat 660
atgggcctga agtggagaca tgggcctgga gtggagatat gggccaggag tggagatatg 720
ggcctagagg tcgatatctg ggcctggagt ggagatatgg gccaggagtg gagatatggg 780
cctagaggtc gatatctggg cctggagagg agatatgtgc ctaggatgga gatacgggcc 840
tgggtgtgga gatatgggac tggagaggat atatgggcct ggagtggaga tatgggactg 900
gagaggagat atggacctgg agtggagata agggcctgga ttggagatat gggcccaggg 960
tggagatctg agcctggatt ggagatatgg gcctggattg gcgatatggg cttagggtgg 1020
aaatatcggc ctggagtgga gatatgggcc tggagtggag atatgggctt gaggtgggga 1080
tatggacctg gaggctgggt ctctgcacag ccgacagccc tgttcttggg tgcaggtagg 1140
cactgagggt gagtttacct tcagcccagg aagggcctgg ctaccaagac tcacagccca 1200
gtgggggcag caagggtgcc ctggtttgcc tgcagatggg tcatccatca tgatctttct 1260
ttccagggtt cttcttgctg cagggggcct ggccacatga gggtgagtcc ttctccaaac 1320
cttcgggtgt catctcccca cataagagga ttttcctgaa atgggaggga agtcctgtca 1380
gggagtctct cataaactag gaagaaggga ccctggggtg ctgggcccac atttctgacc 1440
ttgcctccct ggcctttcat tcccttggca gagtcaagtt ctgtggggac cagggttaga 1500
ctacggtgct caaagctggg gtgtgtggtg gggaagtggt aggaacagca gatcctctga 1560
ggacaaaggt gttactcaca cacttcagcg tttccatgac ggtaggggct gcagtgtggc 1620
tgctgtcatt ctaccagaag aggtgggaaa accacagcca tggccctgac attccaatcc 1680
tctgatgggg actcagttgt ttattttcgt tcaggcatcg gctgatattc cattctcaaa 1740
ggacatgccc tccaccccat gtctaccctg tgttgtttta tgtgagtaat cttacagtat 1800
taaaatctag taggagtctc ttactcagca cttgctcaaa gttctcagct gacacttttg 1860
ttgtagggag acaccttgtg tttgcgggat gggtccttcc tttagccctg ggcaccaagg 1920
tgtgatagca gccatagaaa cttggaaagc gaggagaatc ttcagagcac agggagggag 1980
gggcggctcc acatcctcct ctctaaggcg gtgcctcctt ctccccacgg tggtcaggac 2040

-continued

```
aagcccttgc tgtctgcctg gccaagccct gtggtgcctc caggacatgt gattcttcag   2100
tgtcattctt atcttgggtt taacaacttc agtctgtaaa aggaagatgg ggtgcctgtc   2160
cctgagctct acaacataat attctggaac agccttttca tgggccctgt gaccccagca   2220
cacgcaggga cctatacatg tcggggttca caaccacact accccagtgg gtggtcggca   2280
cccagcaacc ccctggagat cacggtcaca ggtcagaggg ctcctgtctg ggattctcct   2340
tgtcccacct cctgaatccc agagctcctg gtgggcgtgt ccttgcgggt cccatcatgc   2400
aagtcctgac tgtatttggg gtaaaggggg attgaataca gggaaatggg tgctgtggtg   2460
ggaagaataa ttgtccccag tgatgactac attctaatcc ctggagtctg tgactattta   2520
tgatataggg gaagggactg aaggagaaga tggagctcag gttgttgatg agttgacctt   2580
gagatgggga gacagcctgg actgtcctga tgggctcagt gtagtcacag ggtccacat   2640
gaaaggagga ggaagagggg agtggggatt acagcagcat aatgggagtc tccatcagct   2700
ttgaaggtgg aggaagtcca ggagccatga atgcaggtgg cctatagagg ctggaaaagt   2760
caaggaactg attctcctga gtctccagag ggaacgaagc cctgcaggtg ccttgatttt   2820
acccacgaca aacagggtcc gatttctgtc tccagaattg gaaggggtta gtgtgctctc   2880
tcctggtgcc atgcttctga taattttcta cagcagcaac aggaaaccaa cactggaacc   2940
caggtcaagg acaagttaag aaacaacaca aggatagcca ggcatggtgg caggtgcatg   3000
taatcctagc gacttgggag gctgagggca ggagaatcac ttgaacccag gagacagagg   3060
ttgcagtgag cctagaccac accacttcac tccagcctgg gcaaaggagt gagactctgt   3120
cgccaaaatt aattaattaa ttaaagaaac caaacaagga gaaggttggc tacactgaga   3180
tcagcaaggc tcggatgatg atgccaccac caggctccat ccacataggg agcggttgat   3240
actcctccaa ccagcaccag gagccagcct atggaagctg gcactggcat ggcaagagtg   3300
gctcccagtc cctaccagga acagggtgtg tggccactgg tgcctgcctt actgatcagt   3360
tcatacctcc tgccaaggat tccaattcgt ccaaaagaga ttgaaccagg ctgctaagag   3420
cctggatgtg cagcctatcc tggttcctct tccaccccca catagacagc aggaaagaca   3480
ttagttcgaa atagatacaa cagcccaaga gatgaggctg agcccagcgg caagggaatc   3540
agaggctact agagacagag ggacagagaa gagtgaggga gacagatgga aggacctgca   3600
ccaggagtta tgggcacaga aaagaacatg aagacacaga gaggaaggag agagataaga   3660
caccaggaag gggaagcctg actcaatcca ggtgccatgg atgggatgat aaagagagac   3720
accttctaaa ctcacaacct ctcttcctag gagtccacag aaaaccttcc ctcctggccc   3780
acccaggtcg cctggtgaaa tcagaagaga cagtcatcct gcaatgttgg tcagatgtca   3840
tgtttgaaca cttccttctg cacagagagg ggatgtttaa cgacactttg cgcctcattg   3900
gagaacacca tgatggggtc tccaaggcca acttctccat cagtcgcatg acgcaagacc   3960
tggcagggac ctacagatgc tacggttctg ttactcactc cccctatcag gtgtcagctc   4020
ccagtgaccc tctggacatc gtgatcatag gtgagagtgt ccagactttc ttctcattgt   4080
cattgggatg cagagtgaat gatccaggaa ttggagaccc aggtggctgt aaggaagatg   4140
agcttggtat tcttatggag agagactgac ttggtgaggt ctgtgccaac agagacagag   4200
aaacaggaga cacaagtaga gaccaggtgt cataacagag aacagacaca ggggccatac   4260
cgggagttag aaaagacaga aagagttaaa ggagacacac agacagacat gtcccagaga   4320
gaggtgtccc tccatgctga ctttgctcag agacctggca caggttagaa gtttcatttc   4380
```

-continued

```
tgttttacct ccacaaagtg ttctctacca ggagaaccca aggacaccca tatttctgac   4440
ctgagttggg ccctgtggcc tcaggccttg tggcacctac agatgccatg tttattctga   4500
cacctctgcc ttccatgtaa tggagagtaa tcgtcccagg atatcatggc cccacaacac   4560
caacccctgt atgctgtgtg aacttgtagt ctccagactg gattctgagg ctcatattcc   4620
aaataagccc acttatgaga ggatcagtga gaggcacaga gagaaatcag ggacaccaaa   4680
aagcaaagac ataaacacac agagaatgag ccagaggaag gagattgaga gactcacaga   4740
cacataaaga gagagaaaag agggcagaga agtgagaatg atggaaggga gcagagaaaa   4800
gcactaaaat tagactcctg agggagaggc acaaggacat tgaaagatgg agatgtgggg   4860
atgaattgca gagattccaa agagaactag agagaccgag aggcagagca agacagatga   4920
tagatggata gatatagata gatgataaat aggtagatga tagataatag gttatagata   4980
catagatgat gattgattga ttcattaata gatgagacat agagatgatg atgatgaaga   5040
cagatagata gataatacat agagatacag aggcagacat agagaaatca tagagagaga   5100
gagatgatac atagatatag ataatagatg attgatggat agatagacaa ttgatggata   5160
aatagatgat atatagatat agatgacagg tagagaattt gtagataggc accgaataga   5220
taaatagata gatcgataga taatagatag aaatatgcag aaagttatga acaggacaca   5280
aagtgagaaa ctcagaatta aaaaaagtaa catcaagtca accaatccaa ggagagtcag   5340
agagaataaa acaatccaaa aagagaaaac atatctagag gtggggaagt gaggtcagag   5400
acctagagag acagagaagg tggaaggagg aaatagacat gaagagcgat ggggtagagg   5460
gtgagagaga gagagagaga gagcattagg tcatagaaca ggggagtgag ttctcagctc   5520
aggtgaaggg agctgtgaca aagaagatcc tccctgagga aactgcctct tctccttcca   5580
ggtctatatg agaaaccttc tctctcagcc cagctgggcc ccacggttct ggcaggagag   5640
aatgtgacct tgtcctgcag ctcccggagc tcctatgaca tgtaccatct atccagggaa   5700
ggggaggccc atgaacgtag gctccctgca gggcccaagg tcaacggaac attccaggct   5760
gactttcctc tgggccctgc cacccacgga gggacctaca gatgcttcgg ctctttccat   5820
gactctccat acgagtggtc aaagtcaagt gacccactgc ttgtttctgt cacaggtgag   5880
gaaagcccat ggctgtccca tgtcctatga tcctagagcc ttagctgagg agcttcctgc   5940
tgaggatgga gagaagcatg gacagatgca gagagaagac gcagcctcgg tgtgagggag   6000
ggatcagggc acaggatggc agacagggca cctccaaacc ctcctacatg gcctgcatgg   6060
aggcccacgg ccagggctcc aggcacccag gcagatggag aaagcggtca ggagagaccc   6120
agaggaggga gactgggctc agtttgggga gatcagaggt tccctcagcc cctcaacctt   6180
acccatttcc cagaagccca tcctggcctc tcacccacac agagatgtca tcaccagcaa   6240
cccctacacc ctttactttt ctttgaagaa atatttattg aggataaata tacctatata   6300
gcttaccact tttaacattt ttttttgagg tggagtctag ctctgtcccc tatgatggag   6360
tgcagtggca caatctcagc tcactgcaac ctccgcctcc tgggttcaag cgattctcct   6420
gcctcagcca cctgagtagc tagtgctaca ggcacgcacc accacgccag gctacttttt   6480
gtatttttag tagagaggtg gtttcaccat gttggtcgag ctggtctcga actcctgacc   6540
acgtgatcca cccgcatcag cctcccaaag tgctgggatt acaggcatgg gccaccaggc   6600
ccagccacat ttaccatttt taagtgtaaa gtctagtggt cataaataca tttttatata   6660
tatatatata tacatttttt ttaccctcca cccttttctt cctgtcctcc agtagccacc   6720
attctactct ctaccttcat gagatccacc ttttagctcc tgtatatggg tgagaaatgg   6780
```

```
gaatcttttt aatgacctcc agttccatcc atgtggctgc aaatgacagg atgttattct   6840
ttctatggat gagtagtctc cactgtgcgt atgtactaca ttctctctat ccattcaccc   6900
actgatgggc aggtaggttg actcctcatc ttggctactg tgaacagtgc tgcaccaatc   6960
atacgagtgc agatatcact tcgatatgtt gatttacttt cctttggata taaacccagt   7020
agtgaaattg ctggatacta tgaaagttct cttttttttt ttttttttctt ttttgagaaa   7080
gagtttccct ccttagccca agctggagtc aaagtggtgc aaccttggct cattgcaacc   7140
tccgcctcct gggttcaaat gattttcctg cctcagcctc cctagtagct gggattacag   7200
gtgcacacca ccatgcctgg ctactttttg gtttttttag tatagatgcg gtttccccat   7260
gttggctggg ctgctctcaa actcatgacc tcaactgagg tgcccgcctc agtctcccaa   7320
agtgccggga ttacaggcat gatccacctc acccaacctc tttttagttc tttaaaggac   7380
ttccatactt ttctccgtaa tggctgtact aatttacact cctaccaaca gggtaccagg   7440
gttctccttt ctctaccacc ttgccagcat ttcttttgcc tgtcttgcag ctaaaagcca   7500
ttttatttta tttcatttta ttttgagatg gagttttgct cttctcaccc aggctggagt   7560
gcagtggcgc tatctcggct caccacaacc tccacctccc aggttcaagc gattctcctg   7620
cctcagcctc ccgagtagct ggaattacag gcacacgcca ccacgcccta ctaatttttg   7680
tatttttagt agagacagcg tttctctatg tgggtcagac tggtctcaaa ctcccaacct   7740
tatgagattc acccacctca ggttctcaaa gttctaggat gacacaagtg agccacctca   7800
cccggcctaa aagccatttt aatggggtga gatgaaaact cactttgatt ttaatttgcg   7860
tttctctgat gatgagtgat actgagcact ttttcgtatg tggggaaatt tcatgtcttt   7920
tgctcctttt tcaattaaat catttgtttt attgagttgt ttgagcttct tatatttcta   7980
gttattaatc ccatctcaga tgcatagttt gcacatattt gctcccaatc tgtgggttgt   8040
ctcttcactt tgttggttta tttttagcag tgctgaagtt gcttagtttg aggtaatccc   8100
aatggtctgt ttttgcttcg attacttgtg ttttgaaggt ttaaaacaaa atgtcttcct   8160
tcagacaaac gtcctggagc atttccccaa tattttgttc tacgtgtttc ataggttcag   8220
gccttagact cacatcttta atccattttc atttgatttt tgtgtatggt gacaggtaga   8280
gttgcagttt cattcctctg catgtagatg tccaggtttc cctgcactgt ttattgaaaa   8340
gactgtcctt tcctgattgt gagttcttgg catctttgtc aaagtccatt ggatgggctg   8400
ggcttggtgg ctaacacctg caatttcagc actttgggag cccgaggtgg gtggatcacc   8460
tgaggccagg agttcaagat tagtctggcc aacgtgatga aacatcgtct ccactaaaaa   8520
tataaaaaatt agctgagcat ggtggtcagc acctgtaata ccactactca ggaatttgag   8580
gcaagagaat gattgaaccc aggaggctga ggttgcagtg aaccgagatt gcacctctgc   8640
actccagcct gagtgacaga gcaagactcc atctcaaaag aaaaaataaa aaaccattgg   8700
atgtaaatgc atggaatata tctgtgttat tcattctgct ccgttgttct atgtgccttt   8760
ctttatgcca atgtcatgct attttgctta ctacagctct gtaacatatt ttgagatcag   8820
gtagtgtgat gctcctgttt tctctttata tcttgaagtc tcaagacagt gggtgtcata   8880
taaaaaaatt atggaaaaaa ggatcccagg actcccaggg cccaatatta gataagagag   8940
tgttggccat gaaccatcct caaagatttc cactgagtgg aggacagaca ccctcatttc   9000
ctcacctctc tcctgtctca tgttctagga aacccttcaa atagttggcc ttcacccact   9060
gaaccaagct ccaaaaccgg tgagtacaga accctcttat atccgctttt ggaaccctgg   9120
```

-continued

```
ggaggtggga accttggatt caggcgttga ctcagcatct cacagctctg acattgtaca   9180
cttgtcttcc accatctccg aactccagat actcctacag cgaaagggat ctgggcccaa   9240
cacagggctc agtgaaatct cttcatctct cattttatgg agctgagacc tcctacaagc   9300
tagaagaatg attgccaatc tgacatcctt ctcaggaaaa atgcaatgtt tgttctacct   9360
gcattcctaa ctggaggata aattcctgga gacttgagag agggaaggga agggaacatc   9420
tgatgagggc aaggtgtttt agagaagttc cacttgccaa ggaatgagct cctgtaggtc   9480
atgaagcaac cctggctgac tccgcagaga aagagccttg ccgtaacaga gaacagagct   9540
catgcacgca cacttcgact cactgactca ttcagccacg gccccatgct caggctgtgc   9600
agtgtggaac cttttcctat tgttgccata acaaatttcc acaagattcg tgggtgaaaa   9660
caaaacggtt ttttaattat cttacagtgc tgtagctcaa agtaggaagt gcatcttact   9720
gggctaaaat caaggtgaca gcaaggctgc cttccctctg aggattccag gcacgaatct   9780
gcttctcact tgtcccagct tctaaaggct cccagttcct tggctcctgg tccccttcct   9840
ccttcctcaa agcccacaaa gactggtcac atctcacatg gcatcactca gtgccttctt   9900
ccttaccaca cctctttctc tgagtgctgc tctcccttct tcctcatctt ttgaaaactt   9960
ggggattcta ttgggttcac caagatgaaa atccctcata atctcctgga aatcatccag  10020
gatacccttg ttttaagttc agctgattag caaccataat tccatctgca atcttcattc  10080
ctcctttcca tgtaaaataa catattcaca agctgtggag gctaggacag ggacattttg  10140
gggtgggaca gcattctcct gccttccaca aacagtgaac aagatgcatt tggcctctgc  10200
ccttgggaca ctgatattgc agatggttaa atgggagggc agaaaatgaa cgcacaagtg  10260
gatctataaa tgaatggtcc attgggaagc atctgtgcat gaaatctatt ttttgtttgt  10320
tcttttgttt attgagacag agtcgccctc tgtcttccag gctacagtgc agtgtcacga  10380
tcttggctca ctgcaacctg cgtctcctgg attcaagtga ttctcctgcc tccgcctctc  10440
gagtagctgg gattacaggc aactgccacc gtgcccggct aattcttttt gtatattttt  10500
tgtagagagg atgtttcacc acgttggcca agcttgtctg aaactcccaa cctcaagtga  10560
tccgaccgtc tcagcatgcc aaagtaatgg gactacaggc gtgagccact gtgcccagcc  10620
agaattcaaa atcaataata gataatgctg agtgtatgat ttcaggtgac aaagaaggtc  10680
tcactattca gatatttgtg acattaatga aaaacacgga atgaacccct gaaagattgg  10740
cggaaggatt ttgcacacac agctgtcagc catgaaggca caaaggtgaa aacaatctga  10800
tgtggaagga agaggctctg actcaaatgc tgggaatgag gtggggagaa tgacaagacg  10860
actgtagaga gacggagagc acactgggta cacaggaaac taaggaggaa caaggagtgt  10920
gtgtttgaca ctcacagcca ttggattcac ctcggggtaa ccaggaatcc ctacatgatt  10980
aatatgactg acatgaaaat aagggaggcc caggtgcata actggaatct aggagaccgt  11040
ggaaaaggca attgccgccc cactggtgaa atgtggtgct gatttagaca ctaaatgaat  11100
gaagtagatg gatataagat atgtttgtga ggtagaatca ttgactggaa aggcttactg  11160
ggtttgattt tcctacttgt ttaatcctcg cttaattaat ttctttctga gatttattca  11220
tcctacacat aaatcaatac ctggcaaagg agtgacagat atatgagtgg tggtggaaat  11280
gaagagactt attatagcat aatatacaag tctgtgaaca gtggctcacg cctgtaacct  11340
agcactgcag gaggccaagg tgggtggatt ccatgaagtc aggagttcca gaccagcctg  11400
gccaacgtgg tgaaacccta tctctactaa aaatacaaaa attagccgag cacgatggtg  11460
catccctgta atcccagctc ctattctgga ggatgaagca ggagaatgac ttcaacccag  11520
```

-continued taggtggagg ttgcagtgag tggagattgc atcactgcac tccagcctgg gggacacaag 11580
gagactctat ctcaaaaaat aaaaataaga aatacataaa tataataaaa cacacacgaa 11640
tgacaaaggc acctgaattc caatcatgat ttttctattt ctctataatt acttctttga 11700
tcctttatct tatccattag gcaatgagcc taaaacctct tccctatttg gctttctgtg 11760
agcatgagat catatagaaa atgtgaaagc ccgctgaatc ctccagcaca gatcctggaa 11820
tagagaaagt gctctggtca tcacaaaaaa aacttgccca ctcacccaaa tcccccacct 11880
cacccctact tccaatcacc tgtggagatt cagatagacc atggggaggt aaacattaac 11940
actccttgga gtgagtccag atcttggaat cagagatcag cgacagcact agctcctgct 12000 ccccttttcct actaattcac aggaggacag gtggttttga agcaatagat ggccgagggg 12060
gtggtccttc ccccagcctc tcgggtagaa cagcagccta atatgtgtct cccgagatca 12120
caaagagcag caggtttcac acgggcttca acactatttc ctggccgttt gacataagag 12180
aattctattt cgcttttttt atcttgattt cacttttgtt ttctttcctt ggagaatgca 12240
agttgtttga ttcaagaatg ctgtggatgt agaaacccta aagcacattc gctgtgaatc 12300
aatcccagtc cagtcttccc agagaagact ctaaacacct cctggactgc acctgggcct 12360
atgccaattc ctatcactca ccgtcactcc agggagacag aacacacaga gaatacgtta 12420
cataggcagg ttcattacta acagataagc agcgagtgac aacagaaacc tatatttcaa 12480
tgtgacccag tccctcaagg ctcagaaaag ctcctcggga catatggagt caccccattt 12540
gcagtgtagc tgcgggaagc cagaaagcag cccagcctgg gttttgtacc ctggagccac 12600
aggaagcact cagctaaagc actgcatgac gtcctccagg aagaacagga agacagccca 12660
gggtgttctg agacgttcct cctgatctca ggaagttgct gtcttaggcc atttttgttg 12720
ctctaaagga acacttgagc ctcggtaact tctaaagaaa agagattggt ttgcctcacc 12780
gttctgcagg ctgtactgga agcatggcac cagcatctat ttctcgtgac ggcctcaggc 12840
tgctcccact ctggcagaag ggaaggaggg tctgtctgtg cagagaccac agagatcaca 12900
cggcaagaga gggagcaagg gggaggggga gcgatggagc ttccaagctc tttttaacaa 12960
ccagctctcc gggaactaat agaggggggaa cttgctaacc ccgtctcctt gggacagcat 13020
tgatgtgttc atgatggatc cacctccatg acccaaacac ctctcaagag gcccaacctc 13080
ccacagtggg ggtgaaattt caatgtgagg tttgaagggg tcaaacatct caactaaagt 13140
agtcgtatcc tcagcacgtt ctatggttac tatgagagct ataactgaaa aagcaggaga 13200
aagctgggtc tcctgccatc tgggtgcttg tcctaaagag gtgttttatg tggttacctg 13260
tcaatcaaga aatgcgagac aattcataaa gaggaactgc taagattagc ttcttattgg 13320
tgtctcatct tcttccaggt aacccccgac acctgcacat tctgattggg acctcagtgg 13380
tcatcatcct cttcatcctc ctcttctttc tccttcatcg ctggtgctcc aacaagaaaa 13440
gtaagtctca cgaagcagag gccagagagc tcagggccat gtggggaagc aggatgggag 13500
cactcaggtg tgtgttcctc acaaacagga tggtccctgg cccaaggcag cagccacaga 13560
ggcaggactt tctagagagg gcaccagact ccctgtccct gccttcaact cacagaccgt 13620
tgcctgattc tgaactgtat cctcatgtcc cctgcagcca ctcacatcca ggagaaggtt 13680
ccatgacagg cagaaagtgg gagacagaat caatgggatg ggaactcaga gctattcatg 13740
ggatgggtcc ttgagctcag agagatagaa tgtctgagtc tgctgttggc aactgaggga 13800
cctcagccac ctatggtctc cccctgtatg ttggtatctg cttatgaaat gaggacccag 13860

-continued aagtgccctc cgagctgttt tgttgacttc cgtcttctac agatgctgcg gtaatggacc 13920
aagagtctgc aggaaacaga acagcgaata gcgaggtagg tactcctcgg cccgggctcg 13980
tggctactgt tattcccaaa gagtcctgga aaatgtgagc accctccctc actcagcatt 14040
tccctctctc caggactctg atgaacaaga ccctcaggag gtgacataca cacagttgaa 14100
tcactgcgtt ttcacacaga gaaaaatcac tcgcccttct cagaggccca agacaccccc 14160
aacagatatc atcgtgtaca cggaacttcc aaatgctgag tccagatcca aagttgtctc 14220
ctgcccatga gcaccacagt caggccttga gggcgtcttc tagggagaca acagccctgt 14280
ctcaaaaccg ggttgccagc tcccatgtac cagcagctgg aatctgaagg catgagtctg 14340
catcttaggg catcgatctt cctcacacca caaatctgaa tgtgcctctc acttgcttac 14400
aaatgtctaa ggtccccact gcctgctgga gaaaaaacac actcctttgc ttagcccaca 14460
gttctccatt tcacttgacc cctgcccacc tctccaacct aactggctta cttcctagtc 14520
tacttgaggc tgcaatcaca ctgaggaact cacaattcca aacatacaag aggctccctc 14580
ttaacgcagc acttagacac gtgttgttcc accttccctc atgctgttcc acctcccctc 14640
agactagctt tcagtcttct gtcagcagta aaacttatat attttttaaa ataacttcaa 14700
tgtagttttc catccttcaa ataaacatgt ctgcccccat 14740

<210> SEQ ID NO 67
<211> LENGTH: 14696
<212> TYPE: DNA
<213> ORGANISM: Homo sapiens

<400> SEQUENCE: 67
tttaatgtaa gcacagaatt caatcatctc gtgtatgaga ggttggatct gagacgtctt 60
ttgagtctgg tcgtagtgaa ggacgcaagg tgtcaattct agtgagaaca atttccagga 120
agccatgttc cgctcttgag cgagcaccca ctgggcctca tgcaaggtag aaagagcctg 180
cgtacgtcac cctcccatga tgtggtcaac atgtaaactg catgggcagg gcgccaaata 240
acatcctgtg cgctgctgag ctgagctggg gcgcggccgc ctgtctgcac agacagcacc 300
atgtcgctca tggtcgtcag catggcgtgt gttggtgagt cctggaaggg aatcgaggga 360
gggagtgcgg ggatggagat cggggcccag agttggagat ataggcctgg aagtggagtt 420
atgggcctag agatggagtg atgggcctag aagtggagat ctgggcctgg agtggagata 480
tgggcctgga ggttgagata tgggcctgca gtagagatat gggcttgtag tggagacatg 540
ggcctggaga tggagatatg ggcctggaga tggagatatg ggcctgcagt agagataggg 600
gcctggagtg gagatatggg cctggagtgg agatatgggc ctgaagtgga gatatgggcc 660
tggaggtgga gatatgggcc tggaggtgga gatatgggcc tggagtggag atatgggtct 720
ggaggtggag atacgggcct gcagtagaga tatgggcctg gagtggagat atgggccagg 780
agtggagtta tgggcctaga ggtggatatc tgggcctgga gtggagatat gggcctagga 840
aggagatatg ggcctgggtg tggagatatg ggactggaga ggtgatatgg gcctggagtg 900
gagatatggg cttagggtgg agttctgggc ctggggcgga gatatgggac tggattggag 960
ataggggcct agggtggaga tctgagcctg gattggcgat atgggcctag ggtggaaata 1020
tcagcctgga gtggagatat gggcttgggg tggggatatg ggcctggaaa ctgggtctct 1080
gcacagccga cagccctgtt cttgggtgca ggtaggcact gagggtgagt ttaacttcag 1140
cccaggaagg gcctggctgc caagactcac agcccagtgg gggcagcaag ggagggctgg 1200
ttcgcctgca gatggatcgt ccatcatgat ctttctttcc agggttcttc ttgctgcagg 1260

-continued

```
gggcctggcc acatgagggt gagtccttct ccaaaccttc gggtgtcatc tccccacata   1320
agaggatttt cctgaaacag gagggaagtc ctgtcgggga gtctctcata aactaggaag   1380
agaggaccct ggggtgctca gcccacattt ctgacctcgc ctccctggcc tctcaacccc   1440
ttggcagagt caagttctgt ggggaccagg gttagactgg ggtgctcaaa gctggggtgt   1500
gtggttggga agtggtagga acagcagatc ctctgaggac aaaggtgtta ctcacacact   1560
tcagcgtttc catgatggta ggggctgcag tgtggctgct gtcattctac cagaagaggt   1620
gggaaaccac agccatggcc ctgacattcc aaatcctctg atgggggctc agttgtttat   1680
tttcgttcag gcatccgctg atatccattc acaaaggaca tgccctccac ctcatgtcta   1740
ccctgtgttg ttttatgtga gtaatcttac agtatcaaaa tctagtagga gtctctttac   1800
tcagcacttg ctcaaagttc tcagctgagg cttttgttgt agggagacac catgtctttg   1860
cgggatgggt ccttccttca gccctgggca ccaaggtgtg atagtagcca tagaaacgtg   1920
gaaagcgagg agaatcttct gagcacaggg agggaggggc agttccacat cctcctctct   1980
aaggcggcgc ctccttctcc ccaaggtggt caggacaagc ccttgctgtc tgcctggccc   2040
agccttgtgg tgcctctagg acatgtcatt cttcggtgtc actcttatct tgggtttaac   2100
aacttcagtc tgtacaagga aggtggggtg cctgtccctg agctctacaa cagaatattc   2160
tggaacagcc ttttcatggg ccctgtgacc cccgcacaac agggacatac agatgtcggg   2220
gttcacacac acactccccc agtgggtggt cagcacccag caaccccctg gtgatcgtgg   2280
tcataggtca gagggctcct gtcttggatt ctccttgtcc cacctcctga atcccagagc   2340
ttctggtggg catgtccttg agggtcccat cacgcaggcc ctgactgtat ttgtggtaaa   2400
gggggattga atacagggaa atgggtgctg tggtgggaag aataattgtc cccagtgatg   2460
actacattct aatccctgga gtctgtgact atgtatgtta taggggaagg gactgaaggg   2520
gaagatggag ctcatgggga gacagcctgg actgtcccac tgggctcagt gtaatcacaa   2580
gggtgcacat gaaaggagga ggaagagggg agtggggatt agagcagtcc agtggaagtc   2640
ttcaccagct ttgaaggtgg aggaaggcca agagccatga atgcaggtgg cctatagagg   2700
ctggaaaagt caaggaactg attctccaga gtctccagag ggaacaaagc cctgcagatg   2760
ccttgatttt agcccaggaa aaatagggtc caatttctgt ctccagtact ggaaggtgtc   2820
agtgtggtct ctcctgcttc catgcttctg ataattttgt acagcagcaa caggaaacca   2880
acactggaac ccaggtcaag gacaagttaa gaaacaaccc aaggaaagcc aggcatggtg   2940
gcaggtgcat gtaatcctag cgactcagga ggctgagggc aggagaatca cttgaaccca   3000
ggaaacagag gttgcagtga gcctagacca caccacttca ctccagcctg ggtgaaggag   3060
tgagactctg tctccaaaat taattaatta attaaagaaa ccaaagaagg agaaggttgg   3120
ctaccctgag atcagcaagg gtgggatgat gatgccacca ccaggctcca tccacatagg   3180
gaggggttga tactcctcca accagcacca ggagccagcc tatggaagct ggcaccatgg   3240
agaaggcaca ggcatggcaa gagtggctcc cagtccccac caggaacagg gtgtgtggac   3300
actggtgcct gccttattca tcagttcata tcttctgcca aggattgcaa ttcatccaaa   3360
agagattgaa ccaggctgat aagagcctgg atgtgcagcc tatcctggtt cctctttcac   3420
ccccacataa acagcaggaa agacattagt gtgaaataga tacaacaccc caagagatga   3480
ggctaagccc agtgggaagg gaatcagagg ctactagaga cagagggaca gagaagaggg   3540
agggagacag atggaaggac ctgcaccagg agttaagggc acagaaaaga acatgaagac   3600
```

-continued

```
acagagagga aggagagaga cagacaccag caaggggaag cctcactcat tctaggtgcc   3660
atggatggga tgataaagag agacaccttc taaactcaca acctctcttc ctaggagtcc   3720
acagaaaacc ttccctcctg gcccacccag gtcgcctggt gaaatcagaa gagacagtca   3780
tcctgcaatg ttggtcagat gtcaggtttg agcacttcct tctgcacaga gaagggaagt   3840
ttaaggacac tttgcacctc attggagagc accatgatgg ggtctccaaa gccaacttct   3900
ccatcggtcc catgatgcaa gaccttgcag ggacctacag atgctacggt tctgttactc   3960
actcccccta tcagttgtca gctcccagtg accctctgga catcgtcatc acaggtgaga   4020
gtgtccggac attctcattg tcattgggct gcagagtgaa tgatccacga cttggaaccc   4080
ccaggtagtt gtaaggaaga tgagcttggt attcttatgg agagagactg acttgctgag   4140
gtttgtacca acagagacag agaaacagga gacacaagta cagaccaggt gtcataacgg   4200
aggacagaca caggggccat acagggagtt agaaaagaca gaaagagtta aaagagacag   4260
acagacagac atgtcccaga gagaggtgtc cctccatgct gactttgctc acagacctgg   4320
cacaggttag aagtttcatt tctgttttac ctccacaaag tgttctctac caggagaacc   4380
caaggacacc catatttctg acctgagttg ggccctgtgg cctcaggcct tgtggcacct   4440
acaggccatg tttattctga cacctctgcc ttccatgtaa tggagagtaa ccgtcccagg   4500
atatcatggc cccagaacac caacccctgt atgctgtgtg aacttgtggt ctccagactg   4560
gattctgagg ctcacattcc aaataacccc acatatgaaa ggatcactga gaggcacaga   4620
gaaaaatcag gaacaccaaa aagcaaagac ataaacacac ggagaatgag ccagaggaag   4680
gagattgaga gactcacaga cacataaaga gagagaaaag agggcagagg agtggtgaga   4740
atgatggcag ggagcagaga aaagcactaa aattagagtc ctgagagaga ggcacaagga   4800
catagaaaca tggagatgtg gggatgaatt gcagagattc caaagagagc tagagagacc   4860
gagaggcaga gcaatacaga tgatagatgg atagatatag atagatgata aataggtaga   4920
tgatagataa taggttaaag atacatagat gatgattgat tgattcatta atagataata   4980
catagagatg atgatgatga agacagataa tacgtacaga tagagaggca gacagaaatc   5040
atagagagag agatgataca tacatataaa taacagatga ttgatggata gatagacaac   5100
tgatagatac atagatgata tatagatata gatgacaggt agagaatttg tagataggca   5160
ccgaatagat aaatagatag atcgacagat aatagataga aatatgcaga aagttatgaa   5220
caggacacaa cgtgagaaac ttagaattta aaaaagtaac atcaagtcaa ccaatccaag   5280
gagagtcaga gagaataaaa caatccaaaa acggaaaaca tatctagagg tggggaagcg   5340
aggtcagaga cctagagaga cagagaaggt ggaagaagga aatagacatg aagagagatg   5400
gggtggaggg tgagagagag agagagagag cattaggtca tagagcaggg gagtgagttc   5460
tcagctcagg tgaagggagc tgtgacaagg aagatcctcc ctgaggaaaa tgcctcttct   5520
ccttccaggt ctatatgaga aaccttctct ctcagcccag ccgggcccca cggttctggc   5580
aggagagagc gtgaccttgt cctgcagctc ccggagctcc tatgacatgt accatctatc   5640
cagggagggg gaggcccatg aatgtaggtt ctctgcaggg cccaaggtca acggaacatt   5700
ccaggccgac tttcctctgg gccctgccac ccacggagga acctacagat gcttcggctc   5760
tttccgtgac tctccatacg agtggtcaaa ctcgagtgac ccactgcttg tttctgtcac   5820
aggtgaggaa accccatatc tgtctcatgt cctatgatcc tagagcctta gctgaggagc   5880
ttcctgctga tgatggagat aagcatggac agatgcagag agaagacgaa gcttgggtgt   5940
gagggaggga tcagggcaca ggatggcaga cagggcacct ccaaaccctc ctacacggcc   6000
```

tgcatgaagg cccgcggcca gggctccagg cacacaggca gatggagaaa gcggtcagga 6060
gagacccaga ggagggagac tgggctcagt ttgggaagat cagaggttcc ctcagcccct 6120
caacattacc catttcccag aagcccatcc tggcctctca cccacacagg gatgtcatca 6180
ccagcaaccc ctacaccctt tacttttgtt tgaagaaata tttattgagg ataaatatac 6240
ctatatagct taccaccttt aacatttttt tttttttga ggcagagtct agctctgtcc 6300
cctatgctgc agtgcagtgg cacaatctca gctcactgca acttccgcct cctgggttca 6360
agtgattctc ctgcctcagc cacctgagta gctggtgcta caggcgcgca ccaccacgcc 6420
aggctacttt ttgtattttt agtagagagg tggtttcacc atgttggtcg agctggtctc 6480
caactcctga ccacgtgatc cacccgcatc tgcctcccaa agtgctggga ttacaggcat 6540
gagccaccac tcccagccac atttaccatt tttaagtgta aagtctagtg gtcataaata 6600
catttataaa tatatatata tatatatatg tatgtatata tatatacaca cacatatata 6660
tacatatata tatgtgtata tatatatata tatatatata tatatatata tatatatata 6720
tttttttttt ttttaccctc caccctttc ttcctggcct ctggaagcca ccattctact 6780
ctctaccttc atgagatcca ccttttagct ctgtatatgg gtgagaaatg ggaatctttg 6840
taatgacttc cagttccatc catgtggctg caaatatcag gatgttattc tttctatgga 6900
tgagtagtct ccactgtgcg tatgtactac attctctcta tccattcatc cactgatggg 6960
caggtaggtt gactccacat cttggctact gtgaacagtg ctgcaccaat catacgagtg 7020
cagatatcac ttcgatatat tgatttactt tcctttggat ataaacccag tagtgaaatt 7080
gctggatact atgaaagttc tctttttagt tattcgtttg ttgttttgtt tttgtttttg 7140
agacagtttc cctctgtgcc caggctggag tacaagtgat gtcatcttgg ctcattgcaa 7200
cctctgcctc ctgggttcaa atgattttcc tacctcagcc tccctagtag ctgggattac 7260
aggtgcacgc caccatgcct ggctactttt tggttttttt agtatagatg gggtttcccc 7320
atgttggctg ggctgctctc aaactcatga cctcaactga ggtgtccgcc tcggtctccc 7380
aaagtgccgg gattacaggc atgatccacc tcacccaacc tctttttagt tctttaaagg 7440
acttccacac ttttctccgt aaaggctgta ctaatttaca ctcctaccaa cagggtatta 7500
gggttctcct ttctctacca ctttggcagg atttcctttg cctgtcttgc agctaaaagc 7560
cattttactt tatttcattt tattttgaga tggagtttcg ctcttgtcac ccaggctgga 7620
gtgcagtggt gcgatctcgg ctcaccacaa cctccacctc ccaggttcaa gcgattctcc 7680
tgcctcagcc tcccgagtag ctggaattac aggcacacgc caccacgccc gactaatttt 7740
tgtattttta gtagagacag tgtttctcca tgtgggtcag actggtctca aactcccgac 7800
cttatgagat tcacccacct caggctctca aagatctagg atgacagacg tgagccacca 7860
cgcccggcct aaaagccatt ttaatggggt gagatgaaaa ctcactttga ttttaatttg 7920
cgtttctctg atgatgagtg atactgagca gtttttcgta tgtggggaaa tttcatgtct 7980
tttgctcctg tttcaattaa atcatttgtt ttattgagtt gtttgagctt cttatatttc 8040
tagttattaa tcccatctca gatgcatagt ttgcacatat ttgctcccaa tctgtgggtt 8100
gtctcttcac tttgttggtt tatttttagc ggtgcagaag ttgcttagct tgaggtaatc 8160
ccaatggtct atttttgctt cgattacttg tgttttgaag gtttaaaaca aaatgtcttc 8220
cttcagacaa atgtcctgga gcatttcccc aatattttct tctacgtgtt tcatatggttc 8280
aggccttaga ctcacatctt taatccattt tcatttgatt tttgtgtatg gtgacaggta 8340

-continued

```
gaggtgcagt ttcattcctc tgcatgtaga tgtccaggtt tccctgcact gtttattgaa   8400
aagactgtcc tttcctgatt gtgagttctt ggcacctttg tcaaagtcca ttggatgggc   8460
tgggcatggt gactgacacc tgcaatttca gcactttggg agcccaaggc gggtggatca   8520
cctgaggcca ggagttcaag attagtctgg ccgacgtgat gaaacattgt ctccactaaa   8580
aatatataaa ttagctgagc atggtggtca gcacctataa taccactact caggagtttg   8640
aggccagaga attgattgaa cccaggaggc tgtggtggca gtgaaccgag attgcacctc   8700
tgcactccag cctgggtgac agagcgagac tccatctcaa aagaaaaaag aaaaaaacat   8760
tggatgtaaa tgcatggatt atatttgtgt tgttcattct gctccattgt tctatgtgcc   8820
tttcttcatg ccaacatcat gctgtcttgc ttactacagc tctgtaacat attttgagat   8880
caggtagtgt gatgctcctg ttttctcttt ataccttgaa gtctcaagac aatgggcgtc   8940
acatacaaaa attatggaaa aaaggatccc aggactccca gggcccaata ttagataaca   9000
gagtgttggc catgaaccaa cctcaaagat ttccattgag tagaggacag acaccctcat   9060
ttcctcacct ctctcctgtc tcatgttcta ggaaaccctt caaatagttg gccttcaccc   9120
actgaaccaa gctctaaaac cggtgagtac agaaccctct tatatccgct tttggaaacc   9180
tggggaggta gaaaccttcg atgcaggcat tgactcagca tctcgcagct ctgacattgt   9240
acgcctgtct tctaccatct ccgaactcca gatactccaa cagcgaaagg gatctgggcc   9300
caacctaggg ctcagtgaaa tctcttaatc tctcatttta tggagctgag acctcctaca   9360
agctagaaga atgattgcca atctgacatc cttctcagga aaaatgcaat gtttgttctg   9420
cctgcattcc taactggagg ataaattcct gggggcttga gagagggaag ggaagggaac   9480
atctgatgag ggcgaggtgt tttagagaag ttccacttgc caaggaatga attactgttg   9540
gtcatgaagc aaccctggct gactcagcag agcaacagcc ttgccgtaac agagaacgga   9600
gctcatgcac gcacacttcg actcactgac tcattcagcc acggccccat gctcaggctg   9660
tgcagtgcgg aaccttttcc tattgttgcc ataacaaatt tccacaagat tcgtgggtga   9720
aaacaaaacg gtttttttaat tatcttacag tgctgtagct caaagtagga agtgcatctt   9780
actgggctaa aatcaaggtg acagcaaggc tgccttccct ctgaggattc caggcaagaa   9840
tctgcttctc acttgtccca gcttctaaag gctcccagtt ccttggctcc tggtcccctt   9900
cctccttcct caaaacccac aaagactggt cacatctcac atggcatcac tcagtgcctt   9960
cttccttacc acacctcttt ctctgaatgc tgctctccct tcttccttat cttttgaaaa  10020
cttggggatt ctattgggtt caccaagatg aaaatccctc ataatctcct ggaaatcatc  10080
caggataccc ttgttttaag ttcagctgat tagcaaccgt aattccatct acaatcttca  10140
ttcctccttt ccatgtaaaa taacatattc acaaggtatg gaggctagga cagggacatt  10200
ttggggtggg acagcattct cctgccttcc acaaacagtg aacaagatgc atttggcctc  10260
tgcccttggg acactgatat tgcagatggt taaatgggag ggcagaaaat gaatgcacaa  10320
gtggatctat aaatgaatga tccattggga agcatctgtg catgaaatct atttttttgtt  10380
tgttcttttg tttattgaga cagagttgcc ctctgtcttc caggctacag tgcagtgtca  10440
cgatcttggc tcactgcaac ctgcttctcc tggattcaag tgattctcct gcctccgcct  10500
ctcgagtagc tgggattaca ggcaactgcc accgtgcccg gctaattctt tttgtatatt  10560
ttttgtagag aggatgtttc accacgttgg ccaagcttgt ctgaaactcc caacctcaag  10620
tgatccgacc gtctcagcat gccaaagtaa tgggactaca ggcgtgagcc actgtgccca  10680
gccagaattc aaaatcaata atagataatg ctgagtgtat gatttcaggt gacaaagaag  10740
```

```
gtctcactat tcagatattt gtgacattaa tgaaaaacac ggattgaacc cctgaaagat  10800
tggcggaagg attttgcaca cacagctgtc agccgtgaag gcacaaaggt gaaaacaatc  10860
tgatgtggaa ggaagaggct cttcctcaaa tgctgggaat gatgtgggga gaatgacaag  10920
atgactgtgg agagacggag agcacactgg gtacacagga aactaaggag gaacaaggag  10980
tgtgtgtttg acactcacag ccattggatt cacctcgggg tagccaggaa tccctacatg  11040
attaatatga ctgacatgaa aataagggag gctcagttgc ataactggaa tctaggagac  11100
cgtggaaaag gcaattgccg ccccactggt gaaatgtggt gctgatttag acactaaatg  11160
aatgaagtag atggatataa gataggtttg tgaggtagaa tcattgactg gaaaggcttg  11220
ctgggtttga ttttcctact tgtttaatcc tcgcttaatt aatttctttc tgagatttat  11280
tcatcctaca cataaatcaa tacctggcaa aggagtgaca gatatatgag ggtggtgga  11340
aatgaagaga cctattatag cataatatac aagtctgtga acggtggctc acgcctgtaa  11400
cccagcactg caggaggcca aggcgggtgg atcacatgaa gtcagcagtt cgagaccagc  11460
ctggccaaca tggtgaaacc ctgtctctag gaaaaacaca aaaattagcc gagcatggtg  11520
gtgcatccct gtaatcccag ctcctactct ggaggatgaa gcaggagaat gacttcaacc  11580
caggaggtgg aggttgcagt gagtggaggt tgcatcactg cactccagcc tgggtggcac  11640
aaggagactc cgtctcaaaa aataaaaata agaaatgcat aaatataaat ataatataac  11700
acacgcaaat gacaaaggga cctgaattcc aatcatgatt tttctatttc tctataatta  11760
cttctttgat cctttatctt atccattagg caatgagcct aaaacctctt ccctatttgg  11820
ctttctgtga gcatgagatc atatagaaaa tgtgaaagtc cgctgaatcc tccagcacag  11880
atcctggaat agagaaagtg ctctggtcat cacaaaaaaa acttgcccac tcacccaaat  11940
cccccacctc accoctactt ccaatcacct gtggagattc aggtagacca tggggaggta  12000
aacattaaca ctccttggag tgagtccaga tcttggaatc agagatcagc gacagcacta  12060
gctcctgctc ccctttccta ctaattcaca ggaggacagg tggtattgaa gcaatagatg  12120
gccgaggggg tggtccttcc cccagcctct cgggtagaac agcagcctaa tatgtgtctc  12180
ccgagatcac aaagagcagc aggtttcaca cgggcttcaa cactatttcc tggccgtttg  12240
acataagaga attctatttc gctttttttta tcttgatttc acttttgttt tctttccttg  12300
gagaatgcaa gttgtttgat tcaagaatgc tgtggatgta gaaaccctaa agcacattcg  12360
ctgtgaatca atcccagtcc agtcttccca gagaagactc taaacacctc ctggactgca  12420
cctgggccta tgccaattcc tatcactcac cgtcactcca gggagacaga acacacagag  12480
aatacgttac ataggcaggt tcattactaa cagataagca gcgagtgaca acagaaacct  12540
atatttcaat gtgagccagt ccctcaaggc tcagaaaagc tcctcgggac atatggagtc  12600
accccatttg cagtgtagct gcgggaagcc agaaagcagc ccagcctggg ttttgtaccc  12660
tggagccaca ggaagcactc agctaaagca ctgcatgacg tcctccagga agaacaggaa  12720
gacagcccag ggtgttctga gacgttcctc ctgatctcag gaagttgctg tcttaggcca  12780
tttttgttgc tctaaaggaa cacttgagcc tcggtaactt ctaaagaaaa gagattggtt  12840
tgcctcaccg ttctgcaggc tgtactggaa gcatggcacc agcatctatt tctcgtgacg  12900
gcctcaggct gctcccactc tggcagaagg gaaggagggt ctgtctgtgc agagaccaca  12960
gagatcacac ggcaagagag ggagcaaggg ggagggggag tgatggagct tccaagctct  13020
ttttaacaac cagctctccg ggaactaata gagggggaac ttgctaaccc cgtctccttg  13080
```

-continued ggacagcatt gatgtgttca tgatggatcc acctccatga cccaaacacc tctcaagagg 13140
cccaacctcc cacagtgggg gtgaaatttc aatgtgaggt ttgaaggggt caaacatctc 13200
aactaaagta gtcgtatcct cagcacgttc tatggttact atgagagcta taactgaaaa 13260
agcaggagaa agctgggtct cctgccatct gggtgcttgt cctaaagaga tgttttatgt 13320
ggttacctgt caatcaagaa atgcgagaca attcataaag aggaactgct aagattagct 13380
tcttattggt gtctcatctt cttccaggta acccccgaca cctgcacatt ctgattggga 13440
cctcagtggt catcatcctc ttcatcctcc tcttctttct ccttcatcgc tggtgctcca 13500
acaaaaaaag taagtctcac gaagcagagg ccagagagct cagggccatg tggggaagca 13560
ggatgggagc actcaggtgt gtgttcctca caaacaggat ggtccctggc ccaaggcagc 13620
agccacagag gcaggacttt ctagagaggg caccagactc cctgcccctg ccttcaactc 13680
acagaccgtt gcctgattct gaactgtatc ctcatgtccc ctgcagccac tcacatccag 13740
gagaaggttc catgacaggc agaaagtggg agacagaatc aatgggatgg gaactcagag 13800
ctattcatgg gatgggtcct tgagctcaga gagatagaat gtctgagtct gctgttggca 13860
actgagggac ctcagccacc tatggtctcc ccctgtatgt tggtatctgc ttatgaaatg 13920
aggacccaga agtgccctcc gagctgtttt gttgacttcc gtctcctaca gatgctgcgg 13980
taatggacca agagtctgca gggaacagaa cagcgaatag cgaggtaggt actcctcggc 14040
ccgggctcgt ggctactgtt attcccaaag agtcctggaa aatgtgagca ccctccctca 14100
ctcagcattt ccctctctcc aggactctga tgaacaagac cctcaggagg tgacatacac 14160
acagttgaat cactgcgttt tcacacagag aaaaatcact cgcccttctc agaggcccaa 14220
gacaccccca acagatatca tcgtgtacac ggaacttcca aatgctgagt ccagatccaa 14280
agttgtctcc tgcccatgag caccacagtc aggccttgag ggcgtcttct agggagacaa 14340
cagccctgtc tcaaaaccgg gttgccagct cccatgtacc agcagctgga atctgaaggc 14400
atgagtctgc atcttagggc atcgctcttc ctcacaccac aaatctgaat gtgcctctca 14460
cttgcttaca aatgtctaag gtccccactg cctgctggag aaaaaacaca ctcctttgct 14520
tagcccacag ttctccattt cacttgaccc ctgcccacct ctccaaccta actggcttac 14580
ttcctagtct acttgaggct gcaatcacac tgaggaactc acaattccaa acatacaaga 14640
ggctccctct taacgcagca cttagacacg tgttgttcca ccttccctca tgctgt 14696

<210> SEQ ID NO 68
<211> LENGTH: 14761
<212> TYPE: DNA
<213> ORGANISM: Homo sapiens

<400> SEQUENCE: 68
gtatgagagg ttggatctga gacgtctttt gagtctggtc gtagtgaagg acgcaaggtg 60
tcaattctag tgagaacaat ttccaggaag ccatgttccg ctcttgagcg agcacccact 120
gggcctcatg caaggtagaa agagcctgcg tacgtcaccc tcccatgatg tggtcaacat 180
gtaaactgca tgggcagggc gccaaataac atcctgtgcg ctgctgagct gagctggggc 240
gcggccgcct gtctgcacag acagcaccat gtcgctcatg gtcgtcagca tggtgtgtgt 300
tggtgagtcc tggaagggca tcgagggagg gagtgcgggg atggagatcg gggcccagag 360
ttggagatat aggcctggaa gtggagttat gggcctagag atggagtgat gggcctagaa 420
gtggagatct gggcctggag tggagatctg ggcctggagt ggagatatgg gcctggaggt 480
tgagatatgg gcctgcagta gagatatggg cttgtagtgg agacatgggc ctggagatgg 540

```
agatatgggc ctggagatgg agatatgggc ctgcagtaga gataggggcc tggagtggag    600
atatgggcct ggagtggaga tatgggcctg gaggtggaga tatgggcctg gaggtggaga    660
tatgggcctg gagtggagat atgggtctgg aggtggagat acgggcctgc agtagagata    720
tgggcctgga gtggagatat gggccaggag tggagttatg ggcctagaga tggatatctg    780
ggcctggagt ggagatatgg gcctaggaag gagatatggg cctgggtgtg gagatatggg    840
actggagagg tgatatgggc ctggagtgga gatatgggct tagggtggag atctgggcct    900
ggggcggaga tatgggactg gattggagat aggggcctag ggtggagatc tgagcctgga    960
ttggcgatat gggcctaggg tggaaatatc agcctggagt ggagatatgg gcttggggtg   1020
gggatatggg cctggaaact gggtctctgc acagccgaca gccctgttct tgggtgcagg   1080
taggcactga gggtgagttt aacttcagcc caggaagggc ctggctgcca agactcacag   1140
cccagtgggg gcagcaaggg aggcctggtt tgcctgcaga tggatggtcc atcatgatct   1200
ttctttccag ggttcttctt gctgcagggg gcctggccac atgagggtga gtccttctcc   1260
aaaccttcgg gtgtcatctc cccacataag aggattttcc tgaaacagga gggaagtcct   1320
gtcggggagt ctctcataaa ctaggaagag aggaccctgg ggtgctcagc ccacatttct   1380
gacctcgcct ccctggcctc tcaacccctt ggcagagtca agttctgtgg ggaccagggt   1440
tagactgggg tgctcaaagc tggggtgtgt ggttgggaag tggtaggaac agcagatcct   1500
ctgaggacaa aggtgttact cacacacttc agcgtttcca tgatggtagg ggctgcagtg   1560
tggctgctgt cattctacca gaagaggtgg gaaaccacag ccatggccct gacattccaa   1620
atcctctgat gggggctcag ttgtttattt tcgttcaggc atccgctgat atccattcac   1680
aaaggacatg ccctccacct catgtctacc ctgtgttgtt ttatgtgagt aatcttacag   1740
tattaaaatc tagtaggagt ctctttactc agcacttgct caaagttctc agctgaggct   1800
tttgttgtag ggagacacca tgtctttgcg ggatgggtcc ttccttcagc cctgggcacc   1860
aaggtgtgat agtagccata gaaacgtgga aagcgaggag aatcttctga gcacagggag   1920
ggaagggcag ttccacatcc tcctctctaa ggcggcgcct ccttctcccc aaggtggtca   1980
ggacaagccc ttgctgtctg cctggcccag ccttgtggtg cctctaggac atgtcattct   2040
tcggtgtcac tcttatcttg ggtttaacaa cttcagtctg taaaaggaag gtggggtgcc   2100
tgtccctgag ctctacaaca gaatattctg gaacagcctt ttcatgggcc ctgtgacccc   2160
cgcacacaca gggacataca gatgtcgggg ttcacacaca cactccccca gtgggtggtc   2220
agcacccagc aaccccctgg tgatcgtggt cataggtcag agggctcctg tcttggattc   2280
tccttgtccc acctcctgaa tcccagagct tctgttgggc atgtccttga gggtcccatc   2340
acgcaggccc tgactgtatt tgtggtaaag ggggattgaa tacagggaaa tgggtgctgt   2400
ggtgggaaga ataattgtcc ccagtgatga ctacattcta atccctggag tctgtgacta   2460
tttatgttat aggggaaggg actgaagggg aagatggagc tcatggggag acagcctgga   2520
ctgtcccact gggctcagtg taatcacaag ggtgcacatg aaaggaggag gaagagggga   2580
gtggggatta gagcagtcca gtggaagtct tcaccagctt tgaaggtgga ggaaggccaa   2640
gatccatgaa tgcaggtggc ctatagaggc tggaaaagtc aaggaactga ttctccagag   2700
tctccagagg gaacaaagcc ctgcagatgc cttgatttta gcccaggaaa aatagggtcc   2760
aatttctgtc tccagtactg gaaggtgtca gtgtggtctc tcctgctgcc atgcttctga   2820
taattttcta cagcagcaac aggaaaccaa cactggaacc caggtcaagg acaagttaag   2880
```

-continued

```
aaacaaccca aggaaagcca ggcatggtgg caggtgcatg taatcctagc gactcaggag   2940
gctgagggca ggagaatcac ttgaacccag gagacagagg ttgcagtgag cctagaccac   3000
accacttcac tccagcctgg gtgaaggagt gagactctgt ctccataatt aattaattaa   3060
ttaaagaaac caaacaagga gaaggttggc taccctgaga tcagcaaggg tgggatgatg   3120
atgccaccac caggctccat ccacataggg aggggttgat actcctccaa ccagcaccag   3180
gagccagcct atggaagctg gcaccatgga gaaggcacag gcatggcaag agtggctccc   3240
agtccccacc aggaacaggg tgtgtggaca ctggtgcctg ccttattcat cagttcatac   3300
cttctgccaa ggattgcaat tcatccaaaa gagattgaac caggctgata agagcctgga   3360
tgtgcagcct atcctggttc ctctttcacc cccacataaa cagcaggaaa tacattagtg   3420
tgaaatagat acaacacccc aagagatgag gctcagccca gtgggaaggg aatcagaggc   3480
tactagagac agagggacag agaagaggga gggagacaga tggaaggacc tgcaccagga   3540
gttaagggca cagaaaagaa catgaagaca cagagaggaa ggagagagac agacaccagc   3600
aaggggaagc ctcactcatt ctaggtgcca tggatgggat gataaagaga gacaccttct   3660
aaactcacaa cctctcttcc taggagtcca cagaaaacct tccctcctgg cccacccagg   3720
tcccctggtg aaatcagaag agacagtcat cctgcaatgt tggtcagatg tcaggtttca   3780
gcacttcctt ctgcacagag aagggaagtt taaggacact ttgcacctca ttggagagca   3840
ccatgatggg gtctccaagg ccaacttctc catcggtccc atgatgcaag accttgcagg   3900
gacctacaga tgctacggtt ctgttactca ctccccctat cagttgtcag ctcccagtga   3960
ccctctggac atcgtcatca caggtgagag tgtccggaca ttctcattgt cattgggatg   4020
cagagtgaat gatccacgac ttggaacccc caggtagttg taaggaagat gagcttggta   4080
ttcttatgga gagagactga cttgctgagg tttgtaccaa cagagacaga gaaacaggag   4140
acacaagtac agaccaggtg tcataacaga ggacagacac aggggccata cagggagtta   4200
gaaaagacag aaagagttaa aagagacaga cagacagaca tgtcccagag agaggtgtcc   4260
ctccatgctg actttgctca cagacctggc acaggttaga agtttcattt ctgttttacc   4320
tccacaaagt gttctctacc aggagaaccc aaggacaccc atatttatga cctgagttgg   4380
gccctgtggc ctcaggcctt gtggcaccta caggccatgt ttattctgac acctctgcct   4440
tccatgtaat ggagagtaat cgtcccagga tatcatggcc ccagaacacc aacccctgta   4500
tgctgtgtga acttgtggtc tccagactgg attctgtggc tcacattcca aataacccca   4560
catatgaaag gatcactgag aggcacagag aaaaatcagg aacaccaaaa agcaaagaca   4620
taaacacaca gagaatgagc cagaggaagg agattgagag actcacagac acataaagag   4680
agagaaaaga gggcagagga gtggtgagaa tgatggcagg gagcagagaa aagcactaaa   4740
attagagtcc tgagagagag gcacaaggac atagaaacat ggagatgtgg ggatgaattg   4800
cagagattcc aaagagaact agagagaccg agaggcagag caagacagat gatagatgga   4860
tagatataga tagatgataa ataggtagat gatagataat aggttaaaga tacatagatg   4920
atgattgatt gattcattaa tagataatac atagagatga tgatgatgaa gacagataat   4980
acgtacagat agagaggcag acagaaatca tagagagaga gatgatacat acatataaat   5040
aacagatgat tgatggatag atagacaagt gatagataca tagatgatat atagatatag   5100
atgacaggta gagaatttgt agataggcac cgaatagata aatagataga tcgacagata   5160
atagatagaa atatgcagaa agttatgaac aggacacaac gtgagaaact tagaatttaa   5220
aaaagtaaca tcaagtcaac caatccaagg agagtcagag agaataaaag aatccaaaaa   5280
```

-continued

```
gggaaaacat atctagaggt ggggaagcga ggtcagagac ctagagagac agagaaggtg   5340
gaagaaggaa atagacatga agagagatgg ggtggagggt gagagagaga gagagagaga   5400
gcattaggtc atagagcagg ggagtgagtt ctcagctcag gtgaagggag ctgtgacaag   5460
gaagatcctc cgtaaggaaa atgcctcttc tcctccaggt ctatatgaga aaccttctct   5520
ctcagcccag ccgggcccca cggttctggc aggagagagc gtgaccttgt cctgcagctc   5580
ccggagctcc tatgacatgt accatctatc cagggagggg gaggcccatg aacgtaggtt   5640
ctctgcaggg cccaaggtca acggaacatt ccaggccgac tttcctctgg gccctgccac   5700
ccacggagga acctacagat gcttcggctc tttccgtgac tctccatacg agtggtcaaa   5760
ctcgagtgac ccactgcttg tttctgtcac aggtgaggaa accccatatc tgtctcatgt   5820
cctatgatcc tagagcctta gctgaggagc ttcctgctga tgatggagag aagcatggac   5880
agatgcagag agaagacgaa gcttgggtgt gagggaggga tcagggcaca ggatggcaga   5940
cagggcacct ccaaaccctc ctacacggcc tgcatgaagg cccgcggcca gggctccagg   6000
cacacaggca gatggagaaa acggtcagga gagacccaga ggagagagac tgggctcagt   6060
ttgggaagat cagaggttcc ctcagcccct caacattacc catttcccag aagcccatcc   6120
tggcctctca cccacacagg gatgtcatca ccagcaaccc ctacaccctt tacttttgtt   6180
tgaagaaata tttattgagg ataaatatac ctatatagct taccaccttt aacatttttt   6240
ttttttttga ggcagagtct agctctgtcc cctatgctgg agtgcagtgg cacaatctca   6300
gctcactgca acttccgcct cctgggttca agtgattctc ctgcttcagc cacctgagta   6360
gctggtgcta caggcgcgca ccaccacgcc aggctacttt ttgtattttt agtagagagg   6420
gggtttcacc atgttggtcg agctggtctc caactcctga ccacgtgatc cacccgcatc   6480
tgcctcccaa agtgctggga ttacaggcat gagccaccac gcccagccac atttaccatt   6540
tttaagtgta aagtctagtg gtcataaata catttatata tatatatata tatatatata   6600
cacacacaca cacatatata aacatatata tatatatata tatatatata tatatatata   6660
tatatttttt tttttttttt tttttaccct ccaccctttt attcctggcc tctggaagcc   6720
accattctac tctctacctt catgagatcc accttttagc tctgtatatg ggtgagaaat   6780
gggaatcttt gtaatgactt ccagttccat ccatgtggct gcaaatatca ggatgttatt   6840
ctttctatgg atgagtagtc tccactgtgc gtatgtacta cattctctct atccattcat   6900
ccactgatgg gcaggtaggt tgactccaca tcttggctac tgtgaacagt gctgcaccaa   6960
tcatacgagt gcagatatca cttcgatata ttgatttact ttcctttgga tataaaccca   7020
gtagtgaaat tgctggatac tatgaaagtt ctctttttag ttattcgttt gttgttttgt   7080
ttttgttttt gagacagttt ccctctgtgc ccaggctgga gtacaagtga agtcatcttg   7140
gctcattgca acctccgcct cctgggttca aatgattttc ctgcctcagc ctccctagta   7200
gctgggatta caggtgcacg ccaccatgcc tggctacttt ttgttttttt tagtatagat   7260
ggggtttccc catgttggct gggctgctct caaactcatg acctcaactg aggtgcccgc   7320
ctcggtctcc caaagtgccg ggattacagg catgatccac ctcacccaac ctctttttag   7380
ttctttaaag gacttccaca cttttctccg taaaggctgt actaatttac actcctacca   7440
acagggtatt agggttctcc tttctctacc actttggcag gatttccttt gcctgtcttg   7500
cagctaaaag ccattttatt ttatttcatt ttattttgag atggagtttc gctcttgtca   7560
cccaggctgg agtgcagtgg tgcgatctcg gctcaccaca acctccacct cccaggttca   7620
```

agcgattctc ctgcctcagc ctcccgagta gctggaatta caggcacacg ccaccacgcc 7680
caactaaatt ttgtattttt agtagagaca gtgtttcttc atgtgggtca gactggtctc 7740
aaactcccga ccttatgagg ttcacccacc tcaggctctc aaaggtctag gatgacagac 7800
gtgagccacc acgcccggcc taaaatccat tttaatgggg tgagatgaaa actcactttg 7860
attttaattt gtgtttctct gatgatgagt gaaactgagc actttttagt atgtggggaa 7920
atttcatgtg ttttgctcct ttttcaatta aatcgtttgt tttattgagt tgtttgagct 7980
tcttatattt ctagttatta atcccatctc agatgcatag tttgcacata tttgctccca 8040
atctgtgggt tgtctcttca ctttgttggt ttatttttag cggtgcagaa gttgcttagt 8100
ttgaggtaat cccaatggtc tatttttgct tcgattactt gtgttttgaa ggtttaaaac 8160
aaaatgtctt ccttcagaca aatgtcctgg agcatttccc caatattttc ttctacgtgt 8220
ttcataggtt caggccttag actcacatct ttaatccatt ttcatttgag ttttgtgtat 8280
agtgacaggt agaggtgcag tttcattcct ctgcatgtag atgtccaggt ttccctgcac 8340
tgtttattga aaagactgtc ctttcctgat tgtgagttct tggcaccttt gtcaaagtcc 8400
attggatggg ctgggcatgg tggctgacac ctgcaatttc agcactttgg gagcccaagg 8460
cgggtggatc acctgaggcc aggagttcaa gattagtctg gccgacgtga tgaaacattg 8520
tctccactaa aaatataaaa attagctgag catggtggtc agcacctgta ataccactac 8580
tcaggagttt gaggccagag aattgattga acccaggagg ctgtggtggc agtgaaccga 8640
gattgcacct ctgcactcca gcctgggtga cagagcgaga ctccatctca aaagaaaaaa 8700
gaaaaaaaca ttggaggtaa atgcatggat tatatctgtg ttcttcattc tgctccattg 8760
ttctacgtgc ctttctttat gccaatgtga tgctgttttg cttactacag ctctgtaaca 8820
tattttgaga tcaggtagtg tgatgctcct gttttctctt tataccttga agtctcaaga 8880
cagtgggcgt cacatacaaa aattacggaa aaaaggatcc caggactccc agggcccaat 8940
attagataac agagtgttgg ccatgaacca acctcaaaga tttccattga gtagaggaca 9000
gacaccctca tttcctcacc tctctcctgt ctcgtgttct aggaaaccct tcaaatagtt 9060
ggccttcacc cactgaacca agctccgaaa ccggtgagta cagaaccctc ttatatccgc 9120
ttttggaaac ctggggaggt agaaaccttc gatgcaggca ttgactcagc atctcgcagc 9180
tctgacattg tacgcctgtc ttctaccatc tccgaactcc agatactcca acagcgaaag 9240
ggatctgggc ccaacctagg gctcagtgaa atctcttaat ctctcatttt atggagctga 9300
gacctcctac aagctagaag aatgattgcc aatctgacat ccttctcagg aaaaatgcaa 9360
tgtttgttct gcctgcattc ctaactggag gataaattcc tgggggcttg agagagggaa 9420
gggaagggaa catctgatga gggcgaggtg ttttagagaa gttccacttg ccaaggaatg 9480
aattactgtt ggtcatgaag caaccctggc tgactcagca gagcaacagc cttgccgtaa 9540
cagagaacgg agctcatgca cgcacacttc gactcactga ctcattcagc cacggcccca 9600
tgctcaggct gtgcagtgcg gaaccttttc ctattgttgc cataacaaat ttccacaaga 9660
ttcgtgggtg aaaacaaaac ggttttttaa ttatcttaca gtgctgtagc tcaaagtagg 9720
aagtgcatct tactgggcta aaatcaaggt gacagcaagg ctgccttccc tctgaggatt 9780
ccaggcaaga atctgcttct cacttatccc agcttctaaa ggctcccagt tccttggctc 9840
ctgttcccct tcctccttcc tcaaagccca caaagactgg tcacatctca catggcatca 9900
ctcagtgcct tcttccttac cacacctctt tctctgaatg ctgctctccc ttcttcctta 9960
tcttttgaaa acttggggat tctattgggt tcaccaagat gaaaatccct cataatctcc 10020

```
tggaaatcat ccaggatacc cttgttttaa gttcagctga ttagcaaccg caattccatc  10080
tacaatcttc attcctcctt tccatgtaaa ataacatatt cacaagctat ggaggctagg  10140
acagggacat tttggggtgg gacagcattc tcctgccttc cacaaacggt gaacaagatg  10200
catttggctt ctgcccttgg gacactgata ttgcagatgg ttaaatggga gggcagaaaa  10260
tgaatgcaca agtggatcta taaatgaatg atccattggg aagcatctgt gcatgaaatc  10320
tattttttgt ttgttctttt gtttattgag acagagtcgc cctctgtctt ccaggctaca  10380
gtgcagtgtc acgatcttgg ctcactgcaa cctgcgtctc ctggattcaa gtgattctcc  10440
tgcctccgcc tctcgagtag ctgggattac aggcaactgc caccgtgccc ggctaattct  10500
ttttgtatat tttttgtaga gaggatgttt caccacgttg gccaagcttg tctgaaactc  10560
ccaacctcaa gtgatccgac cgtctcagca tgccaaagta atgggactac aggcgtgagc  10620
cactgtgccc agccagaatt caaaatcaat aatagataat gctgagtgta tgatttcagg  10680
tgacaaagaa ggtctcacta ttcagatatt tgtgacatta atgaaaaaca cggattgaac  10740
ccctgaaaga ttggcggaag gattttgcac acacagctgt cagccgtgaa ggcacaaagg  10800
tgaaaacaat ctgatgtgga aggaagaggc tctgcctcaa atgctgggaa tgatgtgggg  10860
agaatgacaa gacgactgta gagagacgga gagcacactg ggtacacagg aaactaagga  10920
gcaacaagga gtgtgtgttt gacactcaca gccattggat tcacctcggg gtaaccagga  10980
atccctacat gattaatatg actgacatga aaataaggga ggctcagttg cataactgga  11040
atctaggaga ccgtggaaaa ggcaattgcc accccactgg tgaaatgtgg tgctgattta  11100
gacactaaat gaatgaagta gatggatata agatatgttt gtgaggtaga atcattgact  11160
ggaaacgctt actgggtttg attttcctac ttgtttaatc ctcgcttaat taatttcttt  11220
ctgagattta ttcatcctac acataaatca atacctggca aaggagtgac agatatatga  11280
gtggtggtgg aaatgaagag acttattata gcataatata caagtctgtg aacagtggct  11340
cacgcctgta acctagcact gcaggaggcc aaggtgggtg gattccatga agtcaggagt  11400
tccagaccag cctggccaac gtggtgaaac cctatctcta ctaaaaatac aaaaattagc  11460
cgagcacgat ggtgcatccc tgtaatccca gctcctattc tggaggatga agcaggagaa  11520
tgacttcaac ccagtaggtg gaggttgcag tgagtggaga ttgcatcact gcactccagc  11580
ctgggggaca caaggagact ctatctcaaa aaataaaaat aagaaataca taaatataat  11640
aaaacacaca cgaatgacaa aggcacctga attccaatca tcgtttttct atttctctat  11700
aattacttct ttgatccttt atcttatcca ttaggcaatg agcttaaaac ctcttcccta  11760
tttggctttc tgtgagaatg agatcacata gaaaatgtga aagccctcag aatcctccag  11820
cacagatcgt ggaatagaga aagtgctctg ttcatcgcaa caaaaaactt gcccactcac  11880
ccaaatcccc cacctcaccc ctacttccaa tcacctgtgg agattcagat aggctatggg  11940
gaggtaaaca ttgatactcc ttggagtgag tccagatctt ggaatcagag atcagtgcca  12000
gcactagctc ctgctcccct ttcctactaa ttcacaggag gacaggtggt attgaagcaa  12060
tagatggccg agggggtggt ccttccccca gcctctcggg tagaacagca gcctaacatg  12120
tgtctcccga gatcacaaag agtagcacgt ttcacacggg cttcaacact atttcctggc  12180
catttgacat aagagaattc tacttagctt tttttatctt gatttcactt ttgtttcctt  12240
ttcttggaga atgcaagttg tttgattcaa gaatgctgtg gatgtagaaa tcctaaagca  12300
cattcgctgt gtatcaatcc cagtgcagtc ttcccagaga agactctaaa tacctcctgg  12360
```

-continued

```
actgcacctg ggcttatgcc aattcctatc actcaccgtc actccaggga gacagaacac  12420
acagagaata cattacacag gcaggttcat tactaacaga taagcagcga gtgacaacag  12480
aaacctacat ttcaatgtga gccagtccct caaggctcag aaaagctact cgggacatat  12540
ggagtcaccc catttgcagt gtagctgggg gaagccagag agcagcccag cctgggtttt  12600
gtactgtgga gccacaggaa gcactcagct aaagcactgc atgacgtcct cctccaggaa  12660
gaacaggaag acagcccagg ctgttctgag acgttcctcc tgatctcagg acgttgctgt  12720
cttagtccat ttttgttgct ctaaaggaac acttgagcct gggtaacttc tagagaaaag  12780
agattggttt gcctcacagt tctgcaggct gtactggaag cgtggcacca gcatctattt  12840
ctcgtgacgg cctcaggctg ctcccactct ggcagaaggg aaggagggtc tgtctgtgca  12900
gagaccacag agatcacacg gcaagagagg gagcaagggg gagggggagc gatggagctt  12960
ccaagctctt ttgaacaacc agctctccag gaactaatag aaggggaact tgctaacccc  13020
gtctccttgg gacagcattg gtctgttcat gatggatcca cctccatgac ccaaacacct  13080
ctcaagaggc ccaacctccc acagtggggg tgaaatttca atgtgaggtt tgaaggggtc  13140
aaacatctca actaaagtag ttgtatcctc aacacgttct atggttacta tgagagctat  13200
aactgagaaa gcaggagaaa gctgggtctc cctccatctg ggtgcttgtc ctaaaggggt  13260
gttgtatgtg gttacctgtc aatcaagaaa tgtgagacaa ttcataaaga ggaactgcta  13320
tgattagctt cttattggtg tctcctcttc ttccaggtaa ccccagacac ctgcatgttc  13380
tgattgggac ctcagtggtc atcatcctct tcatcctcct cctcttcttt ctccttcatc  13440
gctggtgctg caacaaaaaa agtaagtctc acgaagcaga ggccagagag ctcagggcca  13500
tgtggggaag caggatggga gcactcaggt gtgtgttcct cacagacagg atggtccctg  13560
gcccaaggca gcagccacag agggaggact ttctagagag agcaccagac tccctgtccc  13620
tgccttcagc tcacagacca ttgcctgatt ctgaactgta tcctcatgtc ccctgcagcc  13680
actcacatcc aggagaaggt tccatgacag gcagaaagtg ggagacagaa tcaatgggat  13740
gggaactcag agctattcat gggatgggtc cttgagctca gagagataga atgtctgagt  13800
ctgctgttgg caactgaggg acctcaggct cctatggtct ccccctgtat gttggtatct  13860
gcttatgaaa tgagggccca gaagtgccct ctgagctgtt ttgttgactt ccgtcttcta  13920
cagatgctgt tgtaatggac caagagcctg cagggaacag aacagtgaac agggaggtag  13980
gtgctcctcg gcccagcctc gtggctagtg ttattcccaa agagtcctgg aaaatgtgag  14040
caccctccct cactcagcat ttccctctct ccaggactct gatgaacaag accctcagga  14100
ggtgacatat gcacagttga atcactgcgt tttcacacag agaaaaatca ctcgcccttc  14160
tcagaggccc aagacacccc caacagatat catcgtgtac acggaacttc caaatgctga  14220
gccctgatcc aaagttgtct cctgcccatg agcaccacag tcaggccttg aggggatctt  14280
ctagggagac aacagccctg tctcaaaact gggttgccag ctccaatgta ccagcagctg  14340
gaatctgaag gcgtgagtct gcatcttagg gcatcgctct tcctcacacc acaaatctga  14400
acgtgcctct cccttgctta caaatgtcta aggtccccac tgcctgctgg agagaaaaca  14460
cactcctttg cttagcccac aattctccat ttcacttgac ccctgcccac ctctccaacc  14520
taactggctt acttcctagt ctacttgagg ctgcaatcac actgaggaac tcacaattcc  14580
aaacatacaa gaggctccct cttaacacgg cacttagaca cgtgctgttc caccttccct  14640
```

-continued

```
catgctgttc cacctcccct cagactagct ttcagccttc tgtcagcagt aaaacttata  14700

tattttttaa aataatttca atgtagtttt ccctccttca aataaacatg tctgccctca  14760

t                                                                  14761
```